(12) United States Patent
Vazales et al.

(10) Patent No.: US 8,601,633 B2
(45) Date of Patent: *Dec. 10, 2013

(54) CLEANING OF BODY-INSERTED MEDICAL TUBES

(71) Applicant: Endoclear LLC, San Ramon, CA (US)

(72) Inventors: Brad E. Vazales, Petoskey, MI (US); Arthur Bertolero, Danville, CA (US); Ken Watson, Milwaukee, WI (US); James M. Gracy, Harbor Springs, MI (US); Clifton P. Colwell, Peoria, AZ (US); Craig B. Berky, Milford, OH (US); Alan Davidner, Claremont, CA (US)

(73) Assignee: Endoclear LLC, Petoskey, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/775,024

(22) Filed: Feb. 22, 2013

(65) Prior Publication Data

US 2013/0228196 A1 Sep. 5, 2013

Related U.S. Application Data

(63) Continuation of application No. 12/701,421, filed on Feb. 5, 2010, now Pat. No. 8,382,908.

(60) Provisional application No. 61/150,456, filed on Feb. 6, 2009.

(51) Int. Cl.
*B08B 9/00* (2006.01)
*A61M 16/00* (2006.01)

(52) U.S. Cl.
USPC .................. 15/104.05; 15/104.03; 15/104.16; 128/207.14

(58) Field of Classification Search
None
See application file for complete search history.

(56) References Cited

U.S. PATENT DOCUMENTS

| 62,816 | A | 3/1867 | Christoffel |
| 139,633 | A | 6/1873 | Turner |

(Continued)

FOREIGN PATENT DOCUMENTS

| JP | 08-029699 | 2/1996 |
| JP | 2006-026344 | 2/2006 |

(Continued)

OTHER PUBLICATIONS

Product/Catalog of EndoSheath® Technology in 2 pages. Vision Sciences [retrieved in Mar. 2010; Publication Date Unavailable]; retrieved at www.visionsciences.com/SWAPPID/96/SubPageID/32590.

(Continued)

*Primary Examiner* — Nicole Blan
(74) *Attorney, Agent, or Firm* — Knobbe, Martens, Olson & Bear LLP

(57) ABSTRACT

Systems, devices, and methods are disclosed for the cleaning of an endotracheal tube while a patient is being supported by a ventilator connected to the endotracheal tube for the purpose of increasing the available space for airflow or to prevent the build up of materials that may constrict airflow or be a potential nidus for infection. In one embodiment, a method for cleaning endotracheal tubes comprises inserting a cleaning device within an endotracheal tube while a cleaning member is in a compressed position, radially expanding the cleaning member to an expanded position within the endotracheal tube, and withdrawing the cleaning device from the endotracheal tube with the cleaning member in the expanded position.

17 Claims, 46 Drawing Sheets

(56) References Cited

U.S. PATENT DOCUMENTS

| | | | |
|---|---|---|---|
| 491,791 A | 2/1893 | Wilson |
| 655,313 A | 8/1900 | Tucker |
| 707,913 A | 8/1902 | Garrison |
| 1,040,088 A | 10/1912 | Wright et al. |
| 1,166,901 A | 1/1916 | Grobl |
| 1,588,557 A | 6/1926 | Thompson et al. |
| 1,608,347 A | 11/1926 | Thompson et al. |
| 1,612,842 A | 1/1927 | Thompson et al. |
| 1,656,465 A | 1/1928 | Baker |
| 1,738,601 A | 12/1929 | Metzger |
| 2,018,124 A | 10/1935 | Forster |
| 2,038,170 A | 4/1936 | Flavin |
| 2,073,811 A | 3/1937 | Shultz |
| 2,125,864 A | 8/1938 | Auckland |
| 2,157,421 A | 5/1939 | McFarland |
| 2,173,606 A | 9/1939 | Forster |
| 2,175,726 A | 10/1939 | Gebauer |
| 2,552,339 A | 5/1951 | Moon |
| 2,599,077 A | 6/1952 | Sturgis |
| 2,653,334 A | 9/1953 | Bay |
| 2,930,059 A | 3/1960 | Frank |
| 2,932,837 A | 4/1960 | Nooy |
| 2,957,189 A | 10/1960 | Nelson et al. |
| 2,958,884 A | 11/1960 | Hill et al. |
| 3,096,756 A | 7/1963 | Rosenfeld et al. |
| 3,105,555 A | 10/1963 | Villalon, Jr. |
| 3,130,431 A | 4/1964 | Reinhart |
| 3,257,698 A | 6/1966 | Ruegsegger |
| 3,445,879 A | 5/1969 | Taylor |
| 3,525,111 A | 8/1970 | Arx |
| 3,610,242 A | 10/1971 | Sheridan et al. |
| 3,669,098 A | 6/1972 | Takahashi |
| 3,776,222 A | 12/1973 | Smiddy |
| 3,946,459 A | 3/1976 | Armstrong |
| 3,948,273 A | 4/1976 | Sanders |
| 3,977,331 A | 8/1976 | Clavin |
| 3,991,762 A | 11/1976 | Radford |
| 4,031,590 A | 6/1977 | Clavin |
| 4,041,936 A | 8/1977 | Carden |
| 4,185,639 A | 1/1980 | Linder |
| 4,222,142 A | 9/1980 | DiProspero |
| 4,319,378 A | 3/1982 | Bowman et al. |
| 4,327,720 A | 5/1982 | Bronson et al. |
| 4,342,315 A | 8/1982 | Jackson |
| 4,351,328 A | 9/1982 | Bodai |
| 4,365,381 A | 12/1982 | Neuman |
| 4,502,482 A | 3/1985 | DeLuccia et al. |
| 4,527,553 A | 7/1985 | Upsher |
| 4,538,316 A | 9/1985 | Reinhart et al. |
| 4,565,187 A | 1/1986 | Soloway |
| 4,567,882 A | 2/1986 | Heller |
| 4,584,998 A | 4/1986 | McGrail |
| 4,586,491 A | 5/1986 | Carpenter |
| 4,622,709 A | 11/1986 | Matsuda |
| 4,637,389 A | 1/1987 | Heyden |
| 4,646,722 A | 3/1987 | Silverstein et al. |
| 4,662,871 A | 5/1987 | Rafelson |
| 4,698,932 A | 10/1987 | Schneider |
| 4,805,611 A | 2/1989 | Hodgkins |
| 4,815,459 A | 3/1989 | Beran |
| 4,825,859 A | 5/1989 | Lambert |
| 4,827,553 A | 5/1989 | Turpin, Sr. et al. |
| 4,846,153 A | 7/1989 | Berci et al. |
| 4,850,348 A | 7/1989 | Pell et al. |
| 4,877,016 A | 10/1989 | Kantor et al. |
| 4,889,106 A | 12/1989 | Watanabe |
| 4,892,095 A | 1/1990 | Nakhgevany |
| 4,976,261 A | 12/1990 | Gluck et al. |
| 5,000,260 A | 3/1991 | Fontenot |
| 5,003,657 A | 4/1991 | Boiteau et al. |
| 5,029,580 A | 7/1991 | Radford et al. |
| 5,065,754 A | 11/1991 | Jensen |
| 5,083,561 A | 1/1992 | Russo |
| 5,168,593 A | 12/1992 | Poje et al. |
| 5,193,525 A | 3/1993 | Silverstein et al. |
| 5,193,544 A | 3/1993 | Jaffe |
| 5,203,320 A | 4/1993 | Augustine |
| 5,240,675 A | 8/1993 | Wilk et al. |
| 5,251,356 A | 10/1993 | Oaki et al. |
| 5,257,620 A | 11/1993 | Schermerhorn |
| 5,271,381 A | 12/1993 | Ailinger et al. |
| 5,285,778 A | 2/1994 | Mackin |
| 5,287,848 A | 2/1994 | Cubb et al. |
| 5,297,310 A | 3/1994 | Coz et al. |
| 5,329,940 A | 7/1994 | Adair |
| 5,337,730 A | 8/1994 | Maguire |
| 5,375,589 A | 12/1994 | Bhatta |
| 5,383,243 A | 1/1995 | Thacker et al. |
| 5,400,771 A | 3/1995 | Pirak et al. |
| 5,405,755 A | 4/1995 | Markus et al. |
| 5,407,807 A | 4/1995 | Markus |
| 5,419,310 A | 5/1995 | Frassica et al. |
| 5,431,150 A | 7/1995 | Yabe et al. |
| 5,431,152 A | 7/1995 | Flam et al. |
| 5,431,637 A | 7/1995 | Okada et al. |
| 5,447,418 A | 9/1995 | Takeda et al. |
| 5,483,951 A | 1/1996 | Frassica et al. |
| 5,513,628 A | 5/1996 | Coles et al. |
| 5,520,607 A | 5/1996 | Frassica et al. |
| 5,540,225 A | 7/1996 | Schutt |
| 5,578,006 A | 11/1996 | Schon |
| 5,603,688 A | 2/1997 | Upsher |
| 5,615,439 A | 4/1997 | Bourrelly |
| 5,630,795 A | 5/1997 | Kuramoto et al. |
| 5,636,625 A | 6/1997 | Miyagi et al. |
| 5,643,221 A | 7/1997 | Bullard |
| 5,647,358 A | 7/1997 | Vilasi |
| 5,653,231 A | 8/1997 | Bell |
| 5,667,476 A | 9/1997 | Frassica et al. |
| 5,676,635 A | 10/1997 | Levin |
| 5,687,714 A | 11/1997 | Kolobow et al. |
| 5,692,729 A | 12/1997 | Harhen |
| 5,695,448 A | 12/1997 | Kimura et al. |
| 5,702,348 A | 12/1997 | Harhen |
| 5,709,691 A | 1/1998 | Morejon |
| 5,713,849 A | 2/1998 | Bosma et al. |
| 5,725,478 A | 3/1998 | Saad |
| 5,733,242 A | 3/1998 | Rayburn et al. |
| 5,768,741 A | 6/1998 | Leiman et al. |
| 5,791,337 A | 8/1998 | Coles et al. |
| 5,795,404 A | 8/1998 | Murphy et al. |
| 5,797,993 A | 8/1998 | Woehleke |
| 5,819,727 A | 10/1998 | Linder |
| 5,827,177 A | 10/1998 | Oneda et al. |
| 5,830,127 A | 11/1998 | DeCastro |
| 5,832,920 A | 11/1998 | Field |
| 5,836,918 A | 11/1998 | Dondlinger |
| 5,840,251 A | 11/1998 | Iwaki |
| 5,842,973 A | 12/1998 | Bullard |
| 5,845,634 A | 12/1998 | Parker |
| 5,846,183 A | 12/1998 | Chilcoat |
| 5,876,329 A | 3/1999 | Harhen |
| 5,902,413 A | 5/1999 | Puszko et al. |
| 5,904,648 A | 5/1999 | Arndt et al. |
| 5,913,816 A | 6/1999 | Sanders |
| 5,921,917 A | 7/1999 | Barthel et al. |
| 5,931,831 A | 8/1999 | Linder |
| 5,941,816 A | 8/1999 | Barthel et al. |
| 5,964,004 A | 10/1999 | Bean |
| 5,964,223 A | 10/1999 | Baran |
| 5,966,768 A | 10/1999 | Hahn |
| 5,987,683 A | 11/1999 | Leiman et al. |
| 6,045,623 A | 4/2000 | Cannon |
| 6,047,431 A | 4/2000 | Canonica |
| 6,082,361 A | 7/2000 | Morejon |
| 6,115,523 A | 9/2000 | Choi et al. |
| 6,120,434 A | 9/2000 | Kimura et al. |
| 6,123,666 A | 9/2000 | Wrenn et al. |
| 6,168,579 B1 | 1/2001 | Tsugita |
| 6,174,280 B1 | 1/2001 | Oneda et al. |
| 6,189,533 B1 | 2/2001 | Simon et al. |
| 6,190,330 B1 | 2/2001 | Harhen |
| 6,227,200 B1 | 5/2001 | Crump et al. |
| 6,276,017 B1 | 8/2001 | Lino et al. |

(56) References Cited

U.S. PATENT DOCUMENTS

| | | |
|---|---|---|
| 6,276,018 B1 | 8/2001 | Leiman et al. |
| 6,286,172 B1 | 9/2001 | Castagnoli |
| 6,299,576 B1 | 10/2001 | Ouchi |
| 6,318,368 B1 | 11/2001 | Morejon |
| 6,319,195 B1 | 11/2001 | Nakaichi et al. |
| 6,322,498 B1 | 11/2001 | Grevenstein et al. |
| 6,350,231 B1 | 2/2002 | Ailinger et al. |
| 6,353,774 B1 | 3/2002 | Goldenberg et al. |
| 6,354,993 B1 | 3/2002 | Kaplan et al. |
| 6,379,296 B1 | 4/2002 | Baggett |
| 6,398,775 B1 | 6/2002 | Perkins et al. |
| 6,461,294 B1 | 10/2002 | Oneda et al. |
| 6,484,345 B2 | 11/2002 | Seder et al. |
| 6,494,208 B1 | 12/2002 | Morejon |
| 6,500,271 B1 | 12/2002 | Moore et al. |
| 6,517,477 B1 | 2/2003 | Wendlandt |
| 6,520,907 B1 | 2/2003 | Foley et al. |
| 6,526,976 B1 | 3/2003 | Baran |
| 6,527,761 B1 | 3/2003 | Soltesz et al. |
| 6,530,881 B1 | 3/2003 | Ailinger et al. |
| 6,538,431 B2 | 3/2003 | Couchman et al. |
| 6,543,447 B2 | 4/2003 | Pacey |
| 6,554,765 B1 | 4/2003 | Yarush et al. |
| 6,569,089 B1 | 5/2003 | Covington et al. |
| 6,629,924 B2 | 10/2003 | Aydelotte |
| 6,655,377 B2 | 12/2003 | Pacey |
| 6,679,262 B1 | 1/2004 | Morejon |
| 6,681,783 B2 | 1/2004 | Kawazoe |
| 6,699,182 B2 | 3/2004 | Pilvisto |
| 6,699,331 B1 | 3/2004 | Kritzler |
| 6,725,492 B2 | 4/2004 | Moore et al. |
| 6,729,334 B1 | 5/2004 | Baran |
| 6,775,872 B1 | 8/2004 | Appleton et al. |
| 6,775,874 B2 | 8/2004 | Horton |
| 6,793,661 B2 | 9/2004 | Hamilton et al. |
| 6,832,986 B2 | 12/2004 | Chhibber et al. |
| 6,843,769 B1 | 1/2005 | Gandarias |
| 6,889,400 B2 | 5/2005 | Kawazoe et al. |
| 6,889,402 B2 | 5/2005 | Galantai |
| 6,890,298 B2 | 5/2005 | Berci et al. |
| 6,920,662 B2 | 7/2005 | Moore |
| 6,928,686 B2 | 8/2005 | Tomooka et al. |
| 7,036,510 B2 | 5/2006 | Zgoda et al. |
| 7,051,737 B2 | 5/2006 | Kolobow et al. |
| 7,052,456 B2 | 5/2006 | Simon |
| 7,056,284 B2 | 6/2006 | Martone et al. |
| 7,060,135 B2 | 6/2006 | Morejon |
| 7,081,097 B2 | 7/2006 | Martone et al. |
| 7,107,991 B2 | 9/2006 | Kolobow |
| 7,121,336 B2 | 10/2006 | Hatley |
| 7,128,071 B2 | 10/2006 | Brain |
| 7,159,590 B2 | 1/2007 | Rife |
| 7,182,728 B2 | 2/2007 | Cubb et al. |
| 7,243,653 B2 | 7/2007 | Nelson |
| 7,297,105 B2 | 11/2007 | Mackin |
| 7,322,357 B2 | 1/2008 | Nelson |
| 7,458,375 B2 | 12/2008 | Schwartz et al. |
| 7,458,955 B2 | 12/2008 | Owens et al. |
| 7,469,700 B2 | 12/2008 | Baran |
| 7,472,705 B2 | 1/2009 | Baran |
| 7,478,636 B2 | 1/2009 | Madsen et al. |
| 7,503,328 B2 | 3/2009 | Kolobow et al. |
| 7,527,058 B2 | 5/2009 | Wright et al. |
| 7,552,729 B2 | 6/2009 | O'Mara |
| 7,607,436 B2 | 10/2009 | Smaldone et al. |
| 7,658,708 B2 | 2/2010 | Schwartz et al. |
| 7,658,711 B2 | 2/2010 | Klemm |
| 7,669,600 B2 | 3/2010 | Morejon |
| 8,157,919 B2 | 4/2012 | Vazales et al. |
| 8,381,345 B2* | 2/2013 | Vazales et al. .............. 15/104.05 |
| 8,382,908 B2 | 2/2013 | Vazales et al. |
| 8,458,844 B2* | 6/2013 | Vazales et al. .............. 15/104.05 |
| 8,468,637 B2* | 6/2013 | Vazales et al. .............. 15/104.05 |
| 2001/0014768 A1 | 8/2001 | Kaplan et al. |
| 2002/0068851 A1 | 6/2002 | Gravenstein et al. |
| 2002/0108614 A1 | 8/2002 | Schultz |
| 2002/0162557 A1 | 11/2002 | Simon et al. |
| 2003/0109837 A1 | 6/2003 | McBride-Sakal |
| 2003/0213501 A1 | 11/2003 | Thomson et al. |
| 2004/0039252 A1 | 2/2004 | Koch, III |
| 2004/0084050 A1* | 5/2004 | Baran ..................... 128/207.14 |
| 2004/0154115 A1 | 8/2004 | Schultz |
| 2004/0176731 A1 | 9/2004 | Cheng et al. |
| 2004/0181194 A1 | 9/2004 | Perkins |
| 2004/0187892 A1 | 9/2004 | Maguire, Jr. et al. |
| 2004/0187893 A1 | 9/2004 | Maguire, Jr. et al. |
| 2004/0215061 A1 | 10/2004 | Kimmel et al. |
| 2004/0220451 A1 | 11/2004 | Gravenstein et al. |
| 2004/0221852 A1 | 11/2004 | Madsen et al. |
| 2005/0039754 A1 | 2/2005 | Simon |
| 2005/0090712 A1 | 4/2005 | Cubb |
| 2005/0172971 A1* | 8/2005 | Kolobow et al. .......... 128/207.14 |
| 2005/0182297 A1 | 8/2005 | Gravenstein et al. |
| 2005/0235995 A1 | 10/2005 | Tresnak et al. |
| 2006/0004260 A1 | 1/2006 | Boedeker et al. |
| 2006/0069312 A1 | 3/2006 | O'Connor |
| 2006/0100483 A1 | 5/2006 | Sundet et al. |
| 2006/0102200 A1 | 5/2006 | Esquenet et al. |
| 2006/0130847 A1 | 6/2006 | Morejon |
| 2006/0157059 A1 | 7/2006 | Johnson et al. |
| 2006/0191087 A1 | 8/2006 | Maguire, Jr. et al. |
| 2006/0202387 A1 | 9/2006 | Durand et al. |
| 2006/0264988 A1 | 11/2006 | Boyle |
| 2006/0287667 A1 | 12/2006 | Abela |
| 2007/0049794 A1 | 3/2007 | Glassenberg et al. |
| 2007/0106117 A1 | 5/2007 | Yokota |
| 2007/0106121 A1 | 5/2007 | Yokota et al. |
| 2007/0106122 A1 | 5/2007 | Yokota et al. |
| 2007/0129603 A1 | 6/2007 | Hirsh |
| 2007/0137651 A1 | 6/2007 | Glassenberg et al. |
| 2007/0142709 A1 | 6/2007 | Martone et al. |
| 2007/0167686 A1 | 7/2007 | McGrath |
| 2007/0175482 A1 | 8/2007 | Kimmel et al. |
| 2007/0185383 A1 | 8/2007 | Mulhern et al. |
| 2007/0215162 A1 | 9/2007 | Glassenberg et al. |
| 2007/0226927 A1 | 10/2007 | Suzuki et al. |
| 2007/0234494 A1 | 10/2007 | Suzuki et al. |
| 2008/0021273 A1 | 1/2008 | MacKin |
| 2008/0045801 A1 | 2/2008 | Shalman et al. |
| 2008/0098543 A1 | 5/2008 | Esquenet et al. |
| 2008/0105199 A1 | 5/2008 | Martin et al. |
| 2008/0141473 A1 | 6/2008 | Arai et al. |
| 2008/0142049 A1 | 6/2008 | Onishi et al. |
| 2008/0172033 A1 | 7/2008 | Keith et al. |
| 2008/0200761 A1 | 8/2008 | Schwartz et al. |
| 2008/0208000 A1 | 8/2008 | Schwartz et al. |
| 2008/0257355 A1 | 10/2008 | Rao et al. |
| 2008/0267688 A1 | 10/2008 | Busted |
| 2009/0032016 A1 | 2/2009 | Law et al. |
| 2009/0044353 A1 | 2/2009 | Galantai et al. |
| 2009/0049627 A1 | 2/2009 | Kritzler |
| 2009/0099421 A1 | 4/2009 | Shalman et al. |
| 2009/0107503 A1 | 4/2009 | Baran |
| 2009/0118580 A1 | 5/2009 | Sun et al. |
| 2009/0119856 A1 | 5/2009 | Onishi |
| 2009/0143645 A1 | 6/2009 | Matthes |
| 2009/0149716 A1 | 6/2009 | Diao et al. |
| 2009/0155770 A1 | 6/2009 | Brown et al. |
| 2009/0178681 A1 | 7/2009 | Bracken |
| 2009/0192355 A1 | 7/2009 | Mejia |
| 2009/0318757 A1 | 12/2009 | Singh |
| 2009/0320834 A1 | 12/2009 | Cuevas et al. |
| 2010/0010307 A1 | 1/2010 | Schramm |
| 2010/0069722 A1 | 3/2010 | Shalman et al. |
| 2010/0094090 A1 | 4/2010 | Mejia |
| 2010/0186748 A1 | 7/2010 | Morejon |
| 2010/0199448 A1 | 8/2010 | Vazales et al. |
| 2010/0199999 A1 | 8/2010 | Vazales et al. |
| 2011/0023885 A1 | 2/2011 | Vazales et al. |
| 2011/0023886 A1 | 2/2011 | Vazales et al. |
| 2011/0023887 A1 | 2/2011 | Vazales et al. |
| 2011/0023888 A1 | 2/2011 | Vazales et al. |
| 2011/0048427 A1 | 3/2011 | Zachar |
| 2011/0290246 A1 | 12/2011 | Zachar |

(56) References Cited

U.S. PATENT DOCUMENTS

| | | |
|---|---|---|
| 2013/0023729 A1 | 1/2013 | Vazales et al. |
| 2013/0030249 A1 | 1/2013 | Vazales et al. |
| 2013/0104884 A1 | 5/2013 | Vazales et al. |

FOREIGN PATENT DOCUMENTS

| | | |
|---|---|---|
| WO | WO94/03226 | 2/1994 |
| WO | WO 9403226 A1 * | 2/1994 |

OTHER PUBLICATIONS

Product/Catalog of Endoscopy Systems and EndoSheath® Technologies—BRS-5000 Flexible Digital Video Bronchoscope in 2 pages. Vision Sciences [retrieved in Mar. 2010; Publication Date Unavailable]; retrieved at www.visionsciences.com/SWAPPID/96/SubPageID/38845.

Healthcare Professionals Distribution Pulmonology, Global in 3 pages. Vision Sciences [retrieved in Mar. 2010; Publication Date Unavailable]; retrieved at www.visionsciences.com/SWAPPID/96/SubPageID/39771.

Conti, G., et al., A new device to remove obstruction from endotracheal tubes during mechanical ventilation in critically ill patients, Intensive Care Medicine, 1994, pp. 573-576; vol. 20.

Wilson et al., Increases in Endotracheal Tube Resistance Are Unpredictable Relative to Duration of Intubation. A study performed at West Virginia University, School of Medicine and West Virginia University Hospital, Morgantown, WV. Supported by Covidien Healthcare. Manuscript received Aug. 7, 2008.

Product brochure in 2 pages for GlideScope® Cobalt of Verathon Medical, Inc., dated 2010.

Product brochure in 2 pages for Rescue Cath™ Complete Airway Management (CAM) Catheters of Omneotech, dated 2010.

Glass, Connie et al., Endotracheal Tube Narrowing After Closed-System Suctioning: Prevalence and Risk Factors, American Journal of Critical Care, vol. 8, No. 2, pp. 93-100 (Mar. 1999).

Inglis, Timothy J.J. et al, Tracheal Tube Biofilm as a Source of Bacterial Colonization of the Lung, Journal of Clinical Microbiology, vol. 27, No. 9, pp. 2014-2018 (Sep. 1989).

Kawati, Rafael MD et al, Peak Airway Pressure Increase Is a Late Warning Sign of Partial Endotracheal Tube Obstruction Whereas Change in Expiratory Flow Is an Early Warning Sign, Anesth Analg., vol. 100, pp. 889-893 (2005).

El-Khatib, M.F. et al., Changes in resistances of endotracheal tubes with reductions in the cross-sectional area, European Journal of Anaesthesiology, vol. 25, pp. 275-279 (2008).

Shah Chirag MD et al., Endotracheal tube intraluminal volume loss among mechanically ventilated patients. Crit. Care Med, vol. 32, No. 1, pp. 120-125 (2004).

Van Surell, Catherine et al., Acoustic Method to Estimate the Longitudinal Area Profile of Endotracheal Tubes, Am J Respir Crit Care Med, vol. 149, pp. 28-33 (1994).

Boque, MC et al. Endotracheal tube intraluminal diameter narrowing after mechanical ventilation: use of acoustic reflectometry, Intensive Care Med vol. 30, pp. 2204-2209 (2004).

Apostolopoulou, Eleni Ph.D. et al., Incidence and Risk Factors for Ventilator-Associated Pneumonia in 4 Multidisciplinary Intensive Care Units in Athens, Greece, Respiratory Care, vol. 48, No. 7, pp. 681-688 (Jul. 2003).

Seckel, Maureen, Implementing Evidence-Based Practice Guidelines to Minimize Ventilator-Associated Pneumonia (2005).

Berra, Lorenzo et al.; A clinical assessment of the Mucus Shaver; Crit Care Med 2012 vol. 40, No. 1; 7 pages.

Conti, Sep. 1994, Intensive Care Medicine, 20, pp. 573-576.

* cited by examiner

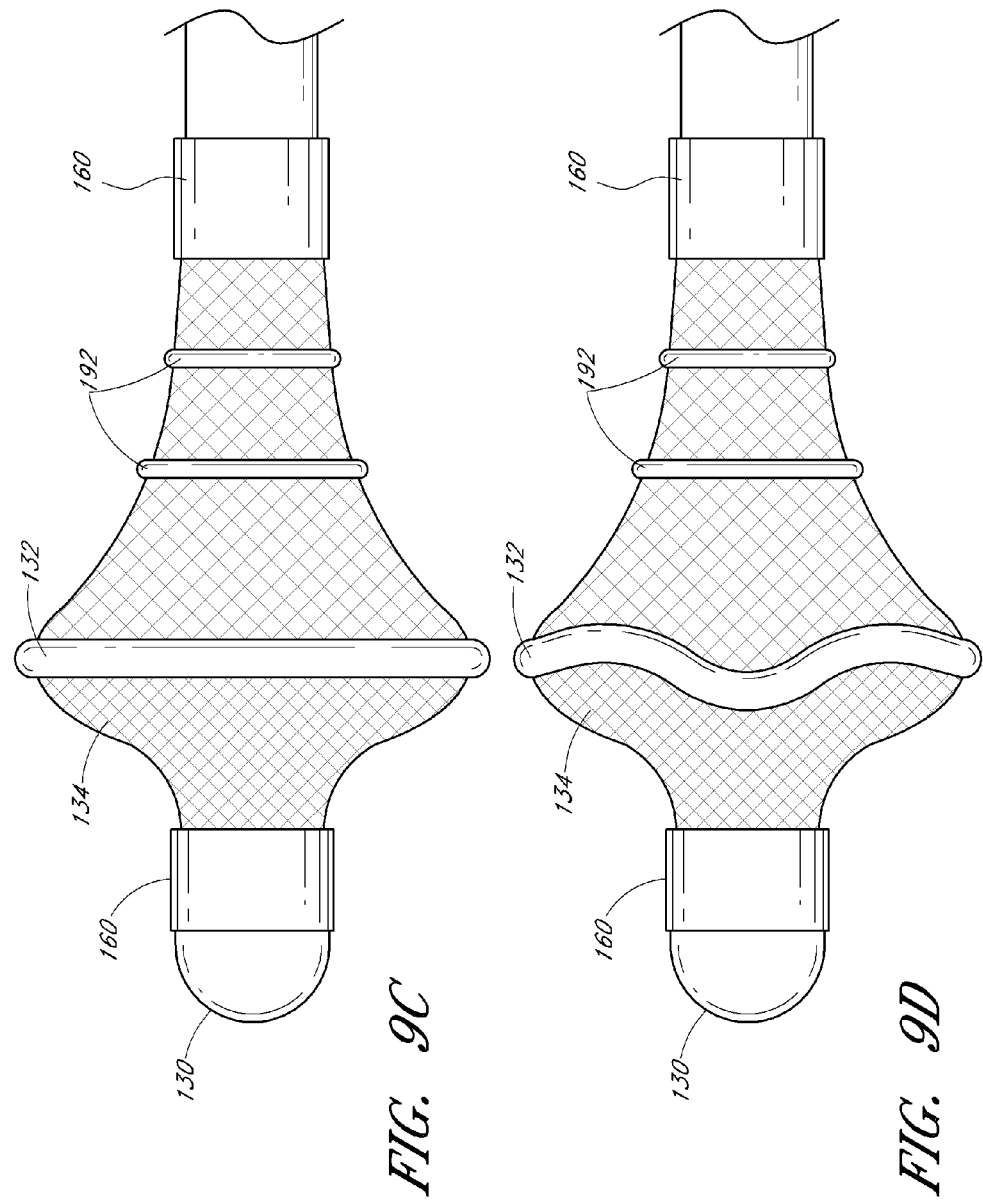

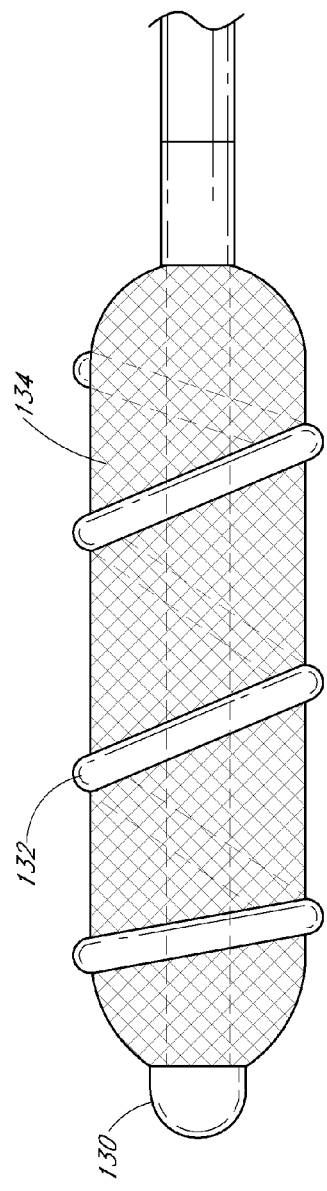
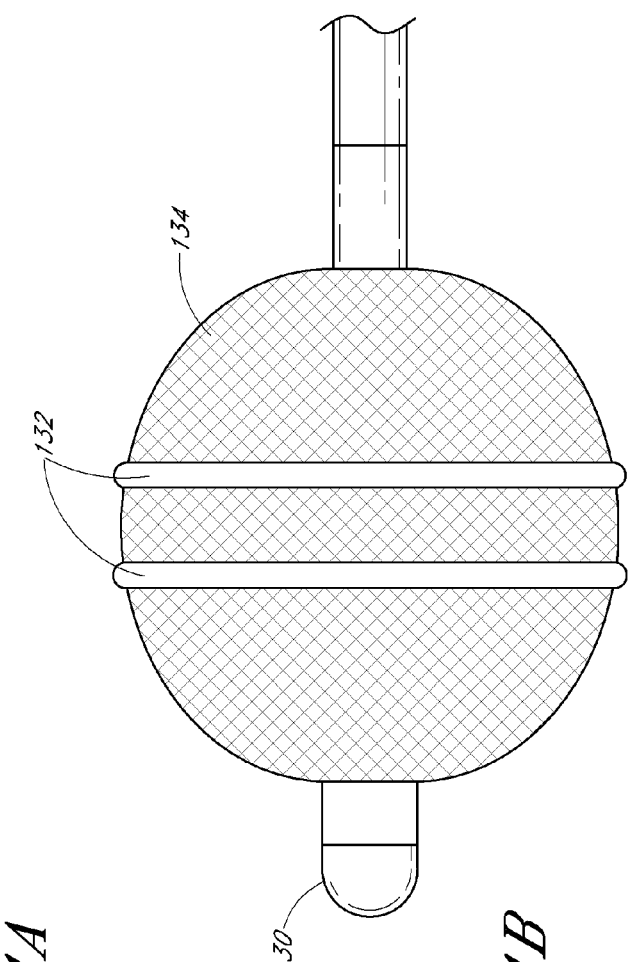
FIG. 11A
FIG. 11B

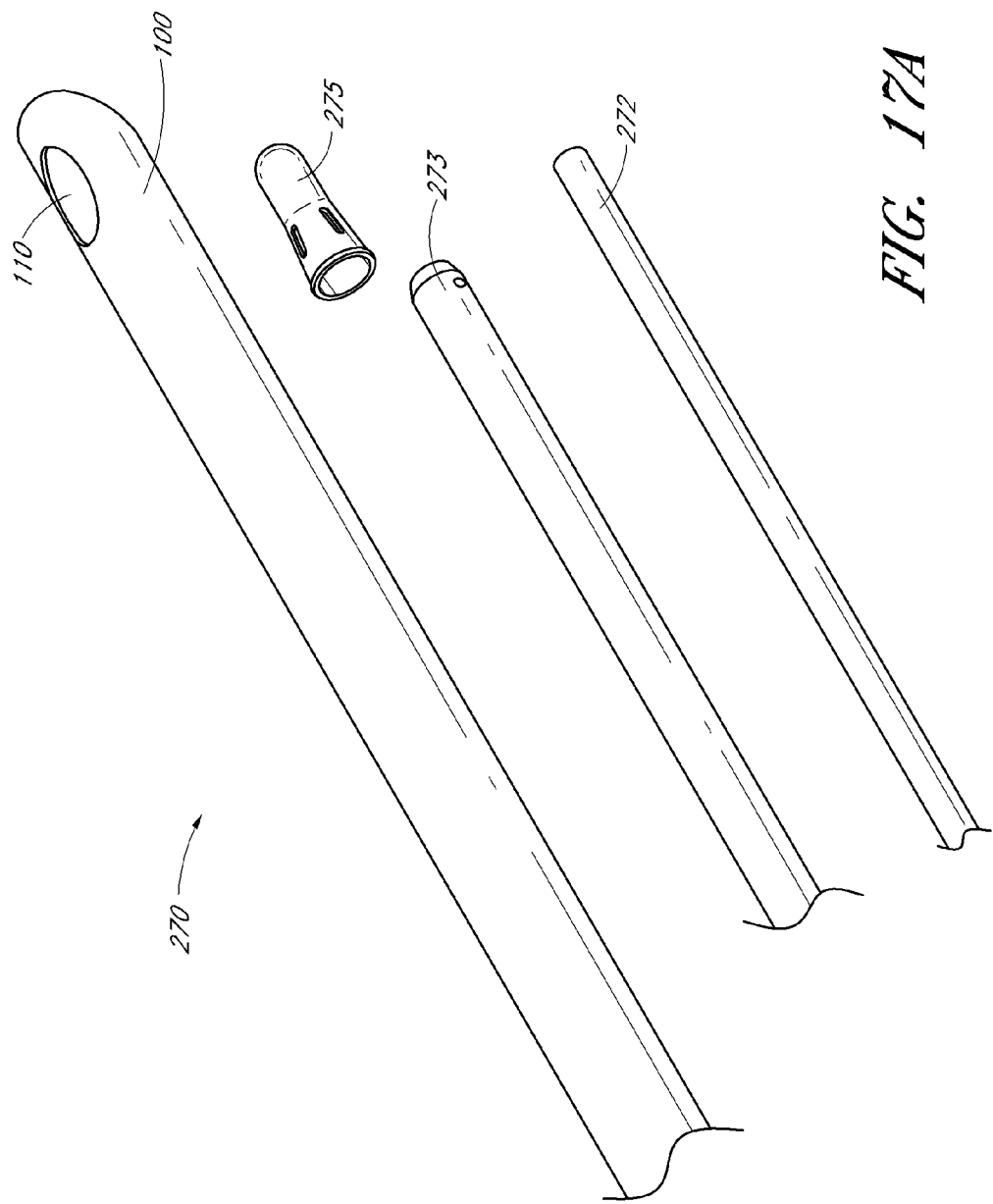

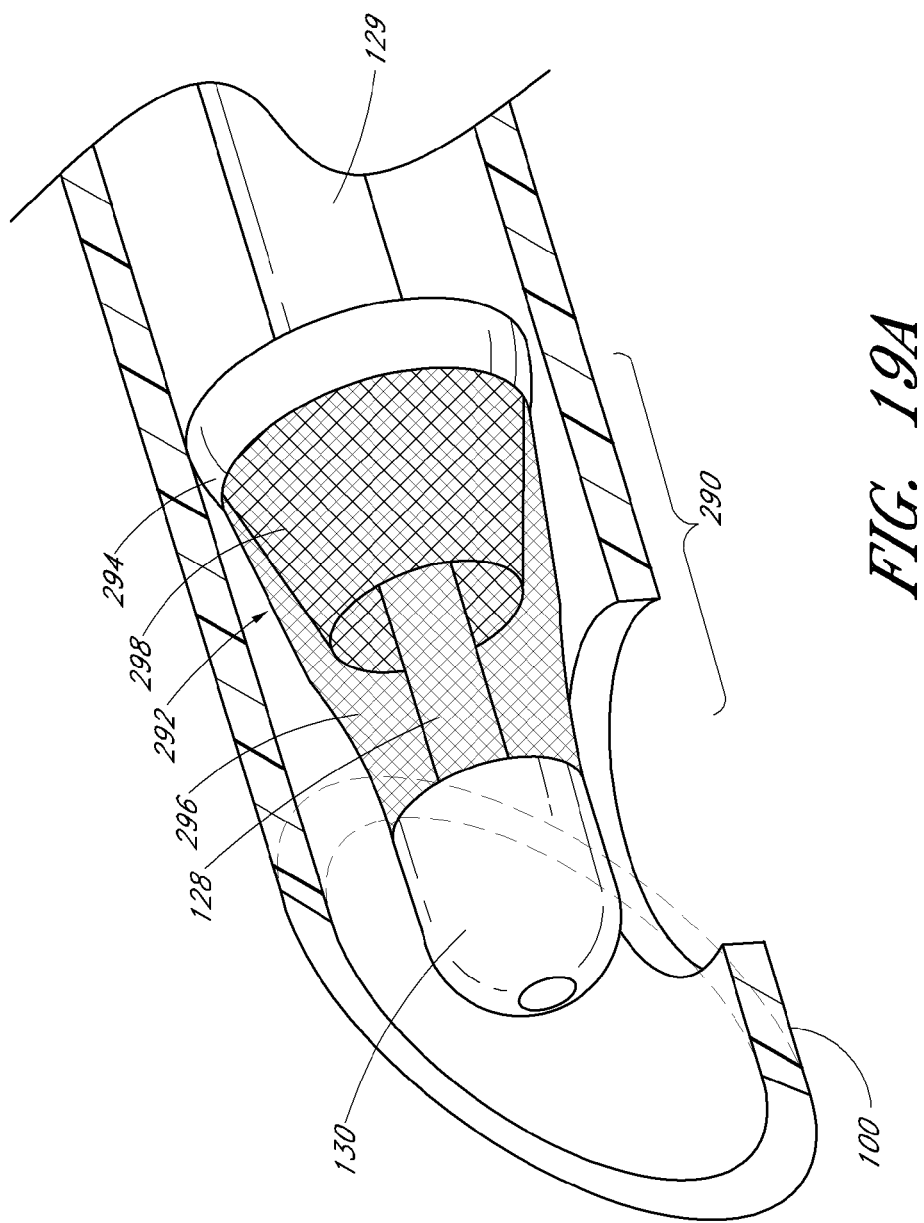

CLEANING OF BODY-INSERTED MEDICAL TUBES

CROSS REFERENCE TO RELATED APPLICATIONS

This application is a continuation of U.S. patent application Ser. No. 12/701,421, filed Feb. 5, 2010, now U.S. Pat. No. 8,382,908, which claims the priority benefit under 35 U.S.C. §119(e) of U.S. Provisional Application No. 61/150,456, filed Feb. 6, 2009, the entirety of which is hereby incorporated by reference herein.

BACKGROUND

1. Field

This application relates generally to the cleaning of body-inserted tubes and, more specifically, to devices, systems, and methods for removing fluids, secretions and/or other materials from a lumen of an endotracheal tube.

2. Description of the Related Art

An endotracheal tube is used in patient care to provide a clear airway through the mouth, pharynx, and trachea into the tracheobronchial tree. Use of an endotracheal tube is appropriate when the integrity of the airway is, or may become, challenged due to trauma or pathology, or if a patient cannot otherwise breathe unaided. Often the endotracheal tube is coupled to a mechanical ventilator to aid the patient's respiration, and can be expected to remain in situ for an extended time until the patient is once again able to breathe on his own.

Endotracheal tubes are used in millions of patients around the world to support life after major surgery, trauma, or the development of certain severe medical conditions such as pneumonia and sepsis. Patients with endotracheal tubes may be supported by the ventilator for days, weeks or months.

In certain circumstances, secretions and debris (biofilm) begin to accumulate on the inside wall of the endotracheal tubes shortly after (e.g., within 24 hours) of initial intubation. The biofilm can contain harmful bacteria (e.g., gram-negative organisms) that, if not removed in a timely and efficient manner, can be a potential nidus for infection. Endotracheal intubation is the single most important risk factor for hospital-acquired pneumonia. Intubated patients experience a much greater risk of developing hospital-acquired pneumonia than patients who are not ventilated. Further, ventilator-acquired pneumonia (VAP) is the leading cause of morbidity and mortality in the intensive care unit (ICU), and once present, can double the expected mortality for affected patients.

In certain circumstances, VAP significantly increases the cost of hospitalization. Tracheostomy can further increase the cost of dealing with such conditions. As these are typically classified as hospital-acquired infections, health insurance providers may stop reimbursement for VAP. Because VAP is so prevalent for intubated patients, this could vastly increase the cost to health care providers.

SUMMARY

There remains a need for systems, methods and devices for the cleaning of endotracheal tubes that are effective and efficient so that the tube cleanings can be reasonably carried out on a regular and preventative basis, rather than only when a particular problem arises. There also remains a need for systems, methods and devices for the cleaning of endotracheal tubes that prevent the build up of materials, perform the cleaning quickly, and that permit sufficient airflow through the endotracheal tube during use.

Frequently, it is not practical or clinically acceptable to change out the endotracheal tube when there is a buildup of biofilm in order to remove the endotracheal tube for cleaning. Removal and reinsertion of the endotracheal tube can be uncomfortable for the patient, can cause injury to the native airway, and can put reliable control of the airway at risk. Thus, several embodiments of the invention permit the cleaning of an endotracheal tube without the need to remove the endotracheal tube from the patient.

Some embodiments of the invention are particularly advantageous because it avoids the need for "blind" suctioning of the biofilm with a suction catheter. Thus, in several embodiments, the invention minimizes patient discomfort and avoids long periods of breathing interruption.

Some embodiments of the invention are advantageous because they do not employ a balloon or other seal as a cleaning member. Thus, in some embodiments, the invention facilitates airflow through the endotracheal tube during cleaning. In addition, problems associated with rupture of the balloon or the inability to adequately deflate the balloon are avoided in some embodiments. In some embodiments, the invention comprises a cleaning device that can be operated by a single user. In one embodiment, the invention comprises a cleaning device that can be operated by a single user using one hand. Thus, several embodiments are particularly advantageous because of the simplicity of one-handed operation and the reduced time needed for mechanically actuating the device (as opposed to inflating a balloon). In one embodiment, the cleaning device does not require multiple passes to clean the endotracheal tube, although the device is suitable for repeated closure and expansion if desired.

In some embodiments, the cleaning device removes harmful bacteria from the endotracheal tube by removing biofilm. In several embodiments, the cleaning device comprises a scaffold (e.g., mesh scaffold), or other collection member, for trapping the harmful biofilm, thereby reducing the vaporization or travel of harmful bacteria during the cleaning process.

In some embodiments, the removal of biofilm not only removes a source of harmful bacteria, but also enhances airflow and respiration. Biofilm can accumulate over time to a level that impairs ventilation by significantly reducing the cross-sectional area of the lumen of the endotracheal tube. For example, a 1 mm thick layer of biofilm in an endotracheal tube having an 8 mm inside diameter can reduce the cross-sectional area available for air flow by approximately 50%. Progressive airway occlusion within the endotracheal tube can make weaning and extubating the patient difficult or impossible, and may lead to the need for a tracheostomy.

In several embodiments, the devices described herein are inserted to a variable, predetermined depth inside the endotracheal tube and when the cleaning member is deployed to engage the inner surface of the endotracheal tube, air exchange through the deployed cleaning member can still occur. In some embodiments, the endotracheal tube cleaning device has a lockable, adjustable insertion stop that prevents the device from being inserted too far into the patient's ET tube, thereby avoiding potential injury to the patient's airway.

In some embodiments, the endotracheal tube cleaning devices described herein can accommodate a viewing element in an internal channel or lumen for training purposes, to assess the inside surface of an endotracheal tube, and/or to determine the position of the tip of the endotracheal tube in relation to the patient's carina.

In some embodiments, the endotracheal tube cleaning devices have a simple expansion mechanism and can be manufactured from inexpensive and/or disposable materials to keep costs low. By reducing patient care costs, the endotracheal tube cleaning device can be used on a regular and preventative basis and not just when trouble arises.

A cleaning device according to some embodiments of the invention has a cleaning member that can be rapidly deployed, the tube cleaned of build up, and the cleaning device removed in a manner such that the patient can continue to be supported by a ventilator with only the briefest interruption.

According to some embodiments, a mechanically-actuated non-inflatable cleaning device for scraping debris (e.g., biofilm) from an interior wall of a conduit is provided. In one embodiment, the cleaning device comprises an elongated member having a proximal end and a distal end and a mechanically-expandable scaffold (e.g., mesh scaffold, struts, etc.) positioned along the distal end of the elongated member. The mechanically-expandable scaffold is adapted to move between a radially-collapsed position and a radially-expanded position. Further, in one embodiment, the scaffold comprises one or more removal members (e.g., O-ring, wiper, piston ring, etc.) extending outwardly (e.g., radially) from an outer surface of the scaffold. In some embodiments, the removal member is configured to engage an interior surface of a conduit when the scaffold is in the radially-expanded position. In other embodiments, expansion of the scaffold can be configured so that the removal member does not contact the inside surface of the conduit. In other embodiments, the expansion and collapse of the scaffold can be selectively regulated to easily modify the radial expansion of the removal member coupled to the scaffold. In some embodiments, the removal member is configured to scrape, shear, dislodge, loosen or otherwise remove debris collected on an interior surface of the conduit when said cleaning device is moved relative to the conduit. In several embodiments, the scaffold comprises pores (e.g., mesh structure), other orifices or openings and/or the like that are configured to trap the scraped debris. The cleaning device additionally includes an actuation assembly coupled to the proximal end of the elongated member. In some embodiments, the scaffold is configured to move between the radially-collapsed position and the radially-expanded position (e.g., a fully radially-collapsed position, a fully radially-expanded position, a partially radially-collapsed position, a partially radially-expanded position, etc.) by manipulation of the actuation assembly (e.g., trigger, handle, lever, etc.). In some embodiments, the expansion and collapse of the scaffold occurs mechanically. In some embodiments, the actuation assembly provides single action expansion and single action collapse of the scaffold.

In one embodiment, the removal member (e.g., one or more O-rings, wipers, etc.), scaffold (e.g., mesh scaffold), struts, ribs, the collection member and/or any other portion of the cleaning device or system are configured to be actively mechanically actuated between an expanded configuration and a collapsed configuration. In some embodiments, the removal member, scaffold, struts, ribs, the collection member and/or any other portion of the cleaning device or system are actively mechanically actuated without the use of a sheath, sleeve, covering or similar member. In another embodiment, the removal member, scaffold, struts, ribs, the collection member and/or any other portion of the cleaning device or system are non-bristled, non-inflatable and/or non-sheathed.

According to some embodiments, a non-inflatable, mechanically-actuated cleaning device for removing biofilm from an interior wall of an endotracheal tube or other conduit comprises an elongate body having a distal end, a proximal end, a longitudinal axis and a diameter in the range of about 1 mm to about 5 mm. The cleaning device further comprises a scaffold (e.g., mesh scaffold) positioned at the distal end of the elongate body. In some embodiments, the scaffold is positioned near the proximal end of the elongate body or at any other location along the elongate body. In one embodiment, the cleaning device comprises one or more O-rings or other removal members coupled to the scaffold (e.g., mesh scaffold) and a non-inflatable actuation assembly coupled to the proximal end of the elongate body for mechanically-actuating the expansion of the scaffold. In some embodiments, the scaffold is radially expandable between a collapsed position and an expanded position by manipulation of the actuation assembly. In one embodiment, the level of expansion and/or collapse can be precisely controlled between fully-expanded and fully-collapsed positions. In several embodiments, the O-ring or other removal member is configured to engage an interior surface of an endotracheal tube when the scaffold is in the expanded position. In some embodiments, the O-ring is configured to remove biofilm collected on the interior surface of an endotracheal tube when said O-ring is moved along the longitudinal axis of the elongate body. In one embodiment, the scaffold comprises a porous architecture configured for facilitating the in-flow of said biofilm into an interior of the scaffold, thereby trapping at least a portion of the biofilm within the scaffold. In other embodiments, one or more portions of the scaffold are non-porous or substantially non-porous so as to prevent or reduce the likelihood of biofilm and/or other materials from passing therethrough. In several embodiments, the scaffold (e.g., mesh scaffold) is configured to allow airflow through the endotracheal tube in the collapsed position and the expanded position. In some embodiments, the actuation assembly is configured for one-handed manipulation of the cleaning device during a cleaning procedure.

In some embodiments, the conduit to be cleaned is a gun barrel, and the cleaning device or system comprises one or more removal members that are configured to remove oil, grease, oxidation, rust, mineral deposits, scale, other types of deposits, gun powder residue, other types of combustion residue and/or the like. In other embodiments, the conduit to be cleaned is a pipe, duct, flue (e.g., boiler flue), exhaust conduit or tubing, and the cleaning device or system comprises one or more removal members that are configured to remove sludge, mineral deposits, rust, other oxidation, grease, oil, soot, biofilm, scum, scale and/or the like.

According to some embodiments, a non-inflatable, mechanically-actuated cleaning device for removing biofilm from an interior wall of an endotracheal tube comprises an elongate body having a distal end, a proximal end and a longitudinal axis, and a cleaning member positioned at or near the distal end of the elongate body. In some embodiments, the cleaning member is positioned near the proximal end of the elongate body, generally between the distal and proximal ends of the elongate body and/or at any other location along the elongate body. In one embodiment, the distal end of the elongate body comprises a tip. In some embodiments, the cleaning member comprises a removal member and a collection member, such that the removal member is selectively movable between a radially-collapsed position and a radially-expanded position. In several embodiments, the removal member is configured to engage an interior surface of an endotracheal tube when in the radially-expanded position. In other embodiments, the removal member is configured to engage at least a portion of a biofilm layer positioned along the interior surface of an endotracheal tube when in the radially-expanded position. In some embodiments, the removal member is configured to be expanded to any one of a plurality of possible expanded positions. In one embodiment, the possible expanded positions for the removal member are generally between a fully collapsed and a fully expanded position.

According to several embodiments, the removal member is configured to remove biofilm collected on the interior surface of an endotracheal tube when the removal member is moved along the longitudinal axis of the elongate body. In other embodiments, the removal member is configured to remove biofilm when it is moved relative to the endotracheal tube. In some embodiments, the non-inflatable, mechanically-actuated cleaning device further comprises one or more collection members configured to collect at least a portion of removed biofilm. In several embodiments, the collection member is configured to allow airflow through the endotracheal tube. In other embodiments, the cleaning device additionally comprises a non-inflatable actuation assembly coupled to the elongate body. In one embodiment, the actuation assembly is located at or near the proximal end of the elongate body. According to some embodiments, the removal member is movable between the radially-collapsed position and the radially-expanded position by manipulation of the actuation assembly. In another embodiment, the expansion and collapse of the removal member occurs mechanically and not using inflation balloons and/or other hydraulic devices or features.

In some embodiments, the outside diameter of the elongate body of the cleaning device is about 0.05 mm to about 10 mm (e.g., from about 1 mm to about 5 mm, about 2 mm to about 4.5 mm, about 2.5 mm to about 3.5 mm, about 5 mm to about 8 mm, about 8 mm to about 10 mm, or greater, and overlapping ranges thereof). In some embodiments, the length of the elongate body is about 10 cm to about 70 cm, or greater, (e.g., from about 10 cm to about 20 cm, about 20 cm to about 30 cm, about 30 cm to about 40 cm, about 40 cm to about 50 cm, about 50 cm to about 70 cm, and overlapping ranges thereof). In one embodiment, the length of the elongate body is about 29 cm to about 45 cm.

In some embodiments, the cleaning member is positioned at, near or proximate to the distal end of the elongate body. In other embodiments, the cleaning member is positioned anywhere along the elongate body. In several embodiments, the collection member comprises an expandable scaffold configured to expand the removal member into the radially-expanded position. According to some embodiments, the collection member comprises a mesh or another member having a plurality of pores, orifices or other openings. In some embodiments, the actuation assembly is configured to permit a user to modify radial expansion of the removal member in order to modify a pressure exerted by the removal member on an inside surface of an endotracheal tube or on a biofilm deposited thereon. In one embodiment, the expansion of the removal member can be varied along a spectrum or range generally defined between a fully-collapsed positioned and a fully-expanded position.

According to some embodiments, the non-inflatable, mechanically-actuated cleaning device for removing biofilm from an interior wall of an endotracheal tube includes a cleaning device having an elongate body which comprises an inner shaft and an outer shaft, such that movement of the inner shaft relative to the outer shaft causes the removal member to move between collapsed and expanded radial positions. In some embodiments, the removal member is moved between a radially-collapsed position and a radially-expanded position by deployment of at least one strut or similar member located at or near the cleaning member. In other embodiments, the removal member of the cleaning device comprises one or more expandable wiper members.

According to some embodiments, the cleaning member of the cleaning device comprises an expandable spring or an expandable collet. In several embodiments, the removal member comprises a generally smooth outer surface. In other embodiments, the elongate body of the cleaning device comprises at least one interior lumen that extends at least partially along the length of the elongate body. In some embodiments, the cleaning device additionally comprises one or more ports in the elongate body and/or the actuation assembly that provides access to the interior lumen of the elongate body.

In some embodiments, the distal tip of the elongate body comprises a viewing window or other feature or portion through which visualization can occur. In one embodiment, the elongate body of the cleaning device comprises one or more interior lumens, channels or other openings to provide access to a location along an exterior of the elongate body. In other embodiments, the removal member can have one or more openings that provide access to a location along an exterior of the cleaning device. In some embodiments, the openings along the elongate body and/or the removal member allow for the aspiration and/or irrigation of fluids or other materials. In several embodiments, an interior lumen or other opening of the elongate body is configured to receive at least one of a visualization scope, an aspiration conduit, an irrigation conduit, a light therapy source or a ventilation conduit. In some embodiments, catheters or other instruments configured to be positioned through one or more lumens of the elongate body or other portion of the cleaning device comprise ultrasonic catheters, radio frequency (RF) catheters, irrigation catheters, aspiration catheters, drug delivery catheters, catheters for delivering light for photodynamic or other light-based therapy, other types of catheters or devices, and/or combinations thereof. In one embodiment, the elongate body comprises one or more openings at or near the distal tip. In other embodiments, the elongate body comprises one or more openings near its proximal end and/or at any other location along the length of the elongate body.

According to some embodiments, the actuation assembly is configured for one-handed manipulation of the cleaning device during a cleaning procedure. In other embodiments, the cleaning device is configured for single pass cleaning. In other embodiments, the cleaning device is configured for multiple pass cleaning. In certain embodiments, the cleaning device is used to clean endotracheal tubes having a variety of diameters and lengths. In some embodiments, the removal member is positioned along an exterior surface of the collection member. In one embodiment, the removal member is positioned, at least partially, along an interior portion of the collection member.

In other embodiments, the removal member generally divides the collection member into a first portion and a second portion, such that the first portion is situated at a location proximal to the removal member and the second portion is situated at a location distal to the removal member. In some embodiments, the first portion is configured to generally allow biofilm to pass therethrough and the second portion is configured to generally prevent biofilm from passing therethrough, such that biofilm is collected and trapped within a cavity of the collection member as the cleaning device is moved relative to an endotracheal tube. In some embodiments, the first portion comprises a plurality of pores or openings that are larger in cross-sectional shape than second pores or openings of the second portion.

According to some embodiments, the removal member is positioned along an exterior surface of the collection member so as to generally divide the collection member into a first portion and a second portion. The first portion is situated proximal to the removal member and the second portion is situated distal to the removal member. In one embodiment, the first and second portions form a generally convex, concave or any other shape when the removal member is in a radially expanded position. According to some embodiments, the removal member and the collection member are separate items that are permanently or removably attached to each other. In other embodiments, the removal member and the collection member are integrally formed as part of a unitary structure.

According to several embodiments, a cleaning system for clearing debris from an interior wall of a medical tube (e.g., endotracheal tube, catheters, probes, body lumens, arteries, veins, other vasculature, grafts, aspiration conduits, ventilation tubes, etc.) includes an elongated member having a proximal end and a tip along its distal end. In one embodiment, the elongated member comprises one or more lumens or other channels extending within its interior. In some embodiments, the cleaning system additionally comprises a mechanically-expandable scaffold positioned along the elongated member. In one embodiment, the scaffold is adapted to be selectively moved between a radially-collapsed position and a radially-expanded position. In several embodiments, the scaffold is moved between fully-expanded and fully collapsed radial positions. In other embodiments, the scaffold is configured to be moved to any partially-expanded or partially-collapsed position that is generally between the fully-expanded and fully-collapsed radial positions. In some embodiments, the scaffold is configured to be moved between the radially-collapsed position and the radially expanded-position using one or more self-expanding members, expanding members releasably positioned within a sheath, umbrella-type members and/or the like.

In some embodiments, the scaffold (e.g., mesh scaffold) comprises one or more removal members (e.g., O-rings, wipers, squeegees, piston rings, etc.) extending outwardly (e.g., radially) from an outer surface of the scaffold. In other embodiments, the removal member is at least partially positioned within or through the scaffold. In several embodiments, the removal member is configured to engage an interior surface of a medical tube and/or at least a portion of the biofilm situated within the medical tube when the scaffold is in the radially-expanded position. In another embodiment, the removal member is configured to contact and remove debris collected on an interior surface of a medical tube when the mechanically-expandable scaffold is moved relative to the medical tube. The cleaning system additionally comprises an actuation assembly coupled to the proximal end of the elongated member. In some embodiments, the scaffold (e.g., mesh scaffold) is configured to move between the radially-collapsed position and the radially expanded-position by manipulation of the actuation assembly (e.g., trigger, handle, other mechanical actuator, button, other controller, etc.). In some embodiments, expansion and collapse of the scaffold occurs mechanically and not hydraulically (e.g., without the use of a balloon or other inflatable member).

In several embodiments, the cleaning system further comprises a visualization element configured for insertion into a lumen of the elongated member for visualizing the interior of the medical tube.

According to some embodiments, the cleaning system comprises a collection member configured to collect at least a portion of removed biofilm. In one embodiment, the scaffold comprises at least one layer of mesh. In some embodiments, the scaffold comprises one or more struts, ribs and/or other members that are configured to be selectively moved. In some embodiments, the scaffold comprises an umbrella-type structure. In some embodiments, the actuation assembly is configured to permit a user to selectively expand or collapse the scaffold in order to modify a pressure exerted by the at least one removal member on an inside surface of an endotracheal tube. In several embodiments, the elongated member comprises an inner shaft and an outer shaft, such that movement of the inner shaft relative to the outer shaft causes the scaffold to move between radially collapsed and expanded positions.

In some embodiments, the removal member comprises one or more O-rings. In some embodiments, the O-ring has a partial or full circular, oval, X-shaped, rounded, curvate, or irregular shape, or combinations thereof. Other suitable shapes may also be used as desired and/or required. In one embodiment, the removal member comprises one or more rounded portions or sections. In several embodiments, the removal member comprises one or more flat, sharp-edged or cornered portions or sections. In yet other embodiments, the removal member comprises both rounded and flat or cornered portions or sections. In certain embodiments, the removal member comprises one or more wipers. In some embodiments, the removal member comprises one or more squeegees. In other embodiments, the removal member comprises one or more blades, sharp edges, blades and/or the any other type of edge or surface. In several embodiments, the removal member comprises a helical spring, another type of coiled spring and/or another type of resilient member. In one embodiment, the removal member comprises a spring or other resilient member that normally moves from a radially-collapsed position to a radially-expanded position when forces are exerted on it. In other embodiments, the removal member comprises a spring or other resilient member that normally moves from a radially-expanded position to a radially-collapsed position when forces are exerted on it. In other embodiments, the scaffold comprises an expandable spring or an expandable collet.

According to several embodiments, the cleaning system further includes one or more ports in the elongated member, the actuation assembly and/or any other location. In some embodiments, the port provides access to the interior lumen of the elongated member. In other embodiments, the tip of the elongated member comprises a viewing window, viewing strip, viewing region, other transparent or translucent region and/or the like. In other embodiments, the elongated member comprises at least one lumen or other opening to provide access to a location along an exterior of the cleaning device. In one embodiment, the actuation assembly is configured for one-handed manipulation of the cleaning system during a cleaning procedure. In other embodiments, the cleaning device is configured for single pass cleaning. In some embodiments, the cleaning system is suitable for use with endotracheal tubes of varying diameters and lengths.

Several embodiments of the invention comprise a method of removing debris from the inside of a conduit. In some embodiments, the conduit is a medical tube. In some embodiments, the conduit is an endotracheal tube. According to some embodiments, methods for removing biofilm from an interior wall of an endotracheal tube or other conduit using the cleaning devices described herein are provided.

In one embodiment, the method comprises providing a non-inflatable, mechanically-actuated cleaning device configured to remove biofilm from an interior wall of an endotracheal tube and/or the vicinity thereof. In several embodiments, the endotracheal tube is inserted into the native airway of a patient and coupled to an external ventilator. In some embodiments, the cleaning device is not balloon inflatable. In several embodiments, the cleaning device comprises an elongate body, a mesh scaffold or other type of scaffold, one or more removal members and an actuation assembly. In one embodiment, the elongate body comprises a distal end, a proximal end and a longitudinal axis. In some embodiments, the scaffold is positioned at the distal end of the elongate body. In one embodiment, the scaffold is positioned at or near a tip of the elongate body. In other embodiments, the scaffold is positioned at any along the elongate body. In some embodiments, the removal member is coupled to the scaffold. In several embodiments, the removal member is a separate member from the scaffold that is permanently or removably attached to the scaffold. In other embodiments, the removal member and the mesh are integrally formed as a unitary structure.

According to several embodiments, the method additionally comprises decoupling the endotracheal tube from an external ventilator, inserting the distal end of the cleaning device into the endotracheal tube while the scaffold is in a collapsed position and mechanically actuating the mesh scaffold using the actuation assembly to expand the mesh scaffold from the collapsed position to an expanded position, thereby expanding the removal member to contact the biofilm and/or an inside surface of the endotracheal tube. The method further comprises withdrawing the cleaning device from the endotracheal tube while maintaining contact between the removal member and the biofilm and/or an interior surface of the endotracheal tube in order to dislodge at least a portion of biofilm. In some embodiments, the method further comprises collecting some or all of the dislodged biofilm within the mesh scaffold and removing the cleaning device from the patient. In several embodiments, the method additionally comprises coupling the endotracheal tube to the external ventilator.

According to some embodiments, the removal member of the cleaning device used in the biofilm removal method comprises a smooth outer periphery. In some embodiments, the removal member comprises a blunt outer surface. In other embodiments, the removal member comprises a non-smooth and/or a non-blunt outer periphery or surface. In some embodiments, the cleaning device comprises two or more removal members. In another embodiment, the removal member comprises one or more O-rings. In some embodiments, the O-ring has a circular, oval, X-shaped, rounded, curvate, irregular and/or any other shape, or a portion thereof. In another embodiment, the removal member comprises one or more rounded portions or sections. In other embodiments, the removal member comprises one or more flat, sharp-edged or cornered portions or sections. In yet other embodiments, the removal member comprises both rounded and flat or cornered portions or sections. In certain embodiments, the removal member comprises one or more wipers. In some embodiments, the removal member comprises one or more squeegees. In other embodiments, the removal member comprises one or more blades, sharp edges, blades and/or the any other type of edge or surface. In several embodiments, the removal member comprises a helical spring, another type of coiled spring and/or another type of resilient member. In one embodiment, the removal member comprises a spring or other resilient member that normally moves from a radially-collapsed position to a radially-expanded position when forces are exerted on it. In other embodiments, the removal member comprises a spring or other resilient member that normally moves from a radially-expanded position to a radially-collapsed position when forces are exerted on it.

According to some embodiments, the one or more removal members are coupled to the scaffold using one or more adhesives, stitches, welds, hot melt connections, braided connections, fasteners and/or any other attachment method or device. In some embodiments, the removal member is positioned, at least partially, along the outside of the scaffold. In other embodiments, the removal member is positioned, at least partially, within the interior of the scaffold member and/or through the scaffold member. In yet other embodiments, the removal member is routed through exterior and interior portions or sections of the scaffold. According to some embodiments, the removal member is positioned along a single plane or generally within a single plane that is generally perpendicular to the longitudinal axis of the elongate body. In other embodiments, the removal member comprises a sinusoidal, undulating, curvy, curly and/or wavy shape or design. In some embodiments, the removal member comprises one or more elastomeric and/or polymeric materials. In other embodiments, the removal member comprises a metal, an alloy and/or any other rigid, semi-rigid and/or flexible material.

According to several embodiments, the scaffold of the cleaning device is configured to allow airflow through the endotracheal tube while the scaffold is in an expanded position. In some embodiments, the scaffold of the cleaning device is configured to allow airflow through the endotracheal tube regardless if the scaffold is in a collapsed or expanded position. In one embodiment, the scaffold of the cleaning device comprises mesh, one or more pores, orifices and/or other openings through which air or other fluids can pass. In some embodiments, the actuation assembly of the cleaning device is configured for one-handed manipulation of the cleaning device during a cleaning procedure. In other embodiments, the actuation assembly of the cleaning device is configured for two-handed manipulation of the cleaning device during a cleaning procedure. In one embodiment, the biofilm removal method comprises only a single pass of the cleaning device through the interior of the endotracheal tube to achieve an adequate level of cleaning. In other embodiments, the cleaning device is configured for repeated expansion and collapse of the scaffold and the removal member, thereby allowing the same cleaning device to be used more than once during a biofilm removal method or procedure.

According to several embodiments, the scaffold comprises a porous architecture configured to facilitate the collection of biofilm, debris and/or other materials present within or near the interior of an endotracheal tube. In some embodiments, the scaffold comprises a mesh scaffold. In other embodiments, the scaffold comprises a first section that generally permits biofilm to pass therethrough and a second section that generally prevents biofilm from passing therethrough. In one embodiment, the scaffold of the cleaning device includes an interior cavity or region into which the removed biofilm and/or other materials are collected and trapped. In some embodiments, the mesh size, pore size or opening size of the first section of the scaffold is generally greater than that of the second section.

According to some embodiments, the method of removing biofilm from an endotracheal tube additionally includes providing a visualization element or device for viewing at least a portion of the interior wall of the endotracheal tube, a patient's trachea, tracheobronchial tree and/or any other portion within a patient's anatomy. In one embodiment, the visualization element comprises an endoscope, a boreoscope, another type of visualization scope and/or any type of viewing element configured to provide visual feedback to a clinician during a biofilm removal method or procedure. In several embodiments, the visualization element is inserted through a lumen of the elongate body. In some embodiments, the elongate body of the cleaning member comprises one, two or more lumens or channels through which a visualization element, another type of catheter or scope and/or other devices can be inserted.

In some embodiments, the method of removing biofilm from the inside of an endotracheal tube additionally comprises aspirating biofilm and/or other materials from an interior of the endotracheal tube using a suction catheter or other aspiration device. In one embodiment, aspiration of biofilm occurs prior to inserting the distal end of the cleaning device into the endotracheal tube. However, in other embodiments, aspiration of biofilm and/or other materials occurs while the cleaning device is being inserted into the endotracheal tube, while the endotracheal tube is being removed from the endotracheal tube, after the cleaning device has been removed from the endotracheal tube and/or combinations thereof.

According to several embodiments, the method of removing biofilm from an endotracheal tube further comprises irrigating at least a portion of the interior wall of the endotracheal tube with a drug, a medicament, a treatment fluid, another type of liquid, gas, other fluid, solid, gel, paste and/or other materials. In some embodiments, irrigation fluids and/or other materials are adapted to disinfect, decontaminate, sterilize and/or otherwise treat the endotracheal tube. In some embodiments, irrigation fluids and/or other materials are configured to loosen, break up, penetrate, degrade, disperse, dissolve and/or otherwise undermine or affect biofilm deposited on the inside wall or other surface of the endotracheal tube. In some embodiments, irrigation of the interior wall of the endotracheal tube is performed using one or more irrigation catheters or other devices inserted through a lumen or other channel of the elongate body. In other embodiments, irrigation comprises delivering a fluid and/or other substances through a catheter or other conduit that is not routed through an interior of the elongate body or the cleaning device.

In several embodiments, a method of removing biofilm from an endotracheal tube comprises the introduction of one or more diagnostic and/or therapeutic catheters or other instruments within one or more lumens or other channels of elongate body. In some embodiments, catheters or other instruments configured to be positioned through a lumen of the elongate body or other portion of the cleaning device comprise ultrasonic catheters, radio frequency (RF) catheters, irrigation catheters, aspiration catheters, drug delivery catheters, catheters for delivering light for photodynamic or other light-based therapy, other types of catheters or devices, and/or combinations thereof.

According to some embodiments, a method for cleaning an inside surface of an endotracheal tube without removing the endotracheal tube from a native airway of a patient comprises positioning the patient in a semi-upright position, delivering concentrated oxygen or oxygen-containing fluid through the endotracheal tube using a ventilator for a predetermined time period and aspirating an interior of the endotracheal tube using an aspiration instrument. In one embodiment, positioning the patient in a semi-upright position comprises elevating the head of the bed on which the patient is situated to at least approximately 20 to 40 degrees, (e.g., 30 degrees) relative to horizontal. In some embodiments, the concentrated oxygen or oxygen-containing fluid that is delivered to the patient comprises pure oxygen (e.g., 100% oxygen) or nearly 100% oxygen. In other embodiments, the concentration of oxygen in the fluid delivered through the endotracheal tube is less than 100% oxygen, e.g., 95-100%, 90-95%, 80-90%, 70-80% oxygen, air comprising less than 70% oxygen and/or the like. In some embodiments, the oxygen or oxygen containing fluid is delivered to the patient for about 10 minutes. In other embodiments, oxygen or oxygen containing fluid is delivered to the patient for less than about 10 minutes or longer than about 10 minutes.

In some embodiments, a method for cleaning an inside surface of an endotracheal tube without removing the endotracheal tube from a native airway of a patient additionally includes providing an endotracheal tube cleaning device having a radially expandable cleaning member. According to several embodiments, the cleaning member comprises a removal member. In several embodiments, the method additionally comprises determining a deployment depth for the endotracheal tube cleaning device based at least in part on the length of the endotracheal tube and locking a movable stop on the endotracheal tube cleaning device at an axial position that causes deployment of the cleaning member at the determined deployment location. In some embodiments, the method for cleaning an endotracheal tube comprises disconnecting the ventilator from the endotracheal tube.

According to several embodiments, the method for cleaning an inside surface of an endotracheal tube without removing the endotracheal tube from a native airway of a patient additionally comprises inserting the cleaning device into the endotracheal tube according to a determined deployment depth and mechanically actuating the cleaning member from a radially-collapsed position to a radially-expanded position by manipulating an actuation assembly of the endotracheal tube cleaning member. In some embodiments, mechanically actuating the cleaning member causes the removal member to engage an interior wall of the endotracheal tube and/or a biofilm layer or other debris located along the interior of the endotracheal tube. In certain embodiments, the method additionally includes withdrawing the cleaning device from the endotracheal tube so as to remove biofilm accumulated on the interior wall of the endotracheal tube. In one embodiment, the method additionally includes reconnecting the ventilator to the endotracheal tube after the cleaning device has been withdrawn or otherwise removed from the endotracheal tube.

In some embodiments, the removal member of the cleaning device comprises a smooth outer periphery or surface. In other embodiments, the removal member comprises a non-smooth outer periphery or surface. In one embodiment, the removal member comprises one or more O-rings, wipers, squeegees, piston rings, and/or other members. In other embodiments, the cleaning member comprises a mechanically-expandable mesh scaffold.

In other embodiments, a method for cleaning an inside surface of an endotracheal tube without removing the endotracheal tube from a native airway of a patient additionally includes providing a visualization element for viewing the interior wall of the endotracheal tube. In several embodiments, the method comprises the introduction of one or more diagnostic and/or therapeutic catheters or other instruments within one or more lumens or other channels of the cleaning member. In some embodiments, catheters or other instruments configured to be positioned through the cleaning member comprise ultrasonic catheters, radio frequency (RF) catheters, irrigation catheters, aspiration catheters, drug delivery catheters, catheters for delivering light for photodynamic or other light-based therapy, other types of catheters or devices, and/or combinations thereof.

According to some embodiments, a method for removing biofilm from an interior wall of an endotracheal tube comprises providing a non-inflatable, mechanically-actuated cleaning device configured to remove biofilm from an interior wall of an endotracheal tube. In one embodiment, the endotracheal tube is inserted into the native airway of a patient and coupled to an external ventilator. In several embodiments, the method comprises providing a visualization element for viewing the interior wall of the endotracheal tube. In some embodiments, the cleaning device comprises an elongate body, a scaffold (e.g., mesh scaffold), a removal member and an actuation assembly. In several embodiments, the elongate body comprises a distal end, a proximal end and a longitudinal axis. According to some embodiments, the scaffold is positioned at the distal end of the elongate body. However, in alternative embodiments, the scaffold is located along any other portion of the elongate body. In some embodiments, the removal member is coupled to the scaffold.

According to some embodiments, the method for removing biofilm from an interior wall of an endotracheal tube additionally comprises decoupling the endotracheal tube from the external ventilator, inserting the distal end of the cleaning device into the endotracheal tube while the scaffold is in a collapsed position, mechanically actuating the scaffold using the actuation assembly to expand the scaffold from the collapsed position to an expanded position, thereby expanding the removal member to contact the biofilm, and withdrawing the cleaning device from the endotracheal tube while maintaining contact between the removal member and the biofilm and/or the interior wall of the endotracheal tube to dislodge biofilm. In some embodiments, the method further comprises collecting at least a portion of the dislodged biofilm within the scaffold. In one embodiment, collection of dislodged biofilm comprises allowing biofilm to pass through a plurality of openings of the scaffold into an interior space of the scaffold, and preventing at least a portion of said biofilm from leaving the interior space of the scaffold. The method additionally comprises removing the cleaning device from the patient In some embodiments, the method for removing biofilm from an interior wall of an endotracheal tube additionally comprises coupling the endotracheal tube to the external ventilator. In one embodiment, the removal member comprises a smooth outer periphery. In alternative embodiments, the removal member comprises an outer surface or periphery that is generally blunt. In other embodiments, the removal member comprises a non-smooth outer periphery or surface. In several embodiments, the visualization element is provided through a lumen of the elongate body of the cleaning device. In one embodiment, the method additionally includes viewing the interior wall of the endotracheal tube during insertion and/or withdrawal removal of the cleaning device.

According to some embodiments, a method of manufacturing a device configured to remove biofilm and/or other materials from the interior of a conduit comprises providing an elongate tube, securing a mechanically-expandable scaffold on the elongate tube and mechanically coupling the scaffold to an actuation assembly. In some embodiments, the device comprises one or more removal members along a periphery or other surface of the scaffold. The removal members (e.g., O-rings, wipers, squeegees, piston rings, etc.) are configured to engage and remove biofilm and/or other materials collected within an interior wall of the conduit when the scaffold is in a radially expanded position and the device is withdrawn from the conduit. In some embodiments, the elongate tube and the removal member comprise one or more polymeric and/or elastomeric materials. In several embodiments, the removal member is coupled to the scaffold using adhesives, stitches, welds, hot melt connections, braided connections, fasteners and/or any other attachment method or device.

BRIEF DESCRIPTION OF THE DRAWINGS

FIGS. 9A-9D illustrate embodiments of a collection member having a convex distal section and a concave proximal section.

FIGS. 10A-10H and FIG. 11A illustrate various embodiments of a removal member of an endotracheal tube cleaning device.

FIG. 11B illustrates a cleaning member having multiple removal members.

FIGS. 17A and 17B illustrate an embodiment of a vented tube design

FIGS. 19A and 19B illustrate an embodiment of a mechanically-expandable cleaning member.

DETAILED DESCRIPTION

Figure 1:
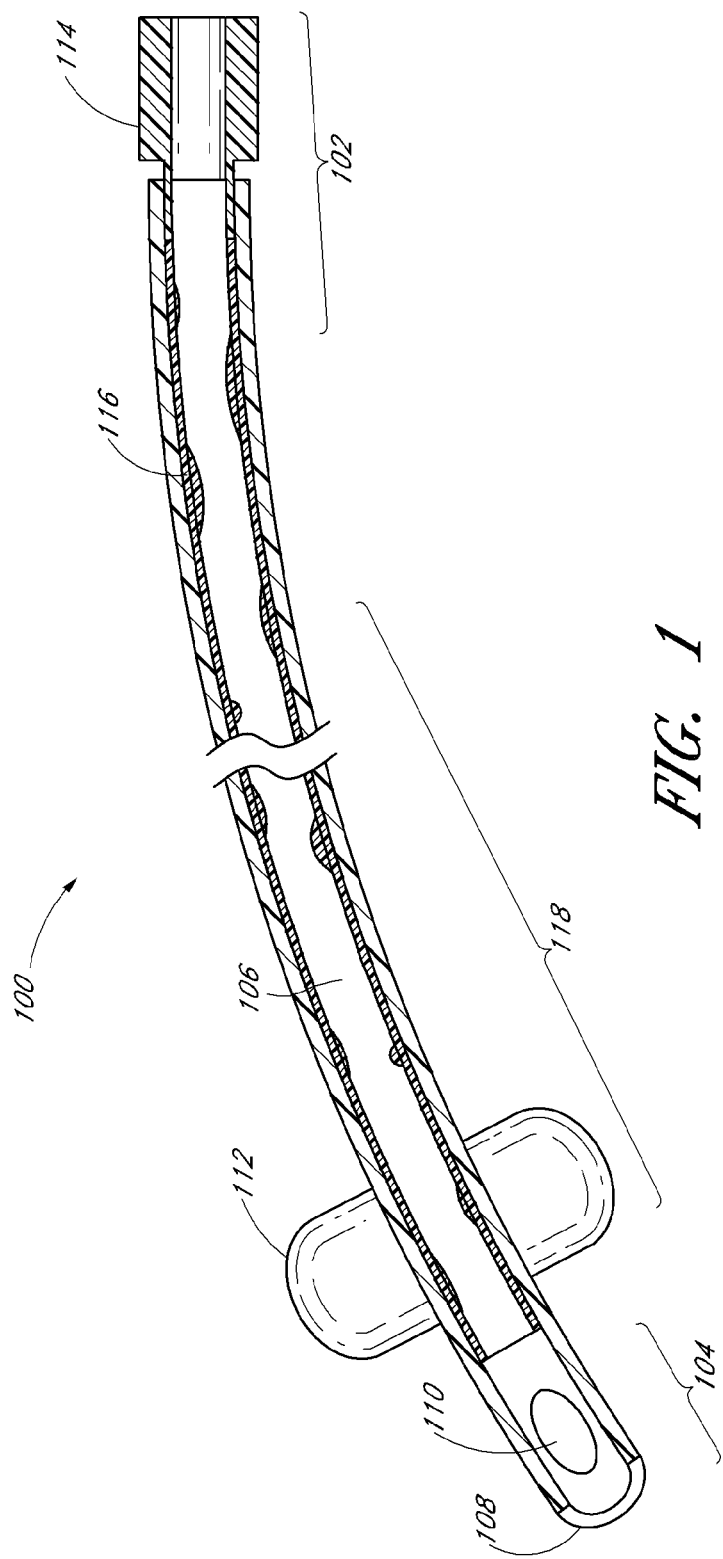
FIG. 1 illustrates a partial cross-sectional view of an endotracheal tube according to one embodiment.

The discussion and the figures illustrated and referenced herein describe various embodiments of a body-inserted tube cleaning system and device, as well as methods related thereto. A number of these embodiments of tube cleaning systems, devices and methods are particularly well suited to remove biofilm from an interior surface of an endotracheal tube. However, the various devices, systems, methods and other features of the embodiments disclosed herein may be utilized or applied to other types of apparatuses, systems, procedures, and/or methods, whether medically-related or not. For example, the embodiments disclosed herein can be utilized for, but are not limited to, cleaning bronchoscopes, chest drainage tubes, gastrostomy drainage tubes, abdominal drainage tubes, other body drainage tubes, feeding tubes, endoscopes, percutaneous dialysis catheters, and any other percutaneous or per os catheters or body-inserted tubes. In addition, as discussed in greater detail herein, the various embodiments disclosed herein can be used to clean conduits, such as, for example, pipes, tubing, guns, other barreled instruments, exhausts and/or other devices with lumens or other interior openings.

For example, in one embodiment, the conduit to be cleaned is a gun barrel, and the cleaning device or system is configured to remove oil, grease, oxidation, rust, mineral deposits, scale, other types of deposits, gun powder residue, other types of combustion residue and/or the like. In other embodiments, the conduit to be cleaned is a pipe, duct, flue (e.g., boiler flue), exhaust conduit or tubing, and the cleaning device or system is configured to remove sludge, mineral deposits, rust, other oxidation, grease, oil, soot, biofilm, scum, scale and/or the like.

The materials used for the various components of the endotracheal tube cleaning devices and systems described herein can advantageously comprise one or more biocompatible materials.

The term "biofilm" as used herein shall be given its ordinary meaning and shall include, without limitation, biological fluids, solids, gels, deposits, films, debris, and/or secretions, such as mucosal secretions, blood, bacteria, viruses, other microorganisms, protein, feces, urine, albumin and/or any other biological or biologically-related materials.

The term "scaffold" as used herein shall be given its ordinary meaning and shall include, without limitation, support members, collapsible members, expandable members, distensible members, solid structures, mesh structures, braided devices, porous structures, struts, polymeric structures, membranes, bladders, stents, umbrella-type devices, ribs, spokes, frames, and the like, and combinations thereof. Scaffolds may be fully or partially covered or may be uncovered. Covered scaffolds may comprise skeletons that are partially or fully covered by membranes, fabrics, films, multiple layers, and/or coated. Scaffolds may function as the cleaning member and/or may be used for supporting a cleaning member. Scaffolds can be mechanically actuated, self-actuated, inflated, and/or combinations thereof.

I. General System

A. Endotracheal Tube

FIG. 1 illustrates an example of an endotracheal tube 100 having a proximal end 102 and a distal end 104. The endotracheal tube 100 includes a hollow, central lumen 106 extending through the endotracheal tube 100 from the proximal end 102 to the distal end 104. In some embodiments, the endotracheal tube 100 includes a hole (not shown) at the tip 108 of its distal end 104 and a hole 110 on a side of the endotracheal tube 100 near the tip 108 of the distal end 104 known as a Murphy eye. In other embodiments, an endotracheal tube can include more or fewer holes or openings.

With continued reference to the embodiment illustrated in FIG. 1, the endotracheal tube 100 can include one or more balloon cuffs 112 at or near the distal end 104 of the endotracheal tube 100. The balloon cuff 112 is inflated during mechanical ventilation to prevent air leaks back around the endotracheal tube 100. In some embodiments, the proximal end 102 can include a coupling element 114 for connection with a mechanical ventilator. The inner diameter of the endotracheal tube 100 can range from about 1 mm to about 20 mm or from about 5 mm to about 10 mm. The length of the endotracheal tube 100 can range from about 10 cm to about 40 cm; however, endotracheal tubes of any length can be cleansed by the cleaning devices described herein. The endotracheal tube 100 can be manufactured to have a slight curve or pre-bend for facilitating insertion into a patient's native airway (e.g., trachea).

The endotracheal tube 100 can be configured to be inserted within a patient temporarily or permanently. In some embodiments, the endotracheal tube 100 is inserted within a patient orally or nasally via an intubation procedure. In other embodiments, the endotracheal tube 100 is inserted via a tracheotomy or tracheostomy procedure.

As shown in FIG. 1, biofilm 116 can build up on the interior surface of the endotracheal tube 100 over time. If not removed, biofilm 116 can restrict the airflow through the endotracheal tube 100. In addition, biofilm 116 can harbor harmful bacteria that can eventually lead to the development of pneumonia and/or other ailments or conditions. The layer of biofilm 116 on the interior surface of the endotracheal tube 100 can be substantially uniform or can vary substantially in thickness (e.g., peaks and valleys) along the length of the endotracheal tube 100.

The biofilm 116 can be present anywhere along the interior surface of the endotracheal tube 100. In some embodiments, the majority of the biofilm 116 collects in a main collection region 118 that extends from a point proximal to the Murphy eye 110 (e.g., about 2.5 cm from the tip 108 of the distal end 104) and for approximately another 15 cm toward the proximal end 102. In some embodiments, approximately 80% of the total biofilm found in the endotracheal tube 100 is found within this main collection region 118. The remaining biofilm can be found from the proximal end of the main collection region 118 to the ventilator coupling element 114. The biofilm 116 can have the consistency of rubber cement or nasal secretions. The amount of biofilm 116 present in the endotracheal tube 100 can range anywhere from zero to about thirty cubic centimeters or more at the time of cleaning, depending on the dimensions and/or properties of the endotracheal tube, patient conditions or factors, the length of time within the body before cleaning, and/or other factors. In some embodiments, the internal surface of the endotracheal tube cleaning device 120 can be coated with a bactericide before insertion within a patient to help prevent or reduce the likelihood of bacterial growth within the biofilm 116.

B. Endotracheal Tube Cleaning Device

Figure 2A:
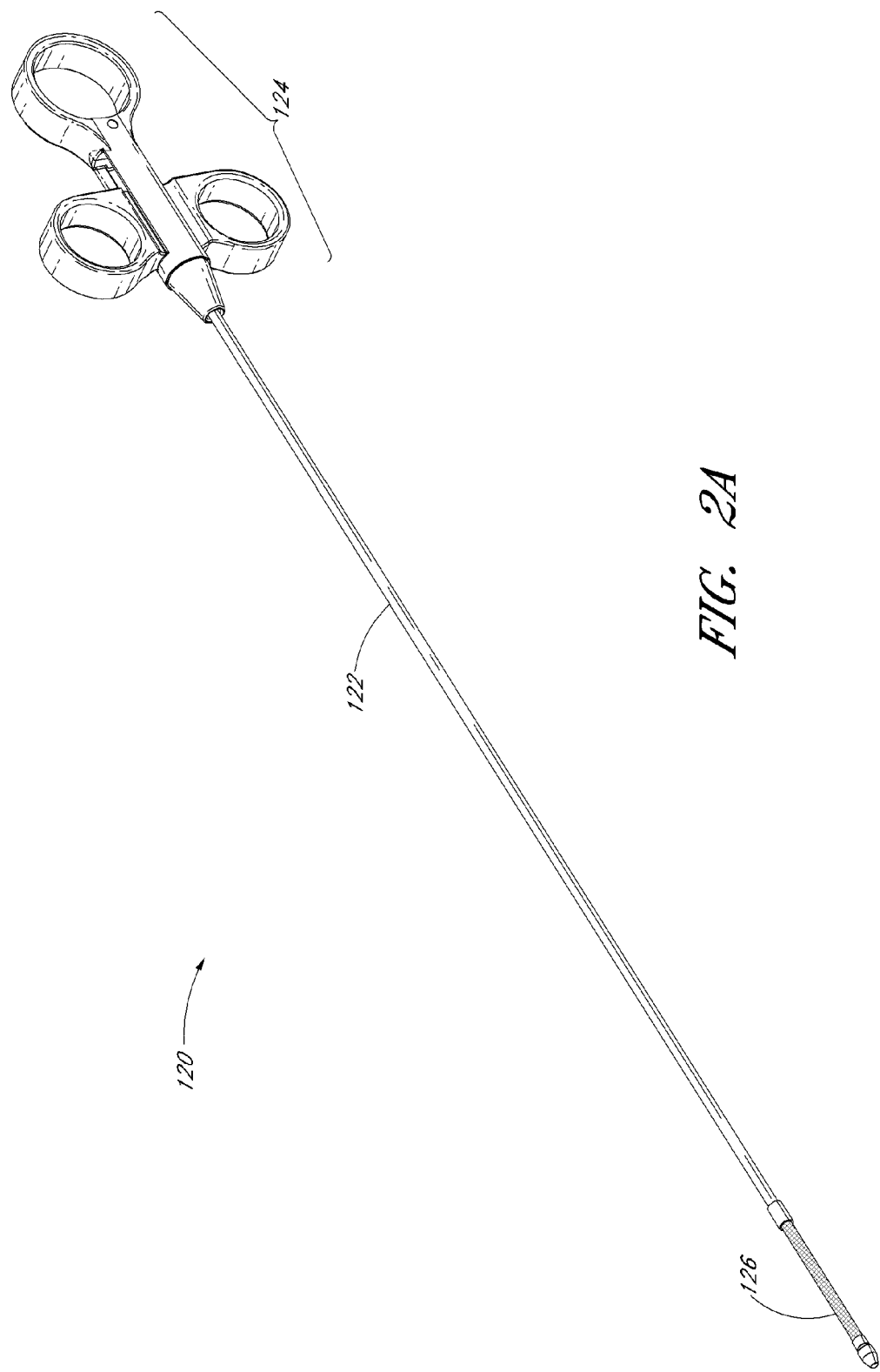
FIGS. 2A and 2B illustrate perspective and cross-sectional views, respectively, of an embodiment of an endotracheal tube cleaning device.

FIG. 2A illustrates an embodiment of an endotracheal tube cleaning device 120. As shown, the endotracheal tube cleaning device 120 can include an elongate body 122, an actuation assembly 124 at the proximal end of the elongate body 122, and a cleaning member 126 generally at the distal end of the elongate body 122. In other embodiments, the cleaning member 126 is positioned anywhere along the length of the elongate body 122 (e.g., near the proximal end of the elongate body, generally between the distal and proximal ends of the elongate body, etc.). In some embodiments, the actuation assembly 124 is a syringe-like mechanism that actuates expansion, or deployment, of the cleaning member 126. The actuation assembly 124 can be configured to provide single action deployment of the cleaning member 126. As discussed in greater detail herein, the cleaning member 126 can be configured to remove and collect or trap some or all of the biofilm 116 lining the endotracheal tube 100.

The endotracheal tube cleaning device 120 can be sized, shaped, or otherwise adapted so as to be inserted within any commercially available endotracheal tube (e.g., the endotracheal tube 100) or other body-inserted tube for cleaning. In some embodiments, the endotracheal tube cleaning device 120 can be sized, shaped, or otherwise adapted so as to be inserted within a specially-designed, proprietary endotracheal tube. In some embodiments, the outside diameter of the elongate body 122 of the endotracheal tube cleaning device 120 ranges from about 0.05 mm to about 10 mm, e.g., from about 1 mm to about 5 mm, about 2 mm to about 4.5 mm, about 2.5 mm to about 3.5 mm, about 5 mm to about 8 mm, about 8 mm to about 10 mm, or greater, and overlapping ranges thereof. The length of the elongate body 122 distal to the actuation assembly 124 can range from about 10 cm to about 70 cm, or greater, e.g., from about 10 cm to about 20 cm, about 20 cm to about 30 cm, about 30 cm to about 40 cm, about 40 cm to about 50 cm, about 50 cm to about 70 cm, and overlapping ranges thereof. In one embodiment, the length of the elongate body is about 29 cm to about 45 cm. The dimensions can be adjusted to accommodate various uses or various body-inserted tubes without departing from the spirit and/or scope of the disclosure.

In some embodiments, the endotracheal tube cleaning device 120 is manufactured with a slight curve to match or substantially conform to the curve of commercially available endotracheal tubes. The curvature of the endotracheal tube cleaning device 120 can advantageously reduce the friction between the outer surface of the endotracheal tube cleaning device 120 and the inner surface of the endotracheal tube 100 and can avoid disruption of the biofilm 116 during insertion of the endotracheal tube cleaning device 120. The curvature of the endotracheal tube cleaning device 120 can range from about a 5 cm to a 50 cm radius or from about a 10 cm to about a 30 cm radius. In one embodiment, the radius of the curvature of the endotracheal tube cleaning device 120 is approximately 17.5 cm. However, in other embodiments, the radius of curvature of the endotracheal tube cleaning device 120 can be greater or smaller than disclosed herein without departing from the spirit and/or scope of the disclosure.

Figure 2B:
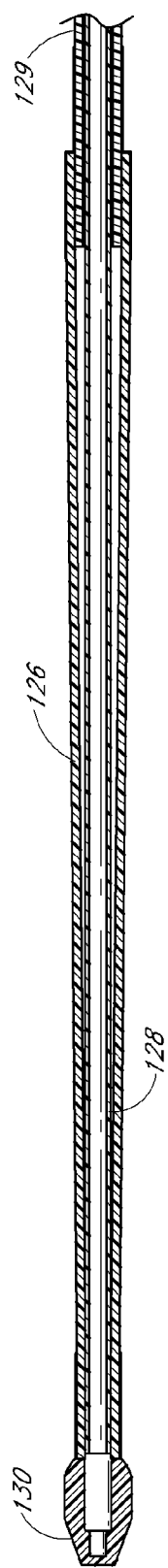

FIG. 2B illustrates a cross-sectional view of the distal end of the endotracheal tube cleaning device 120. The elongate body 122 of the endotracheal tube cleaning device 120 includes an inner shaft or sheath 128 and an outer shaft or sheath 129. In some embodiments, the inner shaft 128 and the outer shaft 129 connect the actuation assembly 124 (not shown) to the cleaning member 126. The inner shaft 128 is coupled to the distal end of the cleaning member 126 and is configured to transmit the motive force necessary to expand the cleaning member 126 by compressing the distal end of the cleaning member 126. The outer shaft 129 is coupled to the proximal end of the cleaning member 126 and holds the proximal end of the cleaning member 126 in place while the distal end is compressed or deployed. In this manner, the cleaning member 126 can be selectively expanded radially so as to impart a radial force against the inside wall of the endotracheal tube 100 and/or biofilm collected thereon. This and other embodiments of the expansion mechanism of the cleaning member 126 will be described in further detail below.

C. Endotracheal Tube Cleaning System and General Operation

Figure 3A:
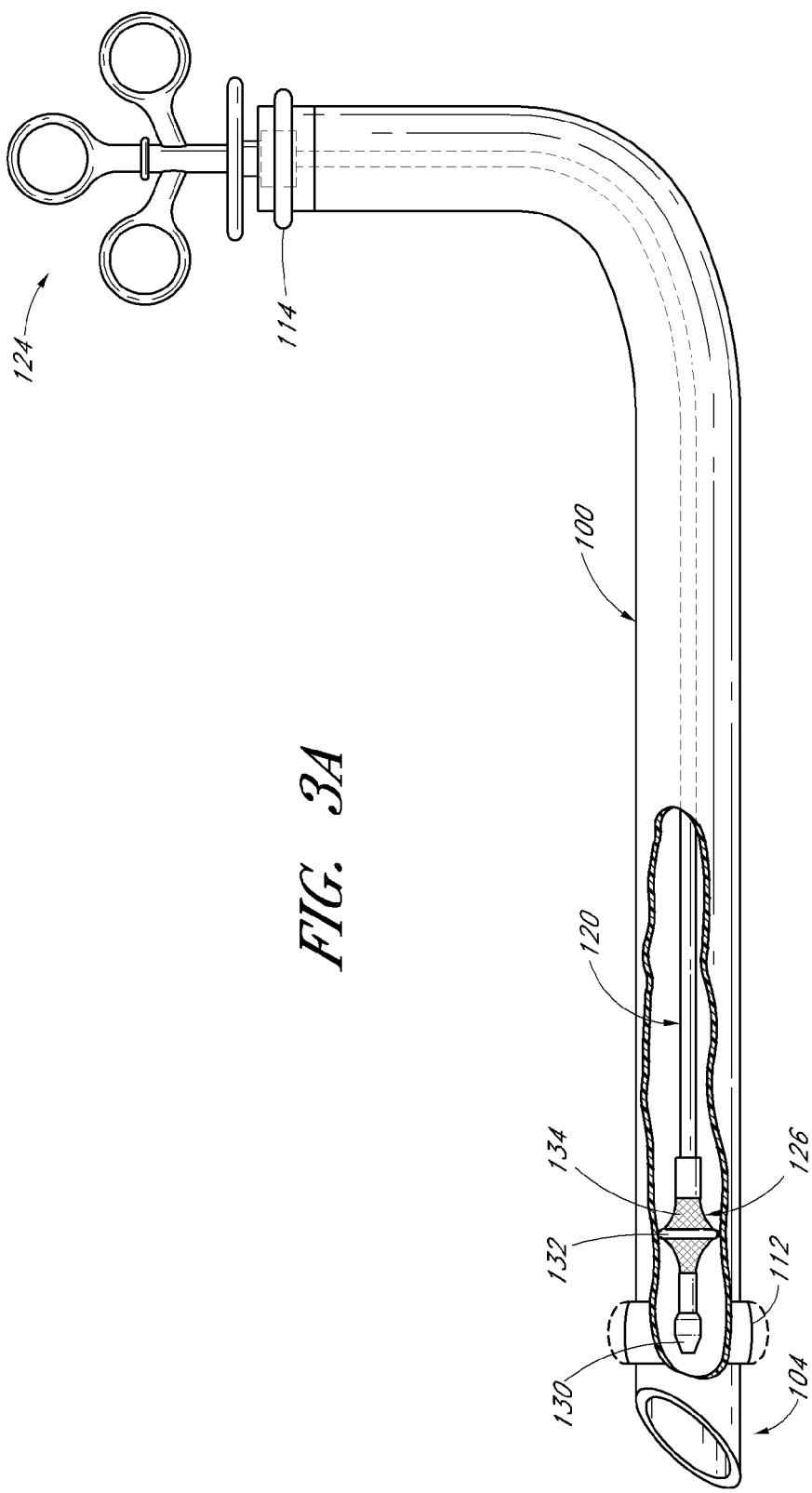
FIGS. 3A and 3B illustrate partial-sectional views of embodiments of the endotracheal tube cleaning device of FIG. 2 inserted into the endotracheal tube of FIG. 1.
Figure 3B:
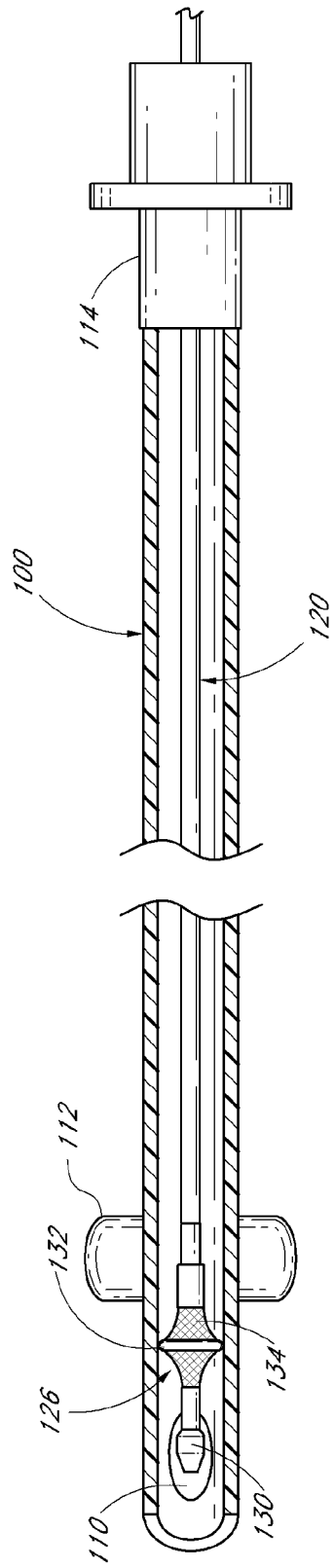

FIGS. 3A and 3B illustrate partial-sectional views of embodiments of the endotracheal tube cleaning device 120 inserted into the endotracheal tube 100. In some embodiments, the endotracheal tube 100 is disconnected from a ventilator and a distal tip 130 of the endotracheal tube cleaning device 120 is inserted through the ventilator coupling member 114. The distal tip 130 of the cleaning device 120 can be advanced until the distal tip 130 is positioned within, or just distal of, the Murphy eye 110. In other embodiments, the ventilator coupling member 114 is removed before insertion of the endotracheal tube cleaning device 120.

Figure 3C:
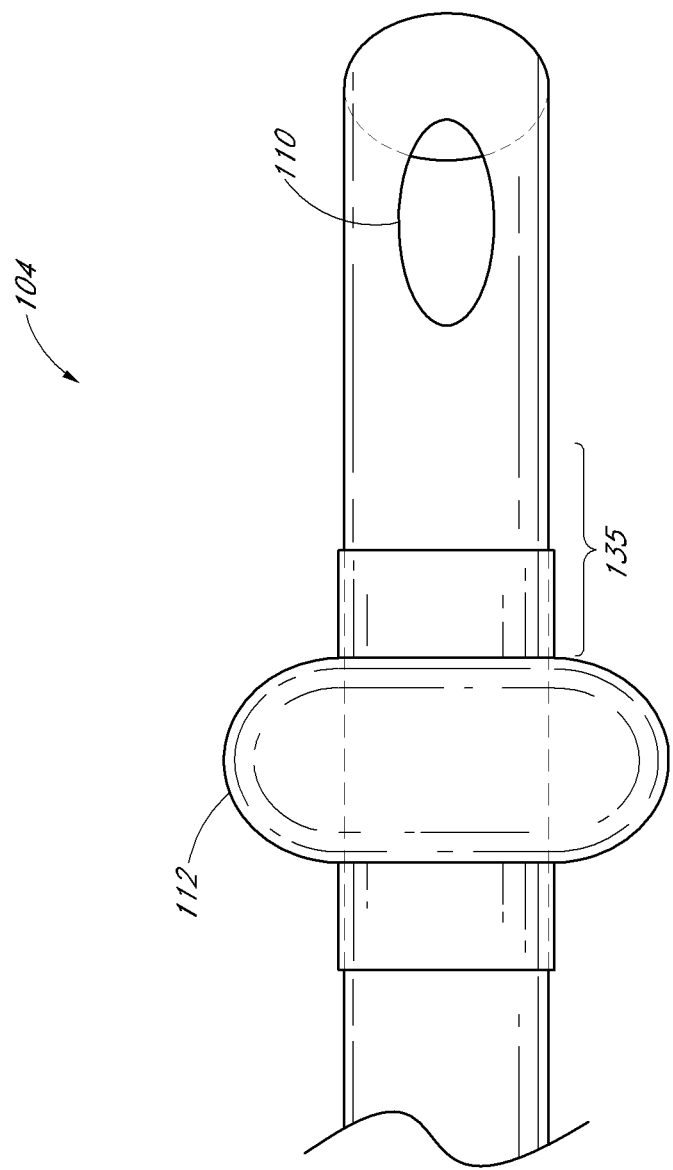
FIG. 3C illustrates a distal end of the endotracheal tube of FIG. 1.

As shown in FIGS. 3A and 3B, the cleaning member 126 can include a removal member 132 and a collection member 134. In some embodiments, the cleaning member includes more than one removal member and/or more than one collection member. The removal member 132 can be configured to contact or engage the inside wall of the endotracheal tube 100 upon radial expansion of the cleaning member 126. With reference to FIG. 3C, the removal member 132 can be positioned within a region 135 just proximal of the Murphy eye 110 (e.g., within about 0.5 cm to about 2 cm). However, the removal member 132 can be positioned at any position within the endotracheal tube 100 depending upon a determination of where the biofilm accumulation begins (e.g., via the visualization means described herein) and/or any other factor. Mechanisms for controlling the depth of insertion will be further described below.

In some embodiments, the conduit 100 to be cleaned is a gun barrel, and the cleaning device 120 or system comprises one or more removal members 132 that are configured to remove oil, grease, oxidation, rust, mineral deposits, scale, other types of deposits, gun powder residue, other types of combustion residue and/or the like. In other embodiments, the conduit 100 to be cleaned is a pipe, duct, flue (e.g., boiler flue), exhaust conduit or tubing, and the cleaning device 120 or system comprises one or more removal members 132 that are configured to remove sludge, mineral deposits, rust, other oxidation, grease, oil, soot, biofilm, scum, scale and/or the like.

Figure 3D:
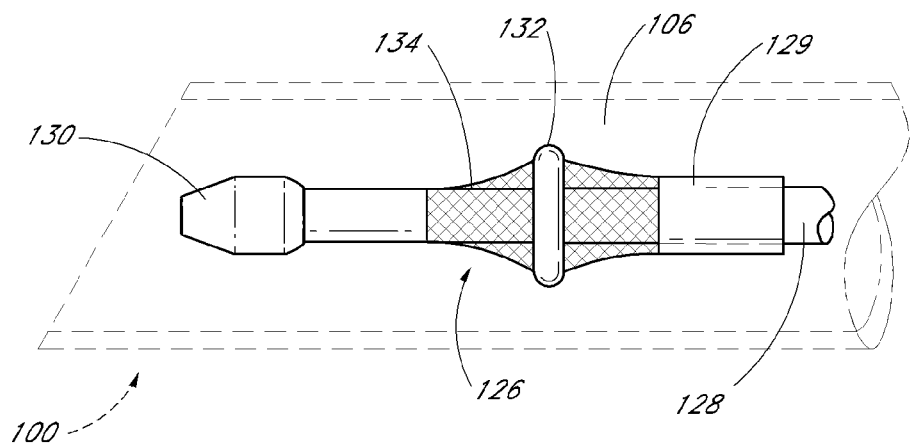
FIGS. 3D and 3E illustrate collapsed and expanded configurations, respectively, of a cleaning member of the endotracheal tube cleaning device of FIG. 2.
Figure 3E:
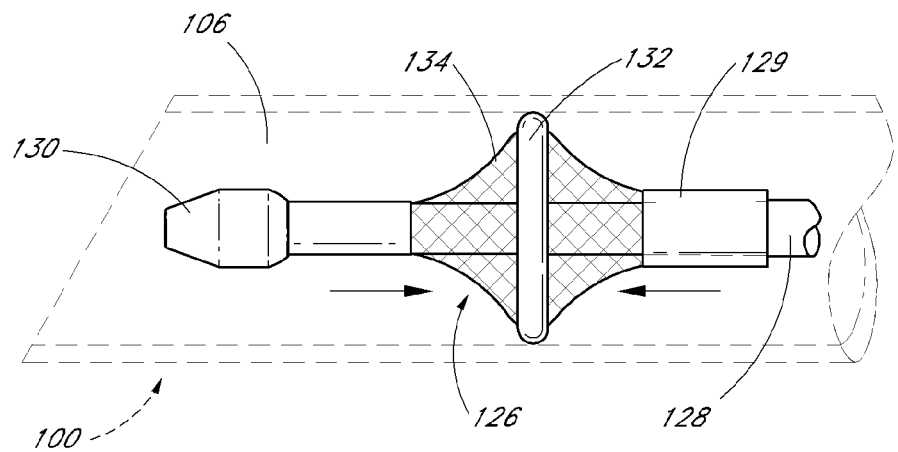

After proper positioning of the endotracheal tube cleaning device 120 within the endotracheal tube 100, the cleaning member 126 is expanded by the actuation assembly 124 such that the removal member 132 contacts the inside wall of the endotracheal tube 100 and/or the biofilm layer situated thereon. FIGS. 3D and 3E illustrate the collapsed and expanded configurations, respectively, of the cleaning member 126. After expansion of the cleaning member 126 by the actuation assembly 124, the endotracheal tube cleaning device 120 can be withdrawn from the endotracheal tube 100 by a clinician. As the endotracheal tube cleaning device 120 is withdrawn from the interior of the endotracheal tube 100, the removal member 132 removes biofilm 116 from the inside of the endotracheal tube 100, and the collection member 134 advantageously traps and collects the removed biofilm. Upon completion of a cleaning procedure or as otherwise desired, the clinician can manipulate the actuation assembly of the cleaning device to return the cleaning member 126 to its collapsed configuration. Additional details regarding the expansion and collapse of the cleaning member, as well as the manner in which the collection member traps and collects removed biofilm, are provided below.

D. Side Port

Figure 4:
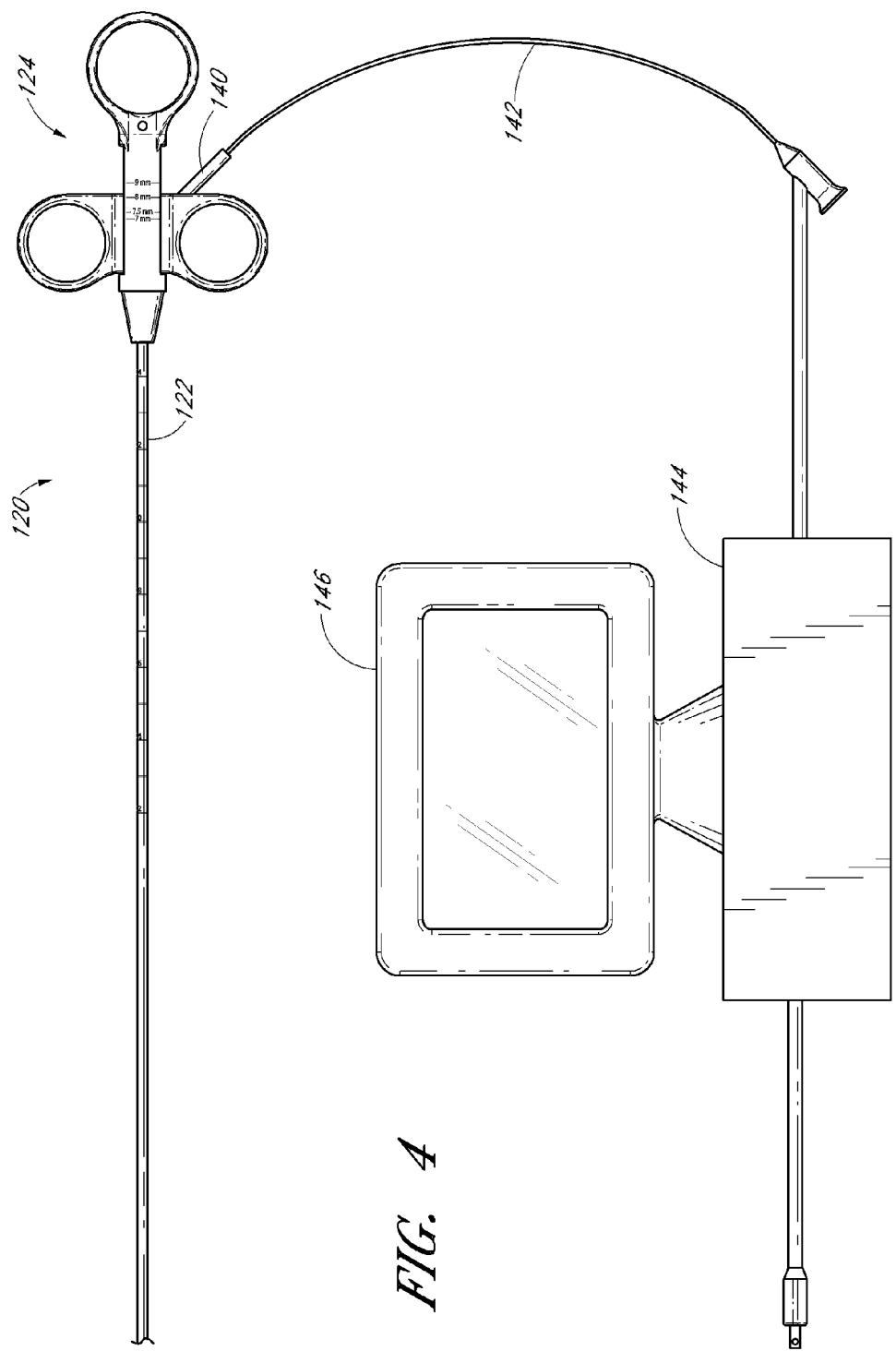
FIG. 4 illustrates an embodiment of an endotracheal tube cleaning device having a side port.

FIG. 4 illustrates an embodiment of an endotracheal tube cleaning device 120 having a side port 140 coupled to the proximal end of the endotracheal tube cleaning device 120. As shown in the embodiment of FIG. 4, the side port 140 branches off from the main body of the actuation assembly 124. The side port 140 can branch off of at any location along generally the proximal end of the endotracheal tube cleaning device 120. For example, in other embodiments, the side port 140 can branch off of the elongate body 122 at a location distal to the actuation assembly 124.

The side port 140 can be constructed without sharp edges and corners to enhance safety and/or to provide one or more other benefits. The length of the side port 140 can be sufficiently long so as to prevent contamination of the scopes, probes, catheters, and/or other instruments inserted therein due to contact or exposure to the endotracheal tube 100 or the biofilm 116 removed from the endotracheal tube 100. The length of the side port 140 can be just a few inches to avoid patient contact or as much as ten feet to avoid proximity to the patient. In some embodiments, the length of the side port 140 ranges from about 0.5 inches to about 24 inches.

In some embodiments, the side port 140 includes an elastomeric diaphragm to reduce or eliminate airflow bypass. The elastomeric diaphragm can have a slit, valve, or flap to allow insertion of scopes, catheters, and/or other instruments. The elastomeric diaphragm can comprise any suitable material, such as, for example, latex, silicone, urethane, other elastomeric or polymeric materials and/or the like. The thickness of the diaphragm can range from about 0.001 inches to about 0.1 inches or from about 0.005 inches to about 0.020 inches.

As shown, the side port 140 can be used for the introduction of a visualization scope 142. In some embodiments, the visualization scope 142 comprises an endoscope or boreoscope. However, the visualization scope 142 can include any other scope or viewing element configured to provide visual feedback to the clinician or other user of the cleaning device. The visualization scope 142 can include one or more light delivery elements (e.g., light fibers) and an imaging or visualization element (e.g., an ultrasound probe, a fiberoptic camera, a CCD camera), thereby providing a clinician with simultaneous illumination and viewing of selected portions within the endotracheal tube 100, such as, for example, the biofilm 116 along the endotracheal tube walls, possible tube obstructions, and/or the like. Accordingly, such a visualization scope or similar tools can assist in the proper placement of the endotracheal tube cleaning device 120 within the endotracheal tube 100.

In some embodiments, the visualization scope 142 includes a bundle of fiberoptic cables, with at least some of the fibers configured to provide light and at least some of the fibers configured to provide viewing capabilities. In some embodiments, the light fibers can extend around the periphery of the visualization scope 142 (e.g., along the inner wall) and the viewing fibers can extend through the central portion of the visualization scope 142. In some embodiments, the light fibers are coupled to a light source and the viewing fibers are coupled to a direct camera connection and/or to an optical connector. The visualization scope 142 can advantageously provide the clinician with an assurance that the endotracheal tube cleaning device 120 is placed properly and does not unintentionally disrupt the biofilm. In some embodiments, the visualization scope 142 is configured to extend beyond the distal end 104 of the endotracheal tube 100.

The visualization scope 142 can include an integral or removable sheath, sleeve, or jacket that extends along all or a portion of its length and that is configured to prevent against contamination and to allow relatively easy reuse of the visualization scope 142 for multiple patients and/or procedures. In some embodiments, the visualization scope 142 and/or its sheath is pre-curved to assist in positioning the visualization scope 142 within the endotracheal tube cleaning device 120.

In some embodiments, the visualization scope 142 and/or its sheath includes a stopper (fixed or adjustable) that is configured to help position the distal tip of the visualization scope 142 at a predetermined or adjustable position within the endotracheal tube cleaning device 120 (e.g., in a viewing window at the distal tip 130 of the endotracheal tube cleaning device). The stopper can be configured to abut against the proximal end of the side port 140. The side port 140 can have visible markings that correspond to markings on the visualization scope 142 to aid in the positioning of the distal end of the visualization scope 142 and/or to aid in the application of the stopper. The visible markings or indicia can comprise lines, numbers, and/or text labels.

The thickness of the sheath of the visualization scope 142 can range from about 0.05 mm to about 0.5 mm, such as, for example, about 0.1 mm. The outer diameter of the visualization scope 142 can range from about 0.5 mm to about 2 mm, depending on the size of a lumen or channel of the endotracheal tube cleaning device 120, as described in further detail below.

As schematically illustrated in FIG. 4, the visualization scope 142 can be coupled to a visualization unit 144 (e.g., via a coupling element of a camera head). In some embodiments, the visualization unit 144 includes a light source for delivery of light to the endotracheal tube, the endotracheal tube cleaning device, and/or the patient's native airway via light delivery elements. The light delivery elements can provide illumination, activation of drugs delivered within the endotracheal tube (e.g., in conjunction with photodynamic therapy) and/or other capabilities. In other embodiments, the visualization unit 144 includes a display 146 for enhanced viewing. For example, the display 146 can include a monitor capable of displaying high-quality, high-resolution images. In other embodiments, the visualization unit 144 can include one or more other types of output devices. Moreover, the visualization unit 144 can be configured to store in memory (temporarily and/or permanently) images obtained by a scope during a cleaning procedure. In some embodiments, the visualization unit 144 can transmit the images over a network (wired or wireless) to remote storage, display, and/or processing devices. These embodiments advantageously enable a supervising physician to observe and monitor the cleaning procedure and direct further intervention or treatments from a remote location (for example, outside the ICU).

In other embodiments, the side port 140 can be used for the introduction of diagnostic and/or therapeutic catheters or other instruments. Example catheters include, but are not limited to, ultrasonic catheters, radio frequency (RF) catheters, irrigation catheters, aspiration catheters, drug delivery catheters, catheters for delivering light for photodynamic or other light-based therapy, and/or the like. In yet other embodiments, diagnostic and/or therapeutic catheters can be introduced in conjunction with the endotracheal tube cleaning methods, procedures, and/or devices described herein but are not inserted within the endotracheal tube cleaning device 120 itself. Visualization and other facilitative and/or supplementary modalities will be described in further detail below.

II. Structural Components and Connection Interfaces

A. Actuation Assembly

Figure 5:
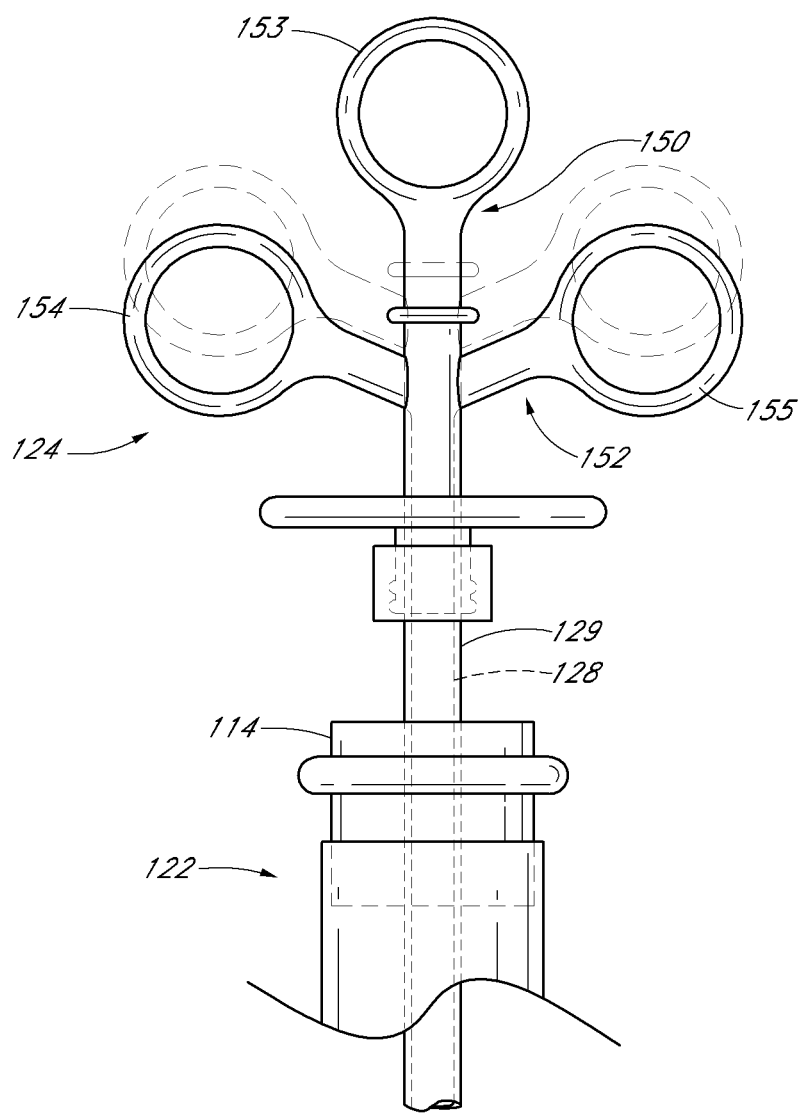
FIG. 5 illustrates the proximal end of the endotracheal tube of FIG. 1 and the proximal end of the endotracheal tube cleaning device of FIG. 2.

FIG. 5 illustrates the proximal ends of the endotracheal tube 100 and an embodiment of an endotracheal tube cleaning device 120 situated therein. As shown, the actuation assembly 124 includes a handle 150 and a trigger 152. The distal end of the handle 150 can be coupled to the outer shaft 129 of the endotracheal tube cleaning device 120 using any mechanical fastener, adhesive, and/or other coupling device or method, including, for example, interference fits, ultrasonic welding, UV cure adhesives, epoxy, and/or the like. In the depicted embodiment, the proximal end of the handle 150 includes a grip 153 that is sized, shaped, or otherwise adapted to receive an operator's thumb or other finger. In some embodiments, the distal end of the handle 150 is integral with the outer shaft 129.

The distal end of the trigger 152 can be coupled to the inner shaft 128 using any mechanical fastener, adhesives, and/or other coupling device or method, including, for example, interference fits, ultrasonic welding, UV cure adhesives, epoxy, and/or the like. In some embodiments, the distal end of the trigger 152 is integral with the inner shaft 128. In the illustrated embodiment, the proximal end of the trigger 152 includes two grips 154, 155 that may be symmetrically positioned about the longitudinal axis of the handle 150. Each of the two grips 154, 155 can be sized, shaped, or otherwise adapted to receive an operator's finger.

Materials for the handle 150 and trigger 152 can include any suitable materials, such as, for example, acrylonitrile-butadiene-styrene (ABS), polycarbonate, K-RESIN, other polymeric or elastomeric resins and/or the like. In some embodiments, the materials are tough, non-brittle, injection-moldable, plastic resins. In other embodiments, the materials include one or more modifiers to improve stiffness and/or other physical properties so that actuation of the trigger 152 and/or other functionality of the endotracheal tube cleaning device 120 is not compromised. The modifiers can include glass fiber, calcium carbonate, titanium oxide, carbon, combinations of the same, and/or the like. In some embodiments, the handle 150 and the trigger 152 include internal ribs to improve stiffness.

The actuation assembly 124 advantageously allows for single person, single-handed operation of the endotracheal tube cleaning device 120. The trigger 152 is shown in a position that keeps the cleaning member 126 in a collapsed configuration (see FIG. 3D). In order to actuate the endotracheal tube cleaning device 120 so that the cleaning member 126 transitions from the collapsed configuration into a desired deployed configuration (see FIG. 3E), manual force can be applied to the trigger 152 and handle 150 to move the trigger 152 proximally with respect to the handle 150 (shown in phantom). As the trigger 152 moves with respect to the handle 150, the inner shaft 128 and the outer shaft 129 are driven to move relative to one another. Accordingly, the relative movement of the inner and outer shafts 128, 129 can apply compressive and tensile forces to the cleaning member 126 to selectively expand and collapse, respectively, the cleaning member 126. As discussed in greater detail below, the extent of expansion of the cleaning member 126 can be advantageously controlled by the actuation member 124. In some embodiments, the actuation assembly 124 enables single-hand operation and/or single action deployment of the cleaning member 126.

B. Main Elongate Body

Figure 6:
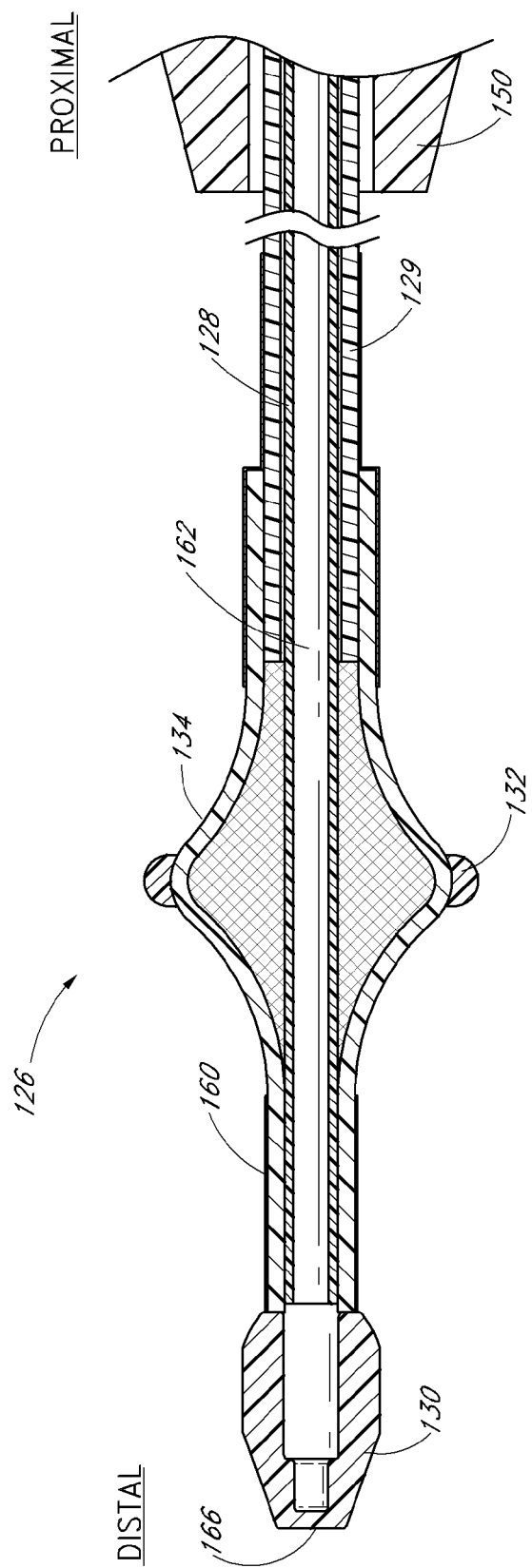
FIG. 6 illustrates a detailed partial cross-sectional view of the endotracheal tube cleaning device of FIG. 2.

FIG. 6 illustrates a detailed cross-sectional view of the distal and proximal ends of the endotracheal tube cleaning device 120. As described above, the main elongate body 122 of the endotracheal tube cleaning device 120 can include an inner shaft 128 and an outer shaft 129.

1. Outer Shaft

In some embodiments, the outer shaft 129 of the main elongate body 122 extends from the handle 150 of the actuation assembly 124 to the proximal end of the cleaning member 126. As shown in FIG. 6, the proximal end of the outer shaft 129 can be assembled into an opening located at the distal end of the handle 150. As described above, the outer shaft 129 can be coupled to the handle 150 by any suitable mechanical and/or adhesive method or device, such as interference fits, mechanical fasteners, ultrasonic welding, UV cure adhesives, epoxy, and/or the like. The distal end of the outer sheath 129 can be coupled to the proximal end of the cleaning member 126 by any suitable attachment method or device, including, but not limited to, adhesives, crush ribs, heat shrink tubing, other low-profile mechanical fasteners, other attachment methods or devices, ultrasonic bonding, interference fits, and/or the like.

With continued reference to the embodiment illustrated in FIG. 6, the outer shaft 129 comprises a central lumen or channel in which the inner shaft 128 is slidably retained. In some embodiments, the cross-section of the outer shaft 129 can be circular, substantially circular, elliptical, oval and/or any other shape. In some embodiments, the outer diameter of the outer shaft 129 ranges from about 1.5 mm to about 4 mm; however the outer diameter of the outer shaft 129 can be smaller than 1.5 mm or larger than 4 mm, as desired and/or required. In some embodiments, the outer shaft 129 is an extrusion comprising polyolefin and/or one or more other plastic materials, such as, for example, polypropylene, PEPAX, polyester, nylon, polyimide, polyethylene terephthalate (PET), polyethylene terephthalate glycol (PETG), and/or the like.

2. Inner Shaft

In some embodiments, the inner shaft 128 is located within an inner lumen of the outer shaft 129 and is configured to move with respect to the outer shaft 129 in a direction along the longitudinal axis of the outer shaft 129. In some embodiments, the inner shaft 128 extends from the trigger 152 to the distal tip 130 of the endotracheal tube cleaning device 120. The inner shaft 128 can be coupled to the distal tip 130 by any suitable attachment method or device, such as, for example, adhesives, crush ribs, heat shrink tubing, mechanical fasteners, other mechanical devices or methods, low-profile mechanical connection means, ultrasonic bonding, interference fits, and/or the like. As shown, the inner shaft 128 can be coupled to the distal tip 130 and to the cleaning member 126 with heat shrink tubing 160. In other embodiments, the inner shaft 128 and the distal tip 130 are integrally formed as a single molded component.

In some embodiments, the inner shaft 128 is a hollow sheath or tube. In some embodiments, the outer diameter of the inner shaft 128 is less than 4 mm and the inner diameter of the inner shaft 128 is greater than 1 mm; however, the inner shaft 128 can have any other diameter, as desired and/or required. For example, the outer diameter of the inner shaft 128 can range from about 0.85 mm to about 2 mm and the inner diameter of the inner shaft 128 cm range from about 0.5 mm to about 1.25 mm. The inner shaft 128 can include a central lumen or channel 162 for the introduction of a visualization scope and/or one or more diagnostic or therapeutic catheters or other instruments. In some embodiments, a visualization element (e.g., fiber optic camera) of a visualization scope (e.g., visualization scope 142) can be inserted into the central lumen or channel 162. The central lumen or channel 162 can have a diameter ranging from about 0.5 mm to about 1.5 mm (e.g., about 1 mm). However, the diameter of the central lumen or channel 162 can be smaller than 0.5 mm or larger than 1.5 mm as desired and/or required by the dimensions of the inner shaft 128. A depth stop 166 can be included to position a visualization scope for desired or required optical characteristics, thereby resulting in maximum viewing potential.

In other embodiments, the inner shaft 128 includes one or more internal and/or external channels adapted to selectively receive scopes and/or other instruments or devices for visualization and/or any other purpose. For example, the one or more channels can be used for light delivery, photodynamic therapy, fluid delivery (e.g., air, therapeutic agents, saline), irrigation, aspiration, and/or the like. In some embodiments, the one or more channels can comprise an equilibrium channel to reduce or alleviate the any negative pressure or suction effect created distal to the expandable cleaning member as the endotracheal tube cleaning device 120 is being withdrawn from the endotracheal tube 100. The channels can extend through any length of the inner shaft. For example, one or more channels can extend from generally the proximal end to generally the distal end of the endotracheal tube cleaning device 120. In some embodiments, the one or more channels can include an inlet in communication with the side port 140 and one or more outlets in the distal tip 130, in or adjacent to the removal member 132, in the side wall of the endotracheal tube cleaning device 120. In other embodiments, the one or more channels can include inlets or outlets at other locations of the endotracheal tube cleaning device 120.

In other embodiments, the inner shaft 128 is a solid, central rod. The inner shaft 128 can have a circular, substantially circular, elliptical, oval, and/or any other cross-sectional shape. In some embodiments, the inner shaft 128 comprises an extrusion having polyolefin and/or other plastic materials, such as, for example, polypropylene, PEPAX, polyester, nylon, polyimide, polyethylene terephthalate (PET), polyethylene terephthalate glycol (PETG), and/or the like.

3. Distal Tip

In some embodiments, the distal tip 130 is a closed tip to prevent against exposure of the internal structure of the endotracheal tube cleaning device 120, and any instruments or devices inserted therein, to the biofilm 116 or other potential contaminants within the patient's body. The distal tip 130 of the endotracheal tube cleaning device 120 can comprise one or more injection-moldable plastics, polymeric resins, including, but not limited to, polycarbonate, PET, PETG, nylon, polypropylene, K-RESIN, and/or the like. In some embodiments, at least a portion of the distal tip 130 can comprise a clear, transparent or semi-transparent material to form a viewing "window." The injection mold of the distal tip 130 can be polished (e.g., using an SPE/SPI A1 "high polish" finish of the injection mold) such that at least the distal end of the distal tip 130 is optically transparent or partially optically transparent. In some embodiments, the transparent material can be configured to enable a "fish eye" view for enhanced viewing of the endotracheal tube 100 itself, any biofilm that could be accumulating in the tube, and/or the like.

In some embodiments, the viewing window can have optical properties to provide magnification and/or angular correction to correct for the natural tendency for the device to follow the outer bend of the endotracheal tube. For example, the optical properties can enable the scope to provide a view of the lumen in the middle of the endotracheal tube and not a view of the side of the visualization scope or the biofilm itself. The viewing window can also comprise a filter, coating, layer and/or other mechanism to reduce glare of flashback from a light delivery element (e.g., an endoscope light).

In some embodiments, the distal end of the distal tip 130 is sized, shaped, and/or otherwise adapted to facilitate introduction into the biofilm 116. For example, the distal end of the distal tip 130 can have a radius from about 0.010 R to about 0.050 R, or from about 1 mm to about 15 mm. The distal tip 130 can be radiused using a radio frequency tool, by injection molding and/or any other suitable forming technologies. In arrangements wherein a visualization scope is to be used in conjunction with the endotracheal tube cleaning device 120, the optically clear distal end of the distal tip 130 can be relatively thin (for example, from about 0.010 inches to about 0.20 inches thick) to improve the optical qualities of the distal tip 130 for enhanced visualization. In other embodiments, the optical properties of the clear, transparent or semi-transparent materials used to form the distal tip 130 (e.g., an extrudable grade of clear polypropylene) may help reduce or eliminate the need of the relatively thin tip.

In some embodiments, the distal tip 130 can include one or more outlets or ports (not shown) to provide access to the interior of the endotracheal tube and/or to the patient's airway (e.g., the tracheobronchial tree) through the endotracheal tube cleaning device 120. For example, an outlet can be in communication with an inner lumen or channel of the endotracheal tube cleaning device 120 into which diagnostic and/or therapeutic instruments (e.g., aspiration, irrigation, and/or drug delivery mechanisms) can be inserted. In some embodiments, the one or more outlets can permit the escape of a fluid, such as air or therapeutic agents, from the endotracheal tube cleaning device 120. In other embodiments, the one or more outlets can permit the escape of a catheter or conduit inserted through an internal channel of the endotracheal tube cleaning device 120. The outlet can include a diaphragm, slit, one-way valve and/or the like to substantially seal off the inner lumen or channel, thereby preventing or reducing the likelihood of contamination of the interior of the endotracheal tube cleaning device 120 and/or the therapeutic and/or diagnostic instruments inserted therein.

C. Cleaning Member

With continued reference to FIG. 6, an embodiment of the cleaning member 126 is illustrated. As described above, the cleaning member 126 can include a removal member 132 and a collection member 134. In some embodiments, the removal member 132 and the collection member 134 can be two separate members. In other embodiments, a single, integral removal/collection member can perform removal and collection of accumulated biofilm. In yet other embodiments, the cleaning member 126 may not include a removal member 132 (e.g., an O-ring, wiper, etc), as depicted in the embodiments illustrated in FIGS. 2A and 2B, for example. In some embodiments, the cleaning member 126 comprises a distensible scaffold that removes and collects the deposited biofilm.

According to some embodiments, the removal member 132 and/or any other portion of the cleaning member is configured to be actively mechanically actuated between an expanded configuration and a collapsed configuration. In several embodiments, the removal member 132 and/or any other portion of the cleaning member 134 are actively mechanically actuated without the use of a sheath, sleeve, covering and/or the like. In another embodiment, the removal member and/or any other portion of the cleaning member are non-bristled and/or non-sheathed.

In some embodiments, the removal member 132 and/or the collection member 134 of the cleaning member 126 can elute and/or be coated with a fluid, drug, therapeutic agent, and/or other medicament or substance that is configured to clean, disinfect, decontaminate, sterilize, and/or prevent future contamination of the endotracheal tube 100 and/or to degrade, disperse, and/or dissolve biofilm deposited along the interior surface of the endotracheal tube. Such materials can include, for example, an anti-bacterial agent, a mucolytic agent, a saline solution, a sterilant, an enzymatic cleaner, a germicide, and antiviral drug, an antimicrobial drug, and/or a detergent. A coated removal member and/or collection member can be configured to deliver the fluid, drug, therapeutic agent, and/or other materials upon contact with the inside wall of the endotracheal tube 100. A coating of the cleaning member 136 can also comprise one or more absorbent materials, such as, for example, super-absorbent polymers (e.g., polyacrylimide and/or the like).

1. Collection Member

As described above, the collection member 134 can be adapted to collect and/or trap biofilm removed by the removal member 132. In some embodiments, the collection member 134 effectuates expansion of the removal member 132 as it is expanded by the relative movement between the inner and outer shafts 128, 129. However, any other method of selectively expanding and contracting the removal member 132 can be used. The collection member 134 can advantageously be constructed to allow sufficient airflow through the endotracheal tube 100 during use. For example, the air flow rates can range from about 1 liter per minute to about 10 liters per minute or from about 2 liters per minute to about 5 liters per minute.

In some embodiments, the collection member 134 comprises a distensible scaffold that can be mechanically actuated (e.g., actively mechanically actuated) between an expanded configuration and a collapsed configuration. In some embodiments, the scaffold comprises a mesh or braided scaffold (see FIG. 6). In several embodiments, the scaffold is non-sheathed and/or non-bristled. The scaffold can comprise a woven tubular braided material. The fibers of the braid can range in diameter (or other cross-sectional dimension) from about 0.001 inches to about 0.04 inches, or greater, e.g., about 0.001 inches to about 0.005 inches, about 0.005 inches to about 0.010, about 0.010 inches to about 0.020 inches, and overlapping ranges thereof. However, the diameter or other cross-sectional dimension of the fibers can be smaller than 0.001 inches or greater than 0.040 inches, as desired or required. The braided material can be comprised of PET, nylon, polyester, polypropylene and other extrudable plastic resins that are flexible in the extruded state. The pick count of the braided material can range from 5 to 25 picks per inch, or greater, e.g., from about 5 to 8 picks per inch, about 8 to 12 picks per inch, about 12 to 14 picks per inch, about 14 to 16 picks per inch, about 16 to 18 picks per inch, about 18 to 20 picks per inch, about 20 to 25 picks per inch, and overlapping ranges thereof.

According to some embodiments, the scaffold, the collection member and/or any other portion of the cleaning device is configured to be actively mechanically actuated between an expanded configuration and a collapsed configuration. In several embodiments, the scaffold, the collection member and/or any other portion of the cleaning device are actively mechanically actuated without the use of a sheath, sleeve, covering and/or the like. In another embodiment, the scaffold, the collection member and/or any other portion of the cleaning device are non-bristled and/or non-sheathed.

Figure 7:
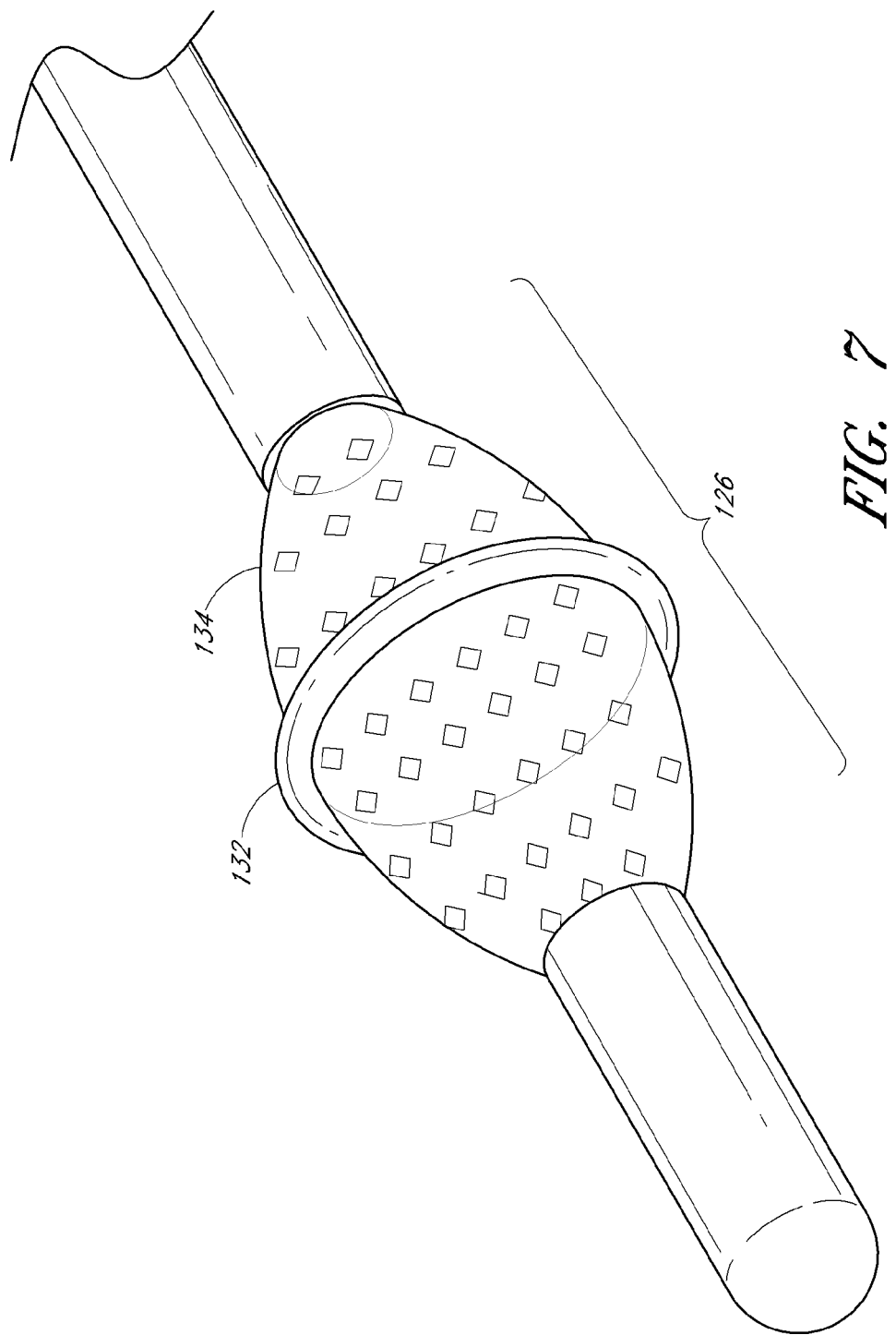
FIG. 7 illustrates an embodiment of a collection member of an endotracheal tube cleaning device.

In other embodiments, the collection member 134 is a scaffold comprising a porous elastomeric polymer material, such as silicone, urethane, and/or latex, or a porous foam material. FIG. 7 illustrates an embodiment of the collection member 134 comprising a porous elastomeric polymer material.

In some embodiments, the collection member 134 has a generally uniform construction from one end to the other end. In other embodiments, the collection member 134 can have varying constructions for different portions of the collection member 134 to serve different purposes. For example, a distal section of the collection member 134 can have a construction just large enough to allow air flow (e.g., high pick count, fine weave, small pore size, etc.), which advantageously results in the efficient trapping and storage of biofilm 116, and the proximal section of the collection member 134 can have a construction with larger openings (e.g., low pick count, loose weave, large pore size, etc.) to facilitate collection of the biofilm 116 while still allowing expansion of the removal member 132. FIGS. 9A-9D, which are described below, illustrate embodiments of collection members having proximal and distal sections of varying porosity. In some embodiments, the pick count of the distal section of the collection member 134 can range from about 10 to about 25 picks per inch and the pick count for the proximal section can range from about 5 to about 10 picks per inch. In some embodiments, the distal section can have a construction that is impermeable or substantially impermeable to fluids or permeable so as to allow fluids to filter through while catching solid and semi-solid debris.

Figure 8:
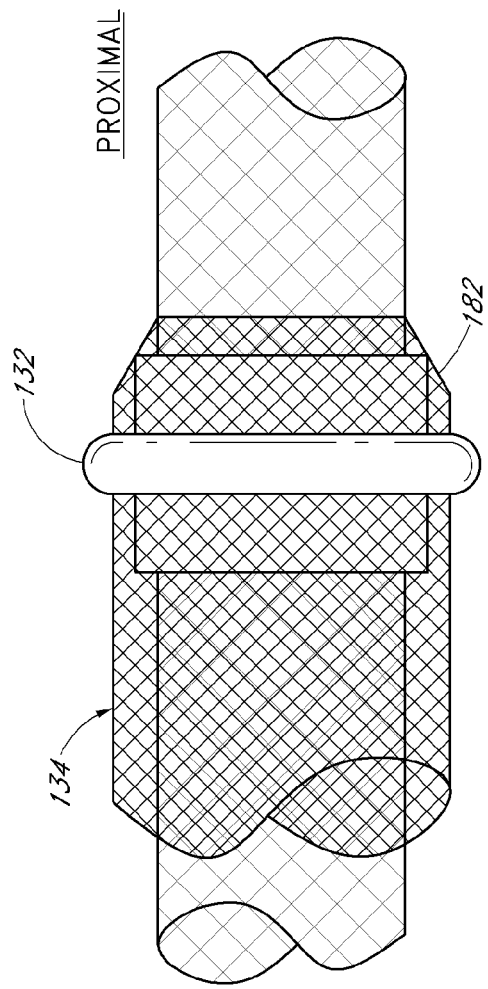
FIG. 8 illustrates an embodiment of a collection member comprising a double-layer mesh scaffold.

In some embodiments, the collection member 134 comprises two or more layers of braided or mesh material. The two or more layers can have varying pore size or pick count constructions. For example, FIG. 8 illustrates an embodiment of the collection member 134 comprising a double-layer mesh scaffold. In some embodiments, the proximal section of the collection member 134 comprises a first mesh layer having a relatively large pore size (e.g., greater than about 0.1 inch opening) and the distal section of the collection member 134 comprises the first mesh layer having the relatively large pore size as an inner mesh layer and a second outer mesh layer having a relatively small pore size (e.g., about 0.05 inch opening). The inner mesh layer and outer mesh layer can be ultrasonically welded or otherwise coupled together at various locations (e.g., the proximal and distal ends of the outer mesh tube). For example, the distal ends of the two mesh layers can be coupled together and/or to the inner shaft 128 using heat seal or heat shrink band clamps 160. In other embodiments, the two mesh layers are coupled by sutures, epoxy, adhesive, other low-profile attachment devices, and/or the like. The outer mesh layer can include an outer mesh ring 182 having the relatively large pore size that is ultrasonically welded or otherwise connected to the inner mesh layer at one or more locations adjacent to the removal member 132. The outer mesh ring can have a conical or substantially conical shape. In some embodiments, both the proximal section and the distal section of the collection member 134 comprise two or more mesh layers.

In some embodiments, the length of the collection member ranges from about 0.2 inches to about 1 inch. In one embodiment, the length of the collection member is about 0.4 inches. In some embodiments, the length is selected to effectuate a "tent-like" configuration when deployed instead of a "sausage-like" configuration. The "tent-like" configuration advantageously focuses the radial force along a perpendicular plane through the removal member 132.

In some embodiments, the collection member 134 is expanded generally uniformly across its length. For example, in its expanded configuration, the collection member 134 can exhibit a "tent-like" form, wherein the distal half and the proximal half have a convex shape (as shown in FIG. 6). In other embodiments, a proximal portion (e.g., the proximal half) of the collection member 134 can be configured to expand in a concave fashion and a distal portion (e.g., the distal half) of the collection member 134 can be configured to expand in a convex fashion. The proximal and distal portions can be integral or separate.

Figure 9A:
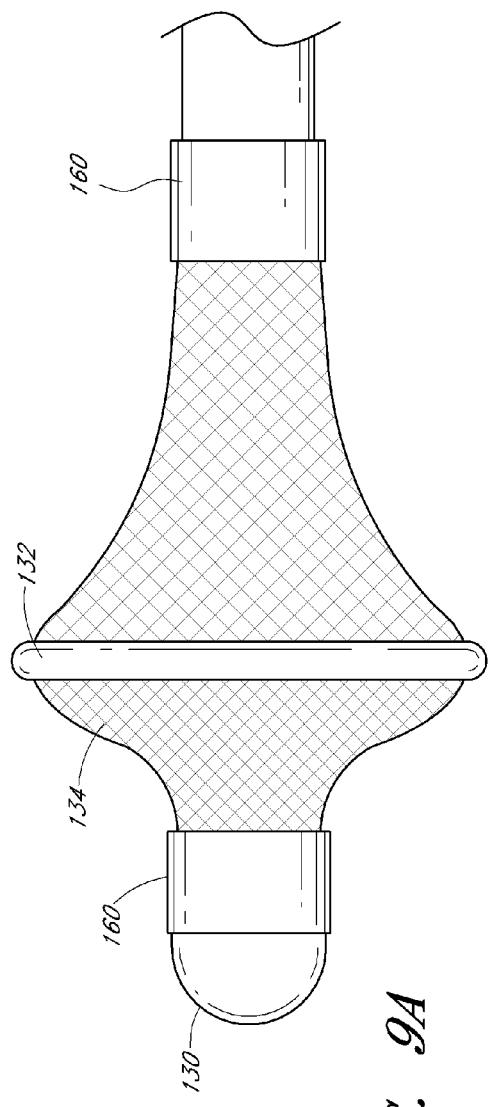
Figure 9B:
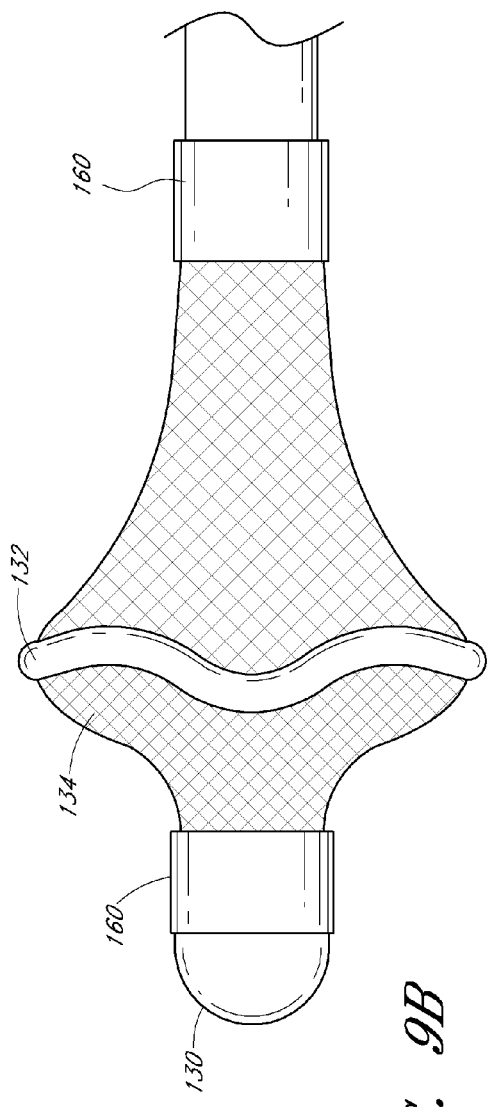

FIGS. 9A and 9B illustrate embodiments of the collection member 134 having a convex distal section and a concave proximal section. The concave profile of the proximal portion can advantageously keep the surface of the collection member 134 away from the inner wall of the endotracheal tube 100, thereby ensuring that the outer surface of the removal member 132 is the only surface that comes in contact with the inner wall of the endotracheal tube 100. In some embodiments, the concave profile advantageously results in more efficient biofilm collection than the convex profile. For example, the concave profile can create more surface area and volume for collection of biofilm. In some embodiments, the collection member 134 is formed of two separate elements. The slight wave pattern of the removal member 132 in FIG. 9B can advantageously improve radial deployment of the collection member 134, can improve collection due to its greater surface area, and/or can increase the expandability of the removal member 132.

With reference to FIGS. 9C and 9D, the concave profile of the proximal section of the collection member 134 can be effected by attaching one or more rings 192 about the proximal section of the collection member 134 to constrain the expansion. If multiple rings are used, the rings 192 can be spaced apart and can be configured to expand to different diameters to effectuate a desired profile. In some embodiments, the length of the collection member 134 can be increased with the inclusion of the rings 192 to constrain the expansion of the proximal section of the collection member 134. For example, the length of the collection member 134 can range from about 0.4 inches to about 2 inches. The collection member 134 can be constructed to have a capacity of about 15 cubic centimeters (ccs) of biofilm or other material; however a capacity of less than or more than 15 ccs can be used as desired and/or required.

2. Removal Member

In general, the removal member 132 is configured to be expanded during use to come in contact with the interior surface of the endotracheal tube 100 (or other conduit) and to remove the deposited debris (e.g., biofilm) therefrom as the cleaning device 120 is withdrawn from the endotracheal tube 100. In some embodiments, the removal member 132 is configured to engage the interior surface of the endotracheal tube 100 with a smooth, regular outer surface. In other embodiments, the surface profile of the removal member 132 can have an irregular shape. In one embodiment, the removal member is flush with the outside periphery of the scaffold (which, in some embodiments can serve as a collection member). In other embodiments, the removal member protrudes beyond the outside periphery of scaffold by about 0.05 mm to about 4 mm, such that, in some embodiments, only the removal member contacts the interior surface of the endotracheal tube (or other conduit).

In some embodiments, the removal member 132 comprises one or more soft, flexible, expandable materials, such as, for example, silicone, UV curable silicone, ethylene vinyl acetate (EVA), thermoplastic elastomer (TPE), KRATON polymers, polyisoprene, urethane, silicone rubber, other suitable flexible and low-tear materials, and/or the like.

In some embodiments, the removal member 132 has a material softness that enables optimum deployment of the collection member 134 and reduces or prevents "hydroplaning" of the removal member 132 as it is withdrawn, thereby ensuring that the biofilm is removed in an efficient manner. If the material is too soft, the removal member 132 can gradually tear or pull away from the collection member 134 over time.

In some embodiments, the use of materials that are too hard can retard the deployment of the collection member 134, because the removal member 132 exerts a backward force on the collection member 134 as it is expanded. Failure to adequately deploy the removal member 132 can prevent the removal member 132 from adequately engaging the inside wall of the endotracheal tube 100 with sufficient radial force to effectively remove biofilm. In other embodiments, if the material is too soft, then the removal member 132 "hydroplanes," thereby failing to adequately remove the biofilm as the endotracheal tube device 120 is withdrawn.

The softness of the removal member 132, as measured on a durometer scale, can range from 20 Shore A to 60 Shore A when silicone is used or from about 0 Shore A to about 40 Shore A when urethane or other materials are used. In one embodiment, the softness of the removal member 132 is 30 Shore A when silicone or a similar material is used. The removal member 132 can be configured to expand to approximately 200 to 250 percent of its nominal diameter. In some embodiments, the removal member 132 can be configured to expand to accommodate endotracheal tubes having a diameter between about 1 to about 10 mm.

The removal member 132 can be removably or integrally coupled to the collection member 134 using any suitable attachment method or device, including but not limited to, adhesive, epoxy, suture, welding, casting, mechanically connected interference fit, overmolding, and/or the like. In one embodiment, such as when the removal member 132 comprises urethane material, the removal member 132 becomes chemically bonded to the collection member 134 (e.g., a PET braid scaffold) when overmolded. In some embodiments, the removal member 132 is coupled to the outer surface of the collection member 134. In other embodiments, the removal member 132 is coupled to the inner surface of the collection member 134. In yet other embodiments, the removal member 132 is detachable or separable from the collection member 134. In still other embodiments, the removal member 132 is integral with the collection member 134. In one embodiment, an integral well is formed underneath and through the collection member 134 when the removal member is overmolded or formed with an applicator. The integral well design can advantageously prevent or reduce the likelihood of the removal member 132 being sheared from the collection member 134 during operation.

In one embodiment, the removal member 132 comprises an expandable O-ring wiper that generally circumscribes the collection member 134. The O-ring wiper can be circular, substantially circular, elliptical, oval, and/or any other shape. The O-ring wiper can be a single, smooth, regular, continuous bead that is in a perpendicular plane to the collection member 134. In another embodiment, the removal member 132 comprises a wavy, or undulating, pattern (as shown, for example, in FIGS. 9B and 9D). The peaks of the wave pattern can vary from between about 0.05 inches to about 0.5 inches peak to peak, or e.g., about 0.1 inches to about 0.35 inches.

Figure 10A:
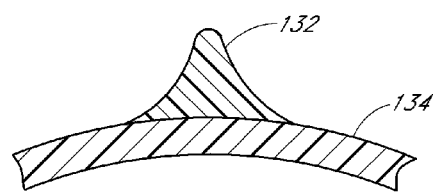
Figure 10B:
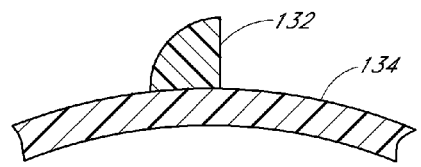

FIGS. 10A-10H illustrate cross-sectional profiles of various alternative embodiments of the removal member 132 mounted on a deployed collection member 134. In some embodiments, the portion of the removal member 132 that contacts or engages the inner surface of the endotracheal tube provides a smooth, regular contact surface. In other embodiments, the contact portion of the removal member 132 comprises an irregular contact surface. FIG. 10A illustrates an O-ring having a substantially triangular cross section. The concave slope and radius of the edges of the substantially triangular O-ring can be varied as desired and/or required. FIG. 10B illustrates an O-ring having a quarter-circle cross section. The quarter-circle O-ring of FIG. 10B can be tapered on the distal side for minimal disruption of biofilm on introduction and optimal wiping of biofilm on removal of the device. In some embodiments, the proximal side of the quarter circle O-ring of FIG. 10B is concave, thus forming an O-ring having a "wave-like" or "fin-like" cross section.

Figure 10C:
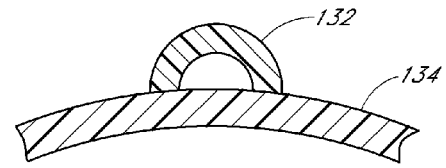
Figure 10D:
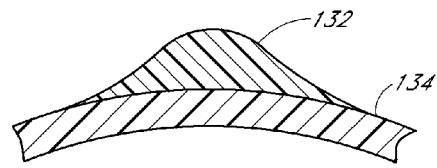
Figure 10E:
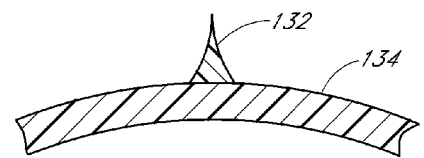
Figure 10F:
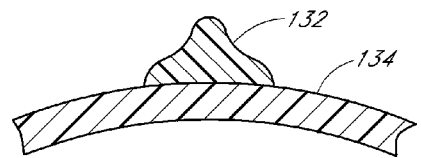
Figure 10G:
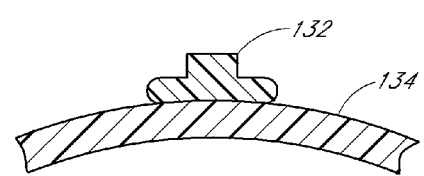
Figure 10H:
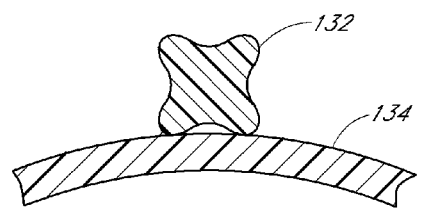

FIG. 10C illustrates an O-ring having a U-shaped cross section. FIG. 10D illustrates an O-ring having a half-circle or half-moon shaped cross section. The radius of the half-circle can range from about 0.001 inches to about 0.1 inches, or greater, e.g., about 0.005 inches to about 0.01 inches, about 0.01 inches to about 0.025 inches, about 0.025 inches to about 0.05 inches, about 0.05 inches to about 0.1 inches, and overlapping ranges thereof. FIG. 10E illustrates an O-ring having a "squeegee-like" cross section with a steep slope and a narrow wiping or scraping edge. FIG. 10F illustrates an O-ring having a half-circle cross section with a parting line. The parting line has been emphasized for illustration and is not necessarily to scale. The parting line can be a natural or intentional result of the molding process in forming the O-ring. FIG. 10G illustrates an O-ring having a squared-off contact portion. FIG. 10H illustrates an O-ring having an X-shaped cross section.

The removal member 132 can be constructed of two or more materials of an expandable nature. In some embodiments, the majority of the body of the removal member 132 comprises a material having a suitable durometer for expansion and the contact portion comprises a more rigid material to provide sufficient strength and rigidity for the effective wiping or removal of biofilm.

FIG. 11A illustrates an embodiment of a removal member 132 having a helical or "barber pole" configuration. Other embodiments of removal member configurations include, but are not limited to, a ribbed O-ring, an O-ring having a full circle cross-section, and an O-ring having a varying cross-section about its circumference. In still other embodiments, the removal member 132 can comprise shaving members, bristles, or other protrusions. In various embodiments, the removal member can comprise bumpy, ribbed, saw-like, abrasive, rough, textured, slotted, and/or smooth or substantially smooth materials. In some embodiments, the removal member 132 can range from about 0.015 inches to about 0.050 inches in height and from about 0.015 inches to about 0.1 inches in width.

In some embodiments, the cleaning member 126 can include multiple removal members 132, as illustrated in FIG. 11B. The multiple removal members 132 can have the same or different profiles. Different profiles can be used to accomplish various purposes, as will be described in further detail below. In some embodiments, the multiple removal members 132 include partial O-rings that extend around a partial circumference of the collection member 134 and are rotationally staggered.

In some embodiments, the removal member 132 can include holes or apertures for fluid delivery, for suction, and/or for any other purpose. The removal member 132 can be connected to a fluid delivery channel or a suction/aspiration conduit within the endotracheal tube cleaning device 120. For example, the removal member 132 can be configured to deliver fluid and/or other materials that help to disperse, degrade, or loosen hardened, more adherent biofilm and/or to deliver drugs to the accumulated biofilm and/or the internal surface of the endotracheal tube.

3. Multiple Cleaning Members

In some embodiments, the endotracheal tube cleaning device 120 includes multiple cleaning members 126. The multiple cleaning members 126 can be constructed to serve different purposes. For example, the removal member 132 of each of the multiple cleaning members 126 can be constructed with a different profile or cross section. In other embodiments, each of the removal members 132 can have the same profile or cross section.

Figure 12:
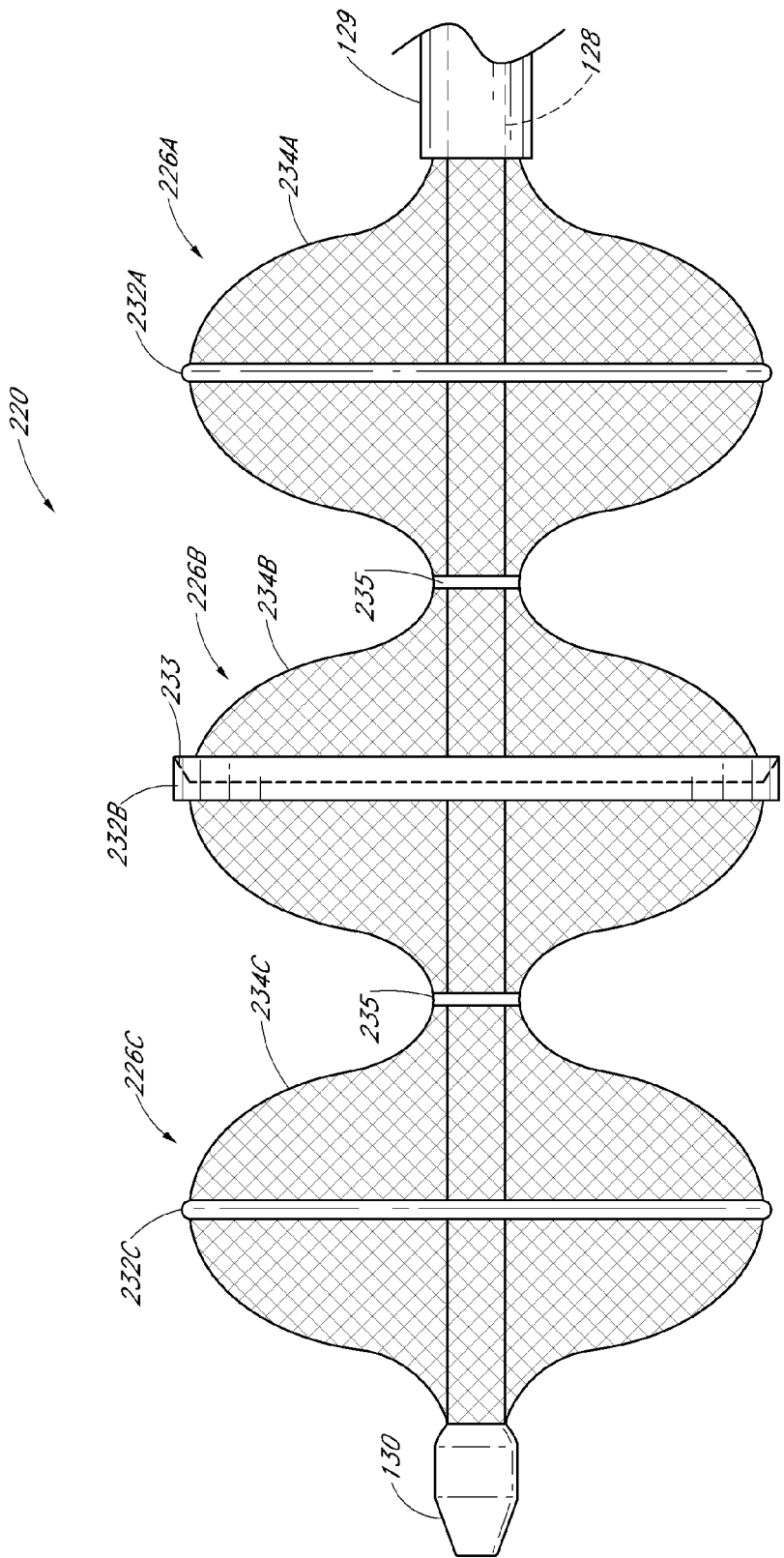
FIG. 12 illustrates an embodiment of an endotracheal tube cleaning device having multiple cleaning members.

FIG. 12 illustrates an embodiment of an endotracheal tube cleaning device 220 having three cleaning members 226A-226C.

Figure 13A:
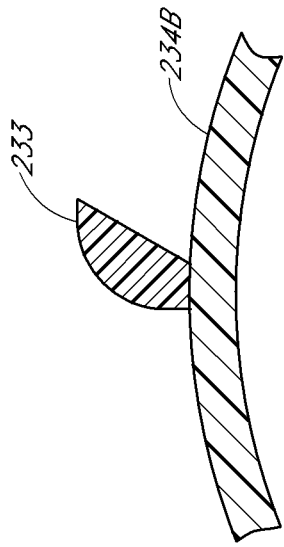
FIGS. 13A-13C illustrate various embodiments of scraping edges of a removal member of an endotracheal tube cleaning device.
Figure 13B:
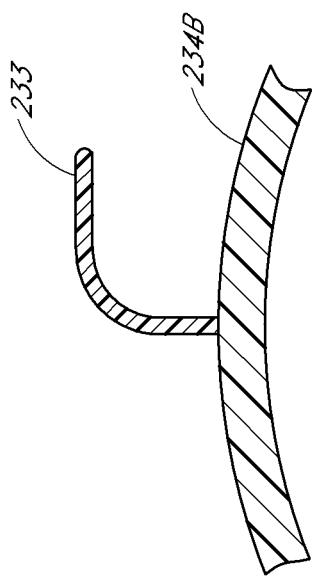
Figure 13C:
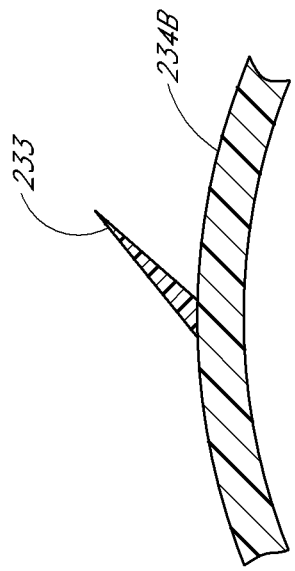

For example, the cleaning member 226A can include a round or half-circle O-ring 232A for removing the mucous and other easy-to-remove secretions deposited on the outer surface of the biofilm layer. The cleaning member 226B can include an O-ring 232B having a scraping edge 233 for removing the tenacious, more adherent, older biofilm deposits. With reference to FIGS. 13A-13C, various alternative embodiments of scraping edges 233 are illustrated. Other scraping edge profiles can be used without departing from the spirit and/or scope of the disclosure. Referring back to FIG. 12, the cleaning member 226C can include a round, half-circle, or quarter-circle O-ring 232C configured to remove and collect any remaining biofilm. As described above, the O-ring removal members 232 can be constructed of more than one material to enhance the scraping or wiping action of the O-rings. The O-rings 232 of the cleaning members 226 can have any of the cross-sectional profiles illustrated in FIGS. 10A-10H or any other cross-sectional profiles as desired and/or required.

Each of the cleaning members 226 can include a collection member 234 (e.g., braided or mesh scaffold) for collecting biofilm while still allowing sufficient airflow through the endotracheal tube 100. The multiple cleaning members 226 can be separated by a non-expandable attachment device or method, such as, for example, a heat shrink clamp band, sutures, adhesives, epoxy, welding, other low-profile mechanical attachment methods or devices, and/or the like. For example, as shown in FIG. 12, the multiple cleaning members 226 are separated by clamp bands 235 that constrain the expansion of the mesh collection members but are not attached to the inner shaft 128, thereby allowing for simultaneous deployment of the multiple cleaning members 226.

4. Separate Collection Member

Figure 14:
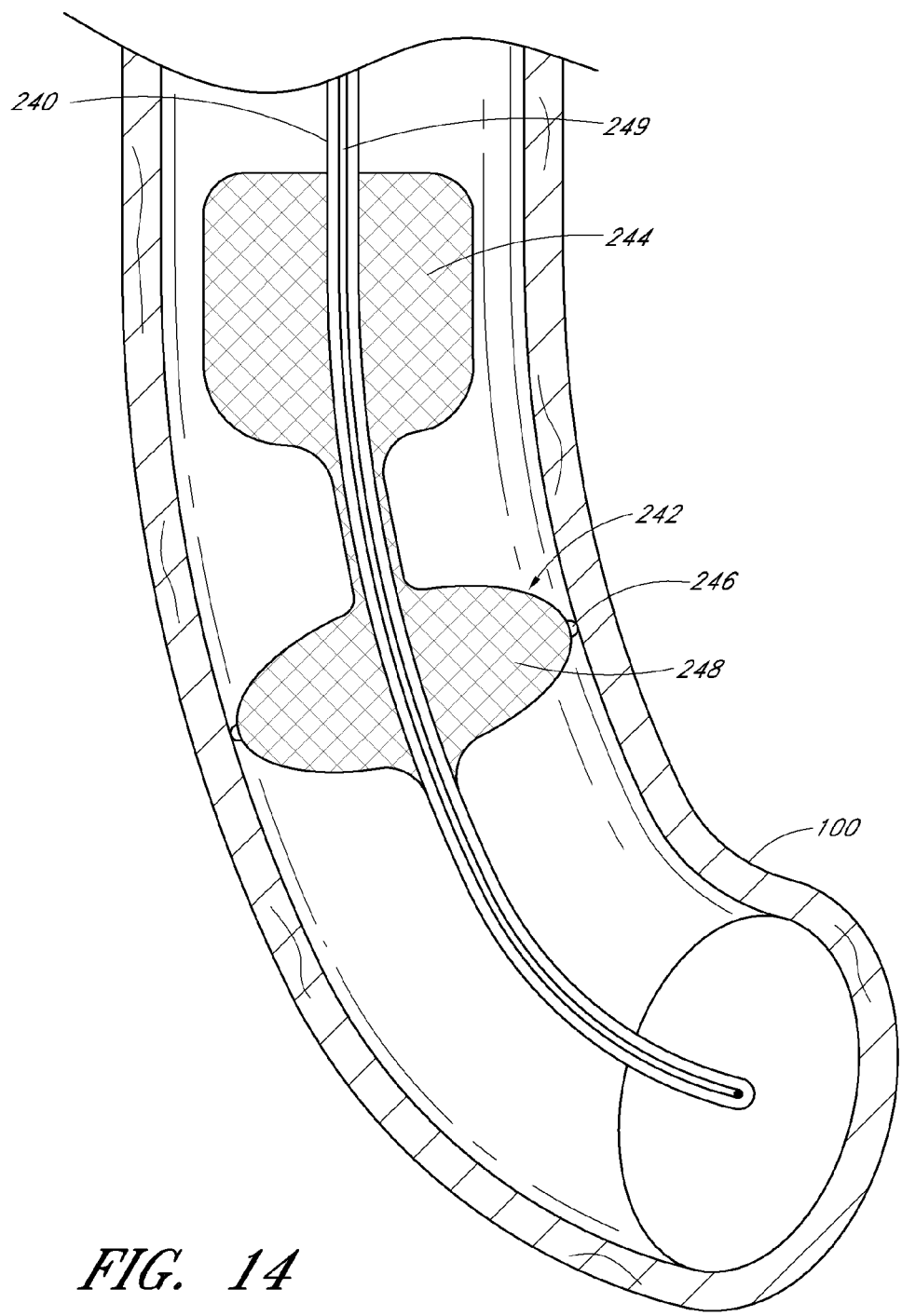
FIG. 14 illustrates an embodiment of an endotracheal tube cleaning device.

FIG. 14 illustrates another embodiment of an endotracheal tube cleaning device 240. The endotracheal tube cleaning device 240 includes a removal member 242 and a collection member 244. The removal member 242 includes an O-ring wiper 246 and a scaffold 248 (e.g., mesh scaffold) for selectively effectuating deployment of the O-ring wiper 246. In the depicted embodiment, the collection member 244 comprises a biofilm collection basket. The collection member 244 can be spaced proximally from the removal member 242 at a distance ranging from about 0.1 inches to about 0.5 inches; however other separation distances can be used as desired and/or required.

The collection member 244 can comprise a mesh or other porous material having openings that are small enough to collect solid or semi-solid biofilm deposits but large enough to allow for sufficient airflow through the collection member. In some embodiments, the maximum cross-sectional dimension of the openings ranges from about 0.010 inches to about 0.050 inches. The collection member 244 can be sized and shaped to hold up to about 20 ccs of biofilm. The collection member 244 can advantageously have a width or diameter that is less than the diameter of the endotracheal tube 100 so as not to contact the inner wall of the endotracheal tube 100. As shown in FIG. 14, the endotracheal tube cleaning device 240 can include an internal channel 249 for insertion of scopes (e.g., a visualization scope), catheters, probes, and/or other instruments, as described in greater detail herein. The endotracheal tube cleaning device 240 can include an inner shaft and outer shaft, as well as other structural features not shown in FIG. 14, but described with respect to the other embodiments herein.

III. Mechanical Expansion

As described above, according to some embodiments, the cleaning member 126 can be configured to transition from a collapsed configuration (see FIG. 3D) to an expanded configuration (see FIG. 3E) by the relative movement of inner and outer members (e.g., inner shaft 128 and outer shaft 129). In some embodiments, the inner member moves axially while the outer member remains stationary. In other embodiments, the outer member moves axially while the inner member remains stationary. In yet other embodiments, the inner and outer members are both configured to move axially.

A. Mechanical Struts

Figure 15A:
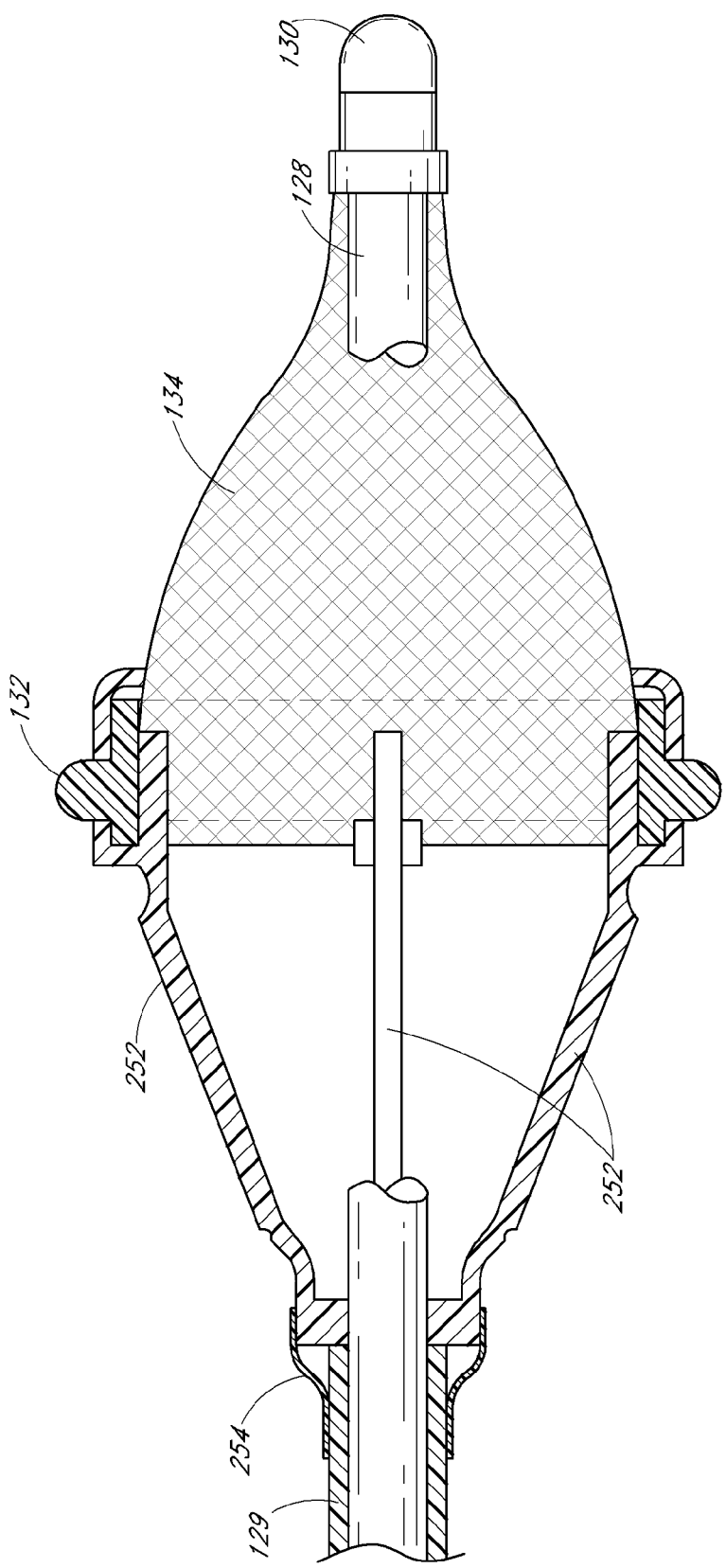
FIG. 15A illustrates a "fish-net" embodiment of a cleaning member of an endotracheal tube cleaning device.

In some embodiments, the cleaning member 126 can be mechanically expanded by multiple deploying struts. FIG. 15A illustrates a "fish-net" embodiment of the collection member 134. The proximal section of the collection member 134 comprises multiple "umbrella-like" deploying struts 252 to effectuate radial expansion of the removal member 132 and the distal section of the collection member 134 comprises a mesh scaffold, or collection basket, constructed to collect and trap biofilm removed by the removal member 132. The deploying struts 252 can be coined to provide flexibility for a desired expansion angle. The expansion angle can range from about 5 degrees to about 45 degrees or from about 20 degrees to about 35 degrees. As shown, the deploying struts 252 can extend from the outer shaft 129 to the removal member 132. The deploying struts 252 can be mechanically coupled and/or adhered to the outer shaft 129 and the removal member 132 by any suitable coupling and/or adhesive device or method, such as interference fits, ultrasonic welding, heat shrink tubing, adhesive, epoxy, other low-profile mechanical attachment means, and/or the like. As shown, the deploying struts 252 are coupled to the outer shaft 129 by a heat shrink band clamp 254. The deploying struts 252 can comprise one or more metallic and/or plastic materials. Nitinol may be used in several embodiments to form expanding components, such as the struts, scaffold, removal member, etc.

Figure 15B:
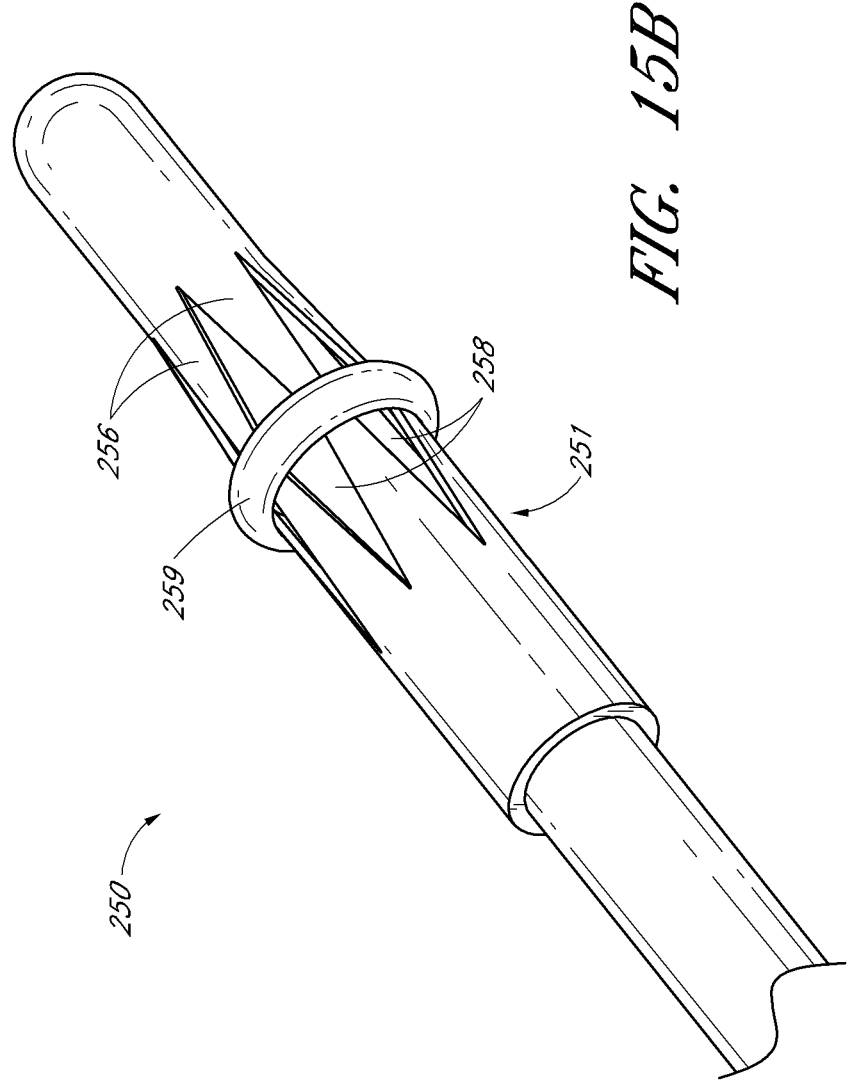
FIGS. 15B and 15C illustrate another embodiment of an endotracheal tube cleaning device comprising deployment struts for mechanical expansion of a cleaning member.
Figure 15C:
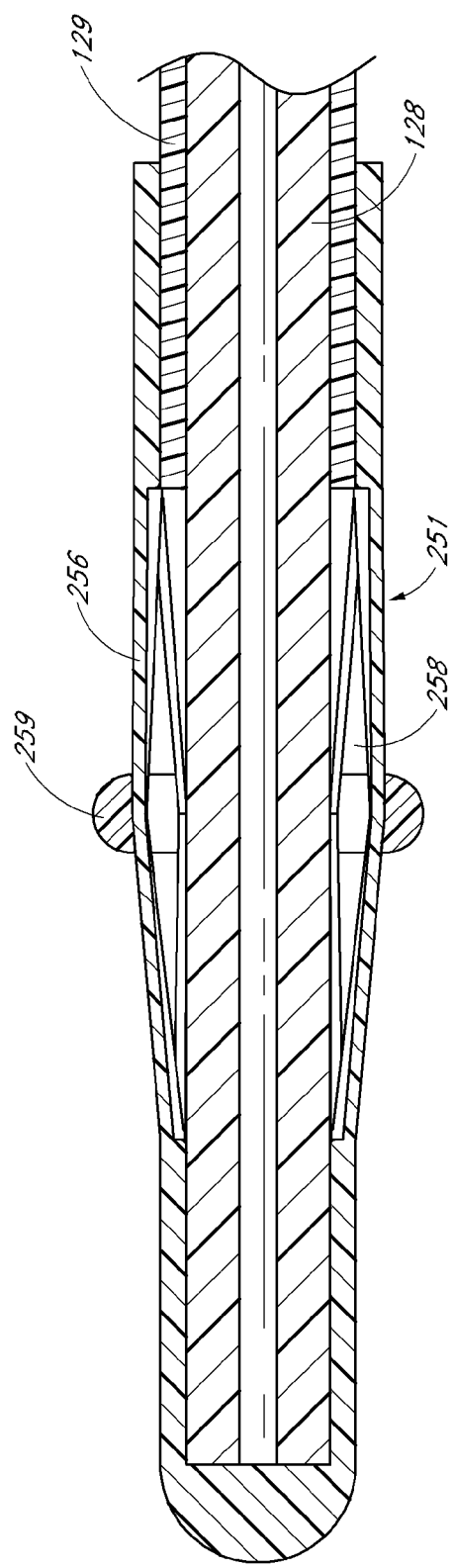

FIGS. 15B and 15C illustrate another embodiment of a "living hinge" endotracheal tube cleaning device 250 comprising deployment struts for mechanical expansion of a cleaning member 251. The cleaning member 251 illustrated in FIGS. 15B and 15C comprises a scaffold having deployment struts 256 and longitudinal slits 258 and an O-ring wiper 259. In some embodiments, the distal tip 130 of the endotracheal tube cleaning device 120 is integrally formed with distal end of the cleaning member 251. The distal tip 130 of the endotracheal tube cleaning device 120 can be coupled to the inner shaft 128 and the proximal end of the cleaning member 251 can be coupled to the outer shaft 129 by any suitable coupling and/or adhesive device or method, such as interference fits, ultrasonic welding, heat shrink tubing, adhesive, epoxy, other low-profile mechanical attachment means, and/or the like. In some embodiments, the connections between the distal end of the cleaning member 241 and the distal tip 130 or inner sheath 128 and/or the connection between the proximal end of the cleaning member 241 and the outer sheath 129 form living hinges about which the deployment struts expand. The O-ring wiper 259 can be coupled and/or adhered to the deploying struts 258 by overmolding, interference fits, ultrasonic welding, adhesive, sutures, epoxy, other low-profile mechanical attachment means, and/or the like. In some embodiments, movement of the inner shaft in a proximal direction causes the deploying struts 258 to flex or bend outward, thereby radially expanding the O-ring wiper 259. The deploying struts can comprise a substantially rigid elastomeric material to prevent collapse due to the return force of the O-ring wiper 259.

B. Expanding Collet Assemblies

Figure 16A:
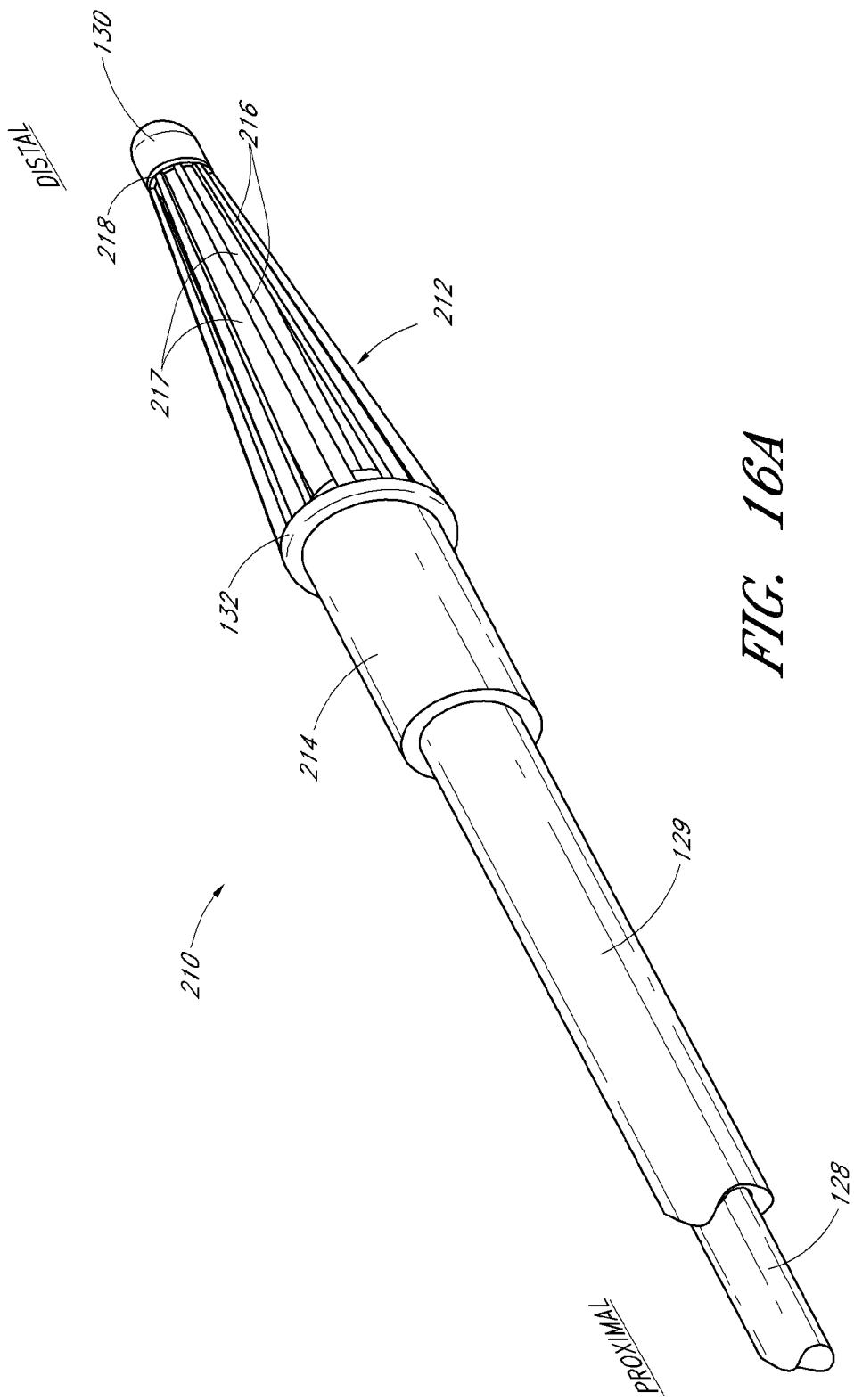
FIGS. 16A-16D illustrate various embodiments of mechanisms for mechanical expansion of a cleaning member of an endotracheal tube cleaning device.
Figure 16B:
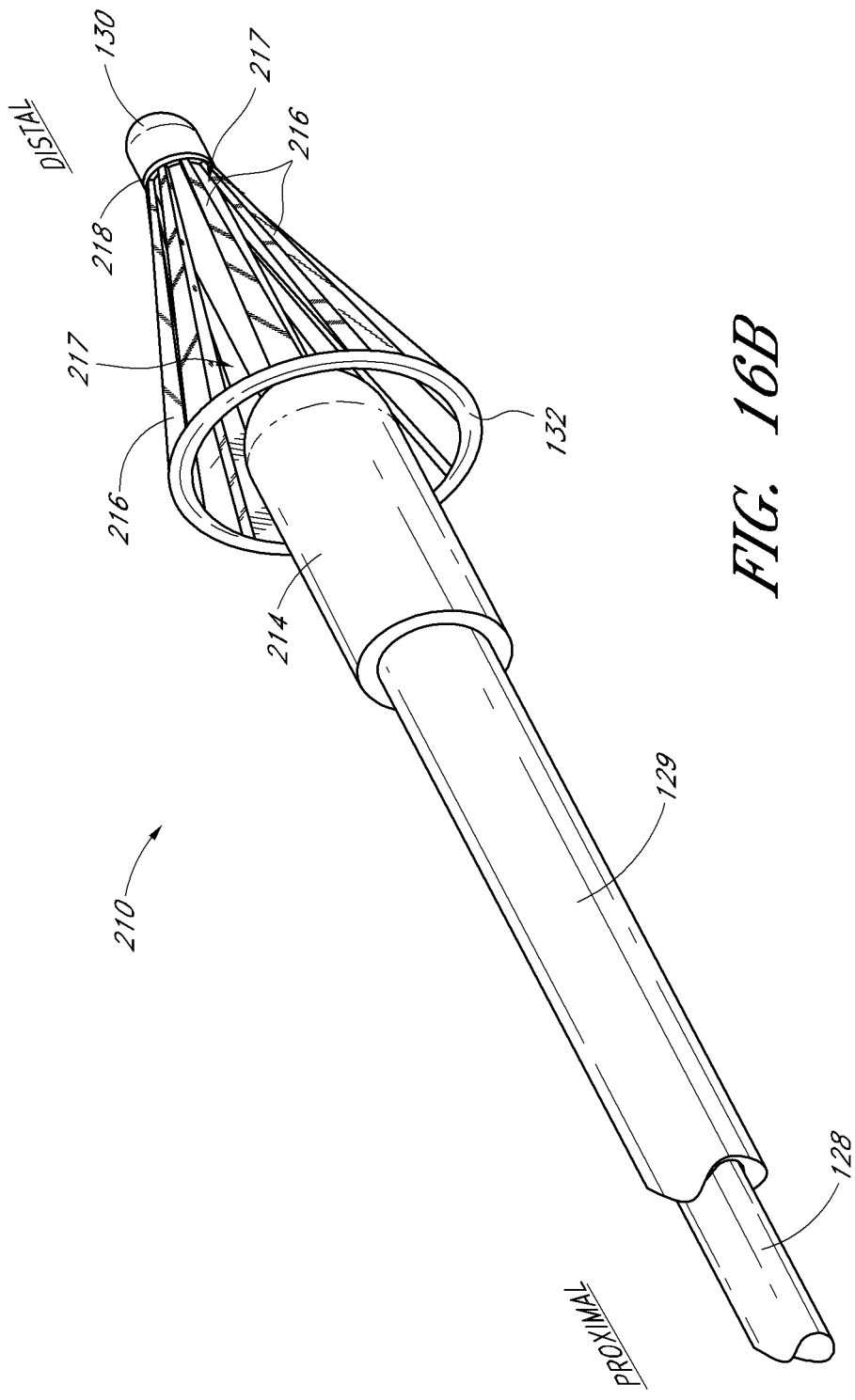

FIG. 16A-16D illustrate other mechanisms for mechanical expansion of a removal member (e.g., an O-ring) of an endotracheal tube cleaning device. FIGS. 16A and 16B illustrate an embodiment of a collet expansion assembly 210 in an unexpanded and expanded configuration, respectively. The collet expansion assembly 210 includes an expanding collet 212 that can be radially expanded by a ram 214.

The expandable collet 212 can comprise elastomeric material, such as polypropylene, polyethylene, nylon, polycarbonate, and/or the like. The elastomeric material can advantageously provide living hinge capability. The expandable collet 212 comprises multiple (e.g., four or more) struts, or leaves, 216 and multiple longitudinal openings, or slits, 217 to allow for radial expansion.

The ram 214 can be fixedly attached to the outer shaft 129, thereby remaining stationary. The ram 214 can have a circular, substantially circular, elliptical and/or other shaped cross section. The ram 214 can have a uniform cross-sectional diameter across its length or a varying cross-sectional diameter. The distal end of the ram 214 can have a tapered edge so as to reduce the likelihood that the expandable collet 212 is snagged on the ram 214. The distal end of the expandable collet 212 can be connected to and/or can be integral with the distal tip 130 of the endotracheal tube cleaning device and the inner sheath 128 can be connected to the distal tip 130.

As the inner shaft 128 is pulled proximally, the expandable collet 212 can be pulled toward the ram 214. As the inner surface of the struts 216 engage and move over the ram 214, they can be expanded radially by the ram 214 about living hinges 218 formed between the distal ends of the struts 216 and the distal tip 130. As the struts 216 of the expandable collet 212 expand, the removal member 132 can also expand. FIG. 16B illustrates the collet expansion assembly 210 in an expanded position. As shown in FIG. 16B, upon expansion, the open proximal side of the expandable collet 212 can function as a collector of biofilm as the endotracheal tube cleaning device is withdrawn from the endotracheal tube. In some embodiments, a mesh or other porous material can be coupled to the expandable collet 212 to facilitate collection of biofilm while still allowing airflow through the endotracheal tube cleaning device. In other embodiments, the ram 214 can move with respect to the expandable collet 212.

The removal member 132 can be overmolded, applicated, assembled, adhered, and/or otherwise coupled to the expandable collet 212. In some embodiments, the removal member 132 sits within a circumferential groove of the expandable collet 212. The removal member 212 can be an O-ring comprised of TPE, silicone, urethane, ethylene-vinyl acetate (EVA), polyisoprene, a KRATON polymer, and/or the like. The durometer of the O-ring can range from about 30 Shore A to about 90 Shore A. In other embodiments, the removal member 132 is not included.

Figure 16C:
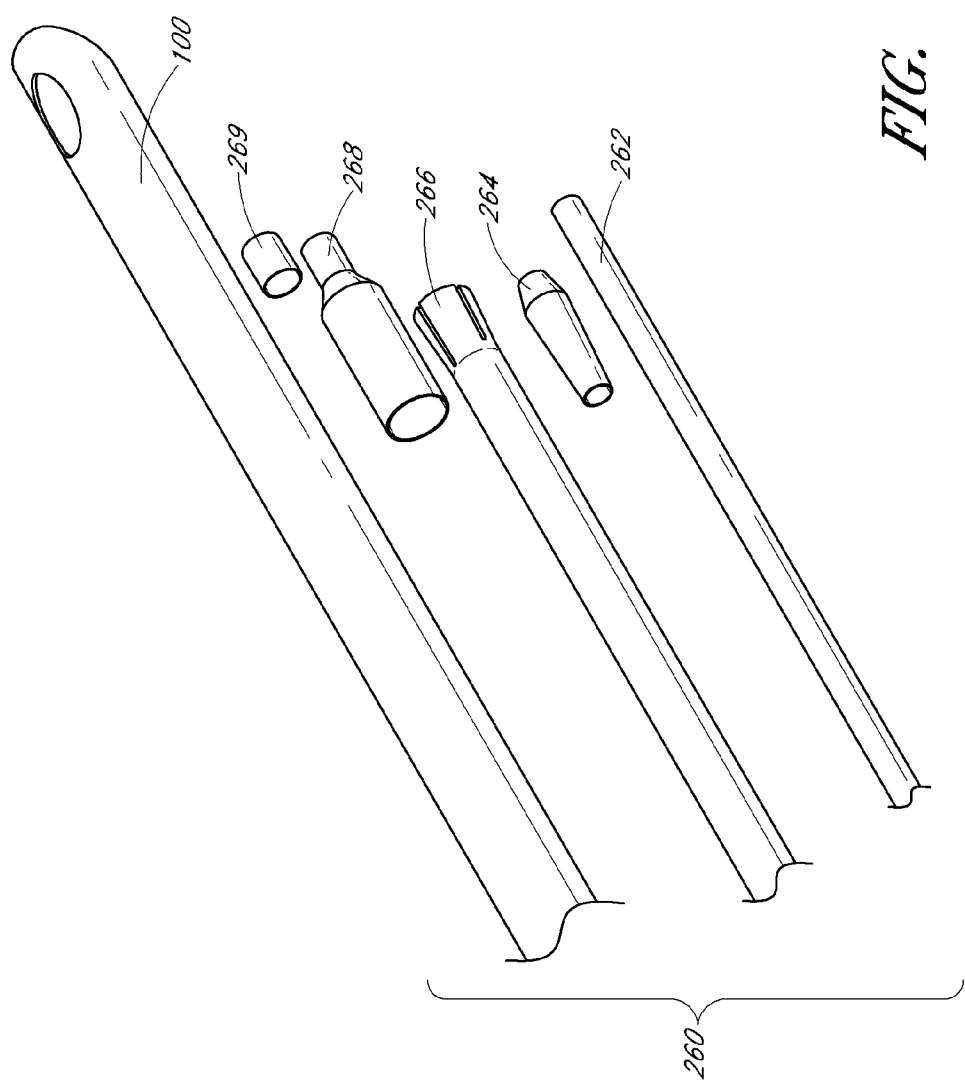
Figure 16D:
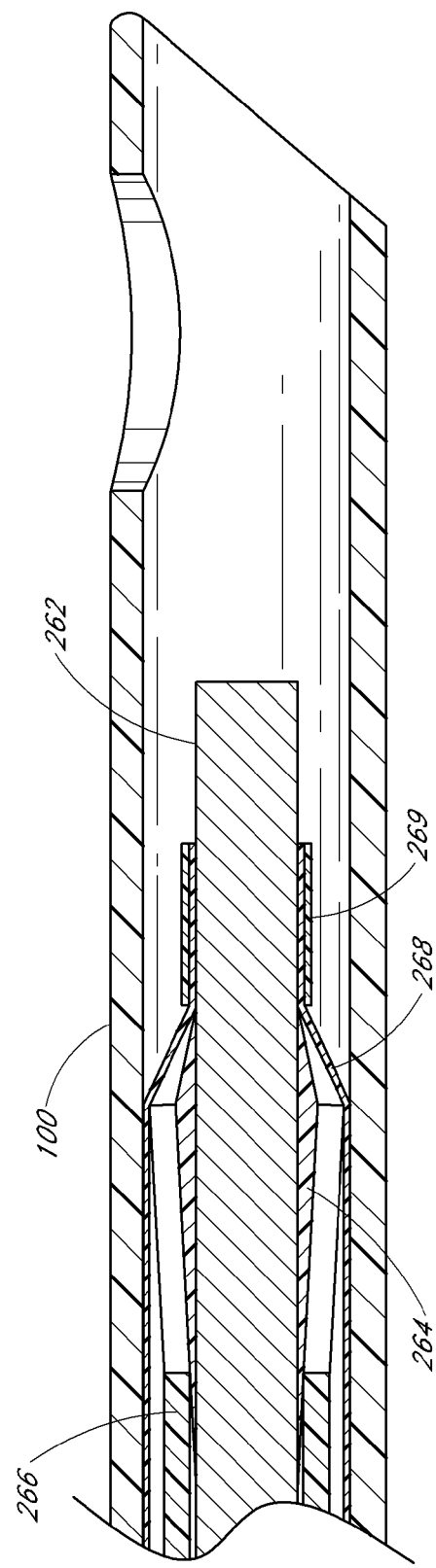

FIG. 16C illustrates a collet expansion assembly 260 of an embodiment of the endotracheal tube cleaning device 120 and the endotracheal tube 100. In the depicted embodiment, the collet expansion assembly 260 includes a center rod 262, a molded collet 264, a split tubing 266, an expanding netting 268, and a molded adhesion band 269. FIG. 16D illustrates the assembled collet expansion assembly 260 in its expanded configuration within the endotracheal tube 100. In some embodiments, the center rod 262 replaces the inner shaft 128, the split tubing 266 replaces the outer shaft 129, and the expanding netting 268 replaces the collection member 134. As shown in FIG. 16D, the molded collet 264 is inserted over and attached to the center rod 262, which in turn is inserted within the split tubing 266, the expanding netting 268 is placed over the split tubing 266, and the molded adhesion band 269 is overmolded on the distal end of the expanding netting 268. The expanding netting 268 can be connected to the center rod 262 by the molded adhesion band 269. As the center rod 262 moves proximally, the increasing diameter of the molded collet 264 causes the split tubing 266 to expand radially, thereby bringing the expanding netting 268 into contact with the inner wall of the endotracheal tube. As the center rod 262 is withdrawn, biofilm removed by the expanding netting 268 can collect within the expanding netting 268, similar to the collection members described herein.

C. Vented Tube Design

Figure 17B:
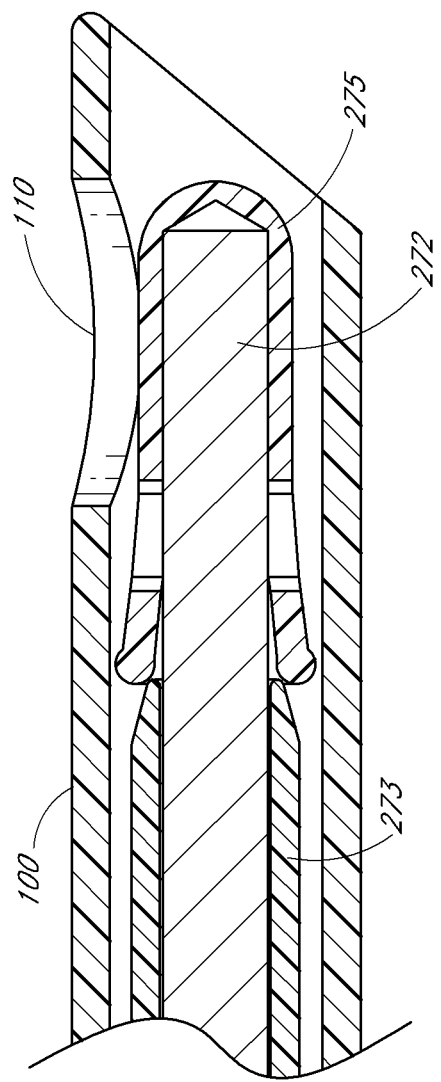

FIGS. 17A and 17B illustrate an embodiment of a vented tube assembly 270. The vented tube assembly 270 includes a center rod 272, a vented tube 273, and a vented tip 275. As shown in FIG. 17B, the center rod 272 is inserted within the vented tube 273. The vented tip 275 can be attached to the distal end of the center rod 272. The distal tip of the vented tube 273 can be tapered such that when the center rod 272 is moved proximally with respect to the vented tube 273, the rounded proximal edge of the vented tip 275 slides over the tapered distal tip of the vented tube 273, and expands radially with the increasing diameter of the vented tube 273. The vents in the vented tube 273 can allow the vented tube 273 to expand. In some embodiments, the proximal edge of the vented tube 273 comprises a circumferential ridge or protrusion configured to engage the inner surface of the endotracheal tube 100 and to remove biofilm deposited thereon as the center rod 272 is withdrawn from the endotracheal tube 100. In other embodiments, an O-ring can be overmolded or otherwise coupled about the circumference of the vented tube 273.

In some embodiments, the vented tip 275 can be expanded by infusion of air and/or liquid through the vented tube 273. In some embodiments, therapeutic agents, drugs, and/or gases can be delivered through the vented tip 275 and/or biofilm can be aspirated out of the endotracheal tube 100 through the vented tube 273. The vented tip 275 can comprise one or more durable elastomeric materials, such as silicone, urethane, polypropylene, polyethylene, and/or the like.

D. Helical Spring Assembly

Figure 18A:
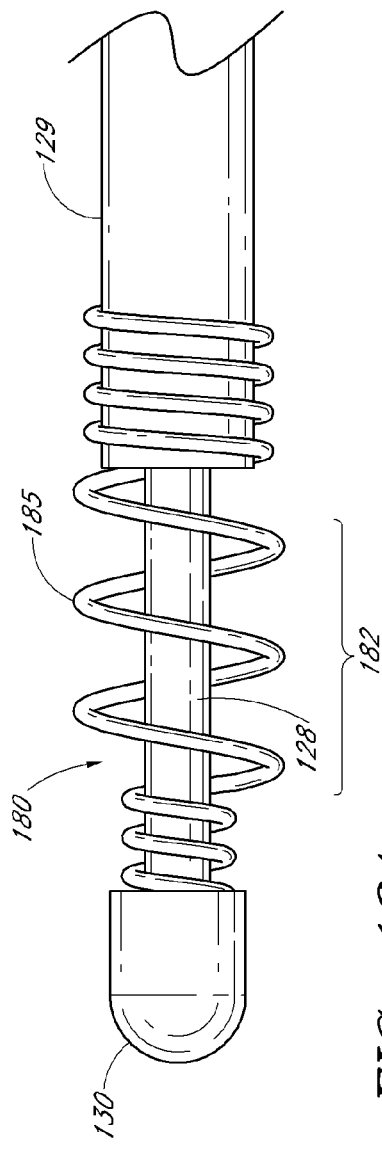
FIGS. 18A-18C illustrate various embodiments of a helical spring wireform for mechanical expansion of the cleaning member of an endotracheal tube cleaning device.
Figure 18C:
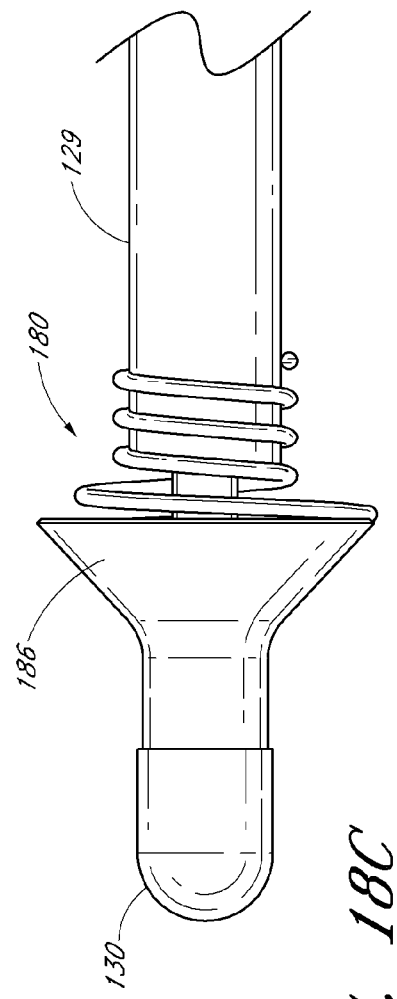
Figure 18B:
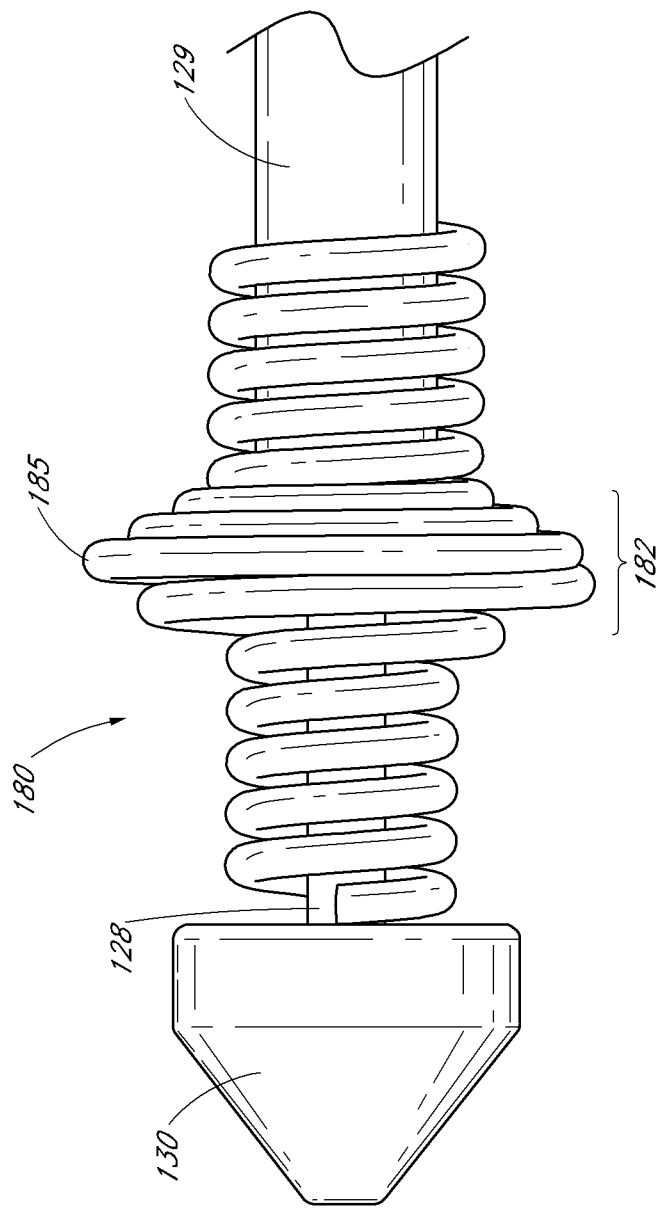

FIGS. 18A-18C illustrate other embodiments of mechanical expansion mechanisms using helical springs. With reference to the embodiments illustrated in FIG. 18A-18C, the distal end of the helical spring wireform 180 is attached to the inner sheath 128 and the proximal end of the helical spring wireform is attached to the outer sheath 129. The helical spring wireform 180 can be attached to the inner sheath 128 and the outer sheath 129 by any suitable attachment method or device, such as, for example, heat shrink tubing, adhesive, epoxy, interference fits, other low-profile mechanical attachment methods and/or the like.

In some embodiments, as shown in FIG. 18A, the helical spring wireform 180 is wound or otherwise manufactured such that the middle portion 182 comprises a slightly unstable, naturally unfurled configuration. When the inner shaft 128 is engaged by the trigger 152 (thereby moving the inner sheath 128 in a proximal direction, the inner sheath 128 compresses or draws the helical spring wireform 180 proximally, and the middle portion 182 is distended radially. In other embodiments, as shown in FIG. 18B, the helical spring wireform 180 is wound or otherwise manufactured such that the middle portion 182 comprises a naturally distended configuration. Before insertion of the endotracheal tube cleaning device of FIG. 18B, the actuation assembly 124 can be configured to move the outer sheath 129 proximally to draw the middle portion 182 of the helical spring wireform 180 to an unfurled configuration. Once the middle portion 182 has been properly positioned within the endotracheal tube, the trigger 152 can be released to return the middle portion 182 to its distended configuration for engaging the inner surface of the endotracheal tube 100.

The helical springs 180 of FIGS. 18A-18C can comprise one or more metallic and/or plastic materials, such as, for example, stainless steel, spring steel, Nitinol, injection-molded polycarbonate and/or any other injection-molded plastic material that is capable of retaining spring qualities. In some embodiments, the diameter of the spring wire can range from about 0.001 inches to about 0.05 inches in diameter, or from about 0.005 inches to about 0.025 inches in diameter. The middle portion 182 can comprise from about 1 to about 3 turns (e.g., 1⅛ to about 1¾ turns). In some embodiments, at least the outermost loop 185 of the distended middle portion 182 is coated with plastisol, silicone, other suitable elastomers, and/or the like, to aid in wiping and collecting biofilm as the endotracheal tube cleaning device 120 is withdrawn from the endotracheal tube 100.

In some embodiments, as illustrated in FIG. 18C, a thin, flexible funnel 186 extends from the distal end of the inner shaft 128 or the distal tip 130 of the endotracheal tube cleaning device 120 to the middle spring 185 of the middle portion 182 of the helical spring wireform 180. The funnel 186 can advantageously serve as a collector of biofilm when the endotracheal tube device 120 is withdrawn from the endotracheal tube 100. The funnel 186 can be attached to the inner shaft 128 or the distal tip 130 and to the helical spring wireform 180 by any suitable attachment method or device, such as, for example, heat shrink tubing, adhesive, wound wire, suture, epoxy, other low-profile mechanical attachment method or device, and/or the like. The funnel can be attached to the helical spring wireform 180 continuously or intermittently (e.g., at selected attachment locations) using any attachment method or device, such as adhesive, flexibly epoxy, sutures, and/or the like. The funnel 186 can comprise latex, thin braid material, silicone, and/or other elastomeric or polymeric materials, flaccid materials and/or the like. The funnel can be draped over the helical spring wireform 180 with enough spare material to allow for expansion of the helical spring to the distended configuration without substantially retarding or otherwise hindering deployment of the helical spring. In other embodiments, the helical spring 180 can serve as its own collector without the funnel 186.

E. Self-Expanding

In some embodiments, the collection member 126 can include one or more "self-expanding" materials that are configured to radially expand when a compressive force is exerted upon the materials in a longitudinal direction by the movement of the inner shaft 128. The radial expansion of the collection member 126 causes the radial expansion of the removal member 132. The term "self-expanding" as used herein shall be given its ordinary meaning and shall mean, without limitation, that no additional mechanical structure (such as struts, collets, springs, pistons, and/or the like) other than the physical characteristics or properties of the materials of the collection member (e.g., scaffold), is used to expand the collection member. For example, self-expanding materials can simply expand with the relative movement of the inner shaft 128 with respect to the outer shaft 129. In some embodiments, self-expanding materials comprise Nitinol, other shape-memory metals, alloys or other materials and/or the like.

Figure 19B:
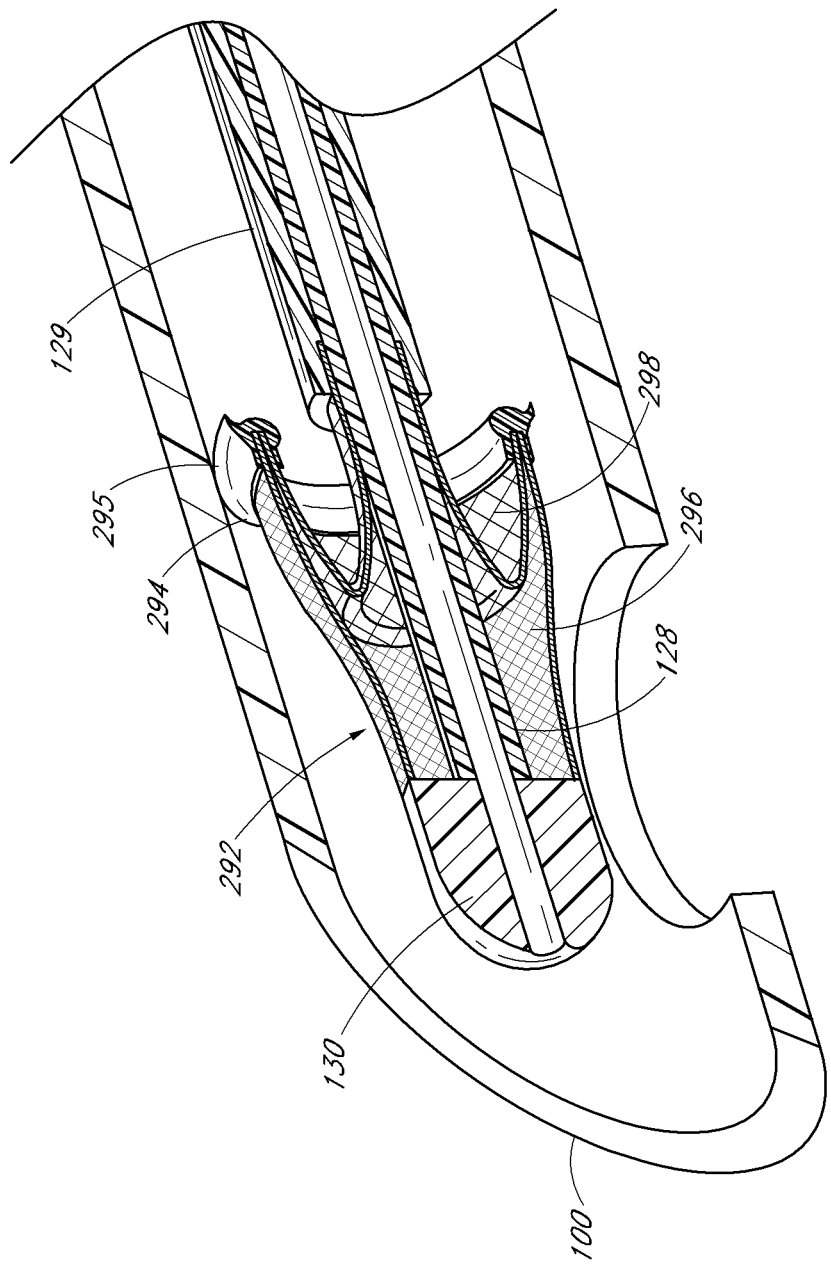

FIGS. 19A and 19B illustrate another embodiment of a mechanically-expandable cleaning member 290. FIG. 19A illustrates a perspective view of the mechanically-expandable cleaning member 290 and FIG. 19B illustrates a cross-sectional view of the mechanically-expandable cleaning member 290. FIGS. 19A and 19B illustrate the mechanically-expandable cleaning member 290 in the expanded configuration. As shown, the cleaning member 290 can include an expandable collection member or scaffold 292 and a removal member 294 having an angled rim 295 for contacting the internal surface of the endotracheal tube 100. The angled rim 295 can be angled about 2 to about 40 degrees (e.g., 5 to 25 degrees) from a vertical orientation.

The expandable collection member 292 can comprise an outer scaffold member 296 and an inner scaffold member 298. In the depicted embodiment, the inner scaffold member is folded in on itself and forms a hinge about which it expands. In the depicted embodiment, the distal end of the outer scaffold member 296 is connected to the distal tip 130 of the endotracheal tube cleaning device 120. The distal end of the outer scaffold member 296 can be connected to the distal tip 130 using heat shrink tubing, an interference fit, other fasteners, or other suitable low-profile mechanical devices and/or any other attachment method or device. The inner sheath 128 can be assembled to or be formed integral with the distal tip 130. Likewise, a first end of the inner scaffold member 298 can be connected to the distal end of the outer shaft 129 using any attachment device or method, including, for example, an interference fit, heat shrink tubing, adhesive, epoxy, molding, welding and/or the like. The second end of the inner scaffold member 298 and the proximal end of the outer scaffold member 296 can be connected to the removal member using any attachment device or method, including, for example, an interference fit, heat shrink tubing, adhesive, epoxy, molding, welding and/or the like.

With continued reference to the embodiment illustrated in FIGS. 19A and 19B, when the inner shaft 128 is pulled back (i.e., moved proximally with respect to the outer shaft 129), a force can be exerted on the outer scaffold member 296 by the inner shaft 128 and the inner scaffold member 298 that causes the angled rim 295 of the removal member 294 to distend radially against the inner wall of the endotracheal tube 100. In some embodiments, the inner scaffold member 298 of the expandable collection member 292 can also exert a radial expansion force on the removal member 294 as the inner sheath 128 moves in a proximal direction. The expandable collection member 292 includes a collection area within the interior of the outer scaffold member 296 and/or the inner scaffold member 298 for collection of biofilm as the endotracheal tube cleaning device 120 is withdrawn from the endotracheal tube. The scaffold of the expandable collection member 292 can comprise one or more braid materials, elastomeric or polymeric materials, such as, for example, polyisoprene, TPE, silicone, urethane, and/or any other suitable material that has the desired or required softness and/or other characteristics (e.g., a softness of about 15 to about 40 Shore A durometer). The inner scaffold member 298 of the expandable collection member 292 can comprise strengthening materials to provide sufficient rigidity (e.g., larger diameter braided fibers or stiff porous elastomeric material).

The outer scaffold member 296 and the inner scaffold member 298 can be configured to have varying porosity to facilitate expansion and/or collection of biofilm. For example, in embodiments where braided material is used for the expandable collection member 292, a lower pick count (e.g., about 5 to about 10 picks per inch) can be used for the proximal side, while a higher pick count (e.g., about 10 to about 25 picks per inch) can be used for the distal side. In some embodiments, the diameters (or other cross-sectional dimensions) of the braid fibers vary from about 0.005 inches to about 0.010 inches. However, in alternative embodiments, such diameters or other cross-sectional dimension is less than about 0.005 inches or greater than 0.010 inches, as desired or required. In some embodiments, the expandable collection member 292 comprises two or more layers of braid material. In some embodiments, the proximal portion and the distal portion of the braided collection member 292 can be ultrasonically welded or otherwise attached to form a regular smooth continuous rim and the removal member 294 is not included.

In embodiments where elastomeric material is used for the expandable collection member 292, the expandable collection member 292 can be molded in a transfer press, an injection molding press, a compression molding press, a thermoforming press and/or using any other manufacturing device, system or method.

IV. Alternate Modes of Expansion

In some embodiments, the collection member 134 (e.g., scaffold) can comprise one or more shape memory materials that automatically expand from a compressed configuration maintained during insertion of the endotracheal tube cleaning device 120 by a sheath to an expanded configuration when the sheath is withdrawn or the collection member 134 is pushed out of the sheath. The shape memory material can include nickel titanium alloys and/or other shape memory materials. In some embodiments, the shape memory material can be temperature-activated, light-activated, and/or activated by liquid.

In other embodiments, the collection member 134 can be expanded using inflation. For example, the removal member 132 can comprise an inflatable O-ring, which when inflated, causes the collection member 134 to expand. The inflatable O-ring can be on the inside of the collection member 134 (e.g., similar to an innertube) or on the outside of the collection member 134. In some embodiments, an inflatable balloon or other member is configured to selectively expand the cleaning member 126 and/or any other portion of the cleaning device. In one embodiment, the removal member comprises a smooth or textured inflatable balloon or bladder.

V. Controlled Expansion

In some embodiments, the endotracheal tube cleaning device 120 can provide for variable expansion of the cleaning member 126, depending on the tube's inside diameter, the amount of biofilm deposited on the internal surface of the endotracheal tube 100 and/or one or more other factors or considerations. In other embodiments, the endotracheal tube cleaning device 120 can selectively deploy the cleaning member 126 with variable pressure depending on the endotracheal tube's inside diameter, the amount of biofilm deposited on the internal surface of the endotracheal tube 100 and/or one or more other factors or considerations. In some embodiments, the actuation assembly 124 is configured to expand the cleaning member 126 about 0.1 mm to about 2 mm larger than the inside diameter of the endotracheal tube (e.g., from about 0.1 mm to about 1 mm, about 0.5 mm to about 1.5 mm, about 1 mm to about 2 mm, and overlapping ranges thereof).

Figure 20:
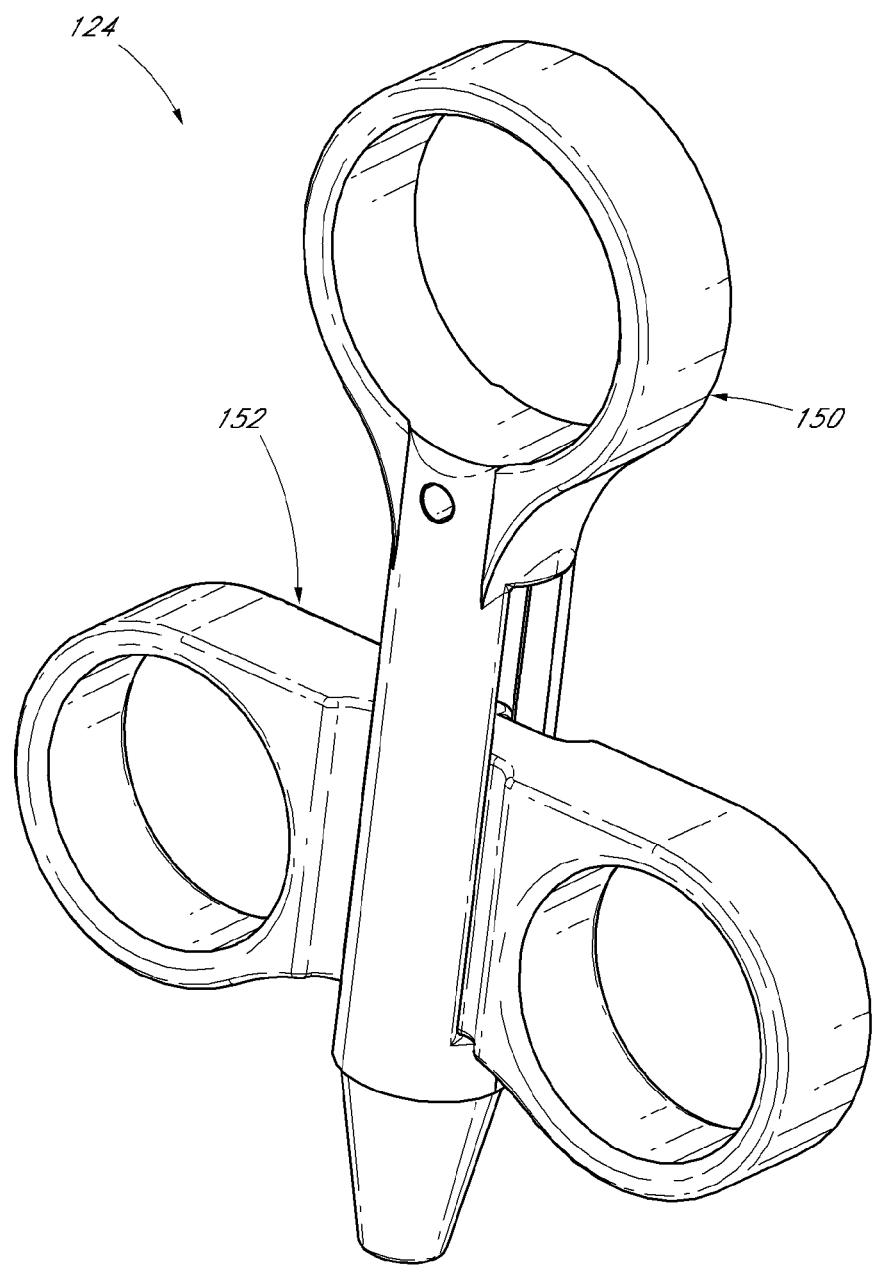
FIG. 20 illustrates a perspective view of an actuation assembly of an endotracheal tube cleaning device.
Figure 21A:
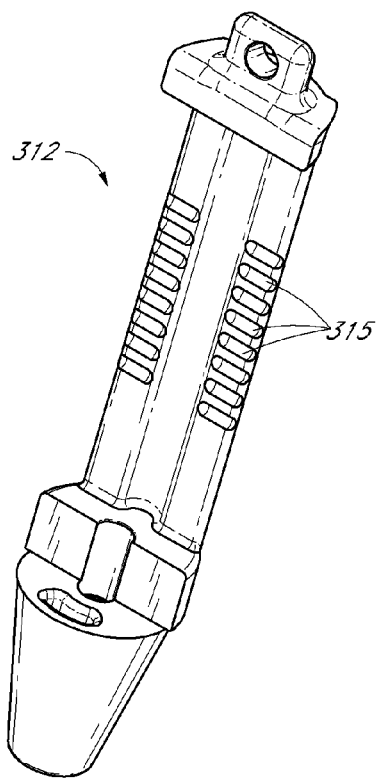
FIGS. 21A-21D illustrate perspective views of the components of the actuation assembly of FIG. 20.
Figure 21B:
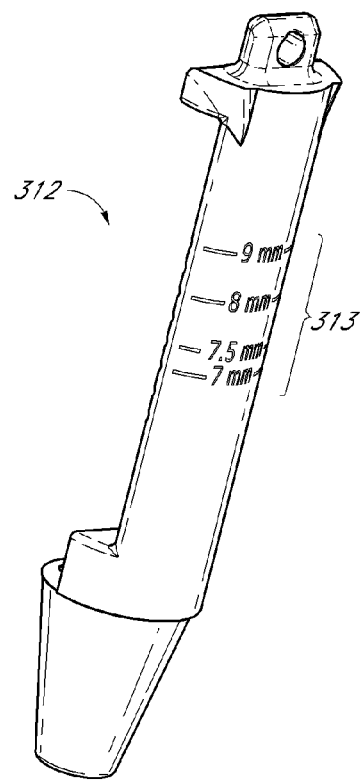
Figure 21C:
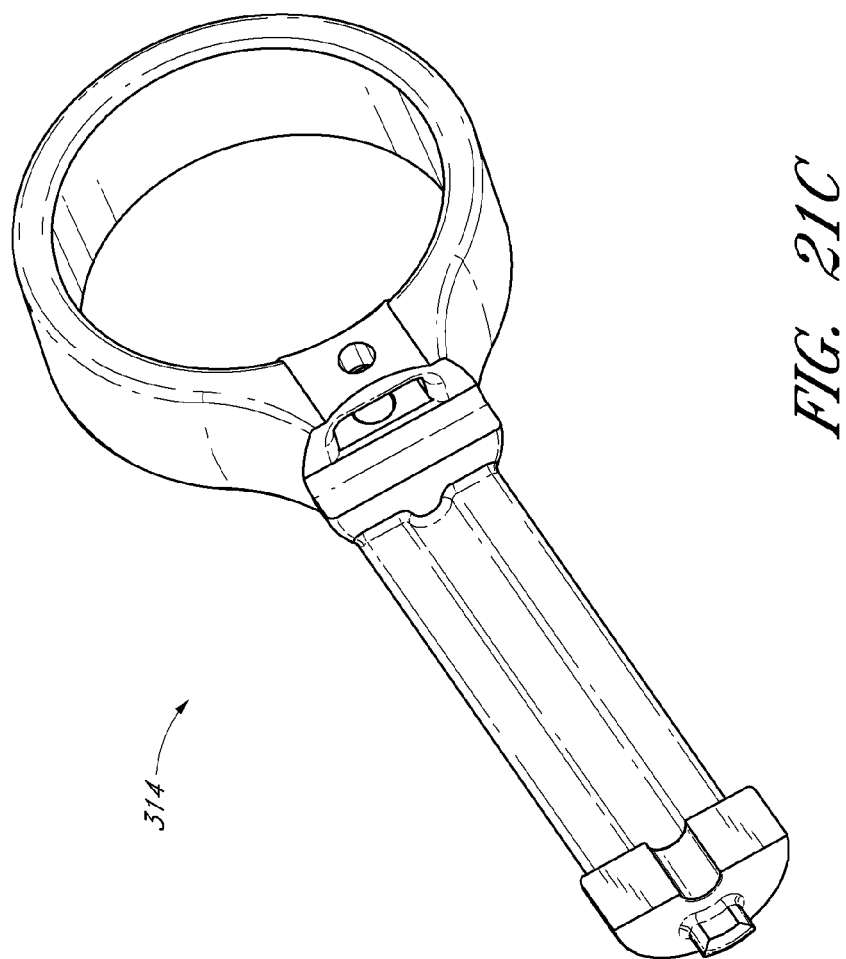

In some embodiments, the actuation assembly 124 includes features that provide for incremental expansion of the cleaning member 126. FIG. 20 illustrates an assembled actuation assembly 124 configured to provide controlled, incremental expansion of the cleaning member 126. FIGS. 21A-21D illustrate various perspective views of components of one embodiment of an actuation assembly 124. For example, FIGS. 21A and 21B illustrate a detent half 312 and FIG. 21C illustrates a thumb handle half 314 of the handle 150. As shown in FIG. 21A, the detent half 312 can include multiple detents 315 incrementally spaced along its length. The detents 315 can be formed as notches, slits, recesses, and/or the like within the molded material of the detent half 312. As shown in FIG. 21B, the detent half 312 can include visible markings or indicia 313. The visible markings can aid the clinician in setting the initial position of the trigger 152 with respect to the handle 150 depending on the diameter of the endotracheal tube to be cleaned. The visible markings 313 can also provide visible feedback to the clinician as to what diameter the cleaning member is currently expanded to. The visible markings can include color or pattern variations, text, varying line sizes or widths, numbers, and/or the like. In some embodiments, the visible markings provide tactile feedback to the clinician.

Figure 21D:
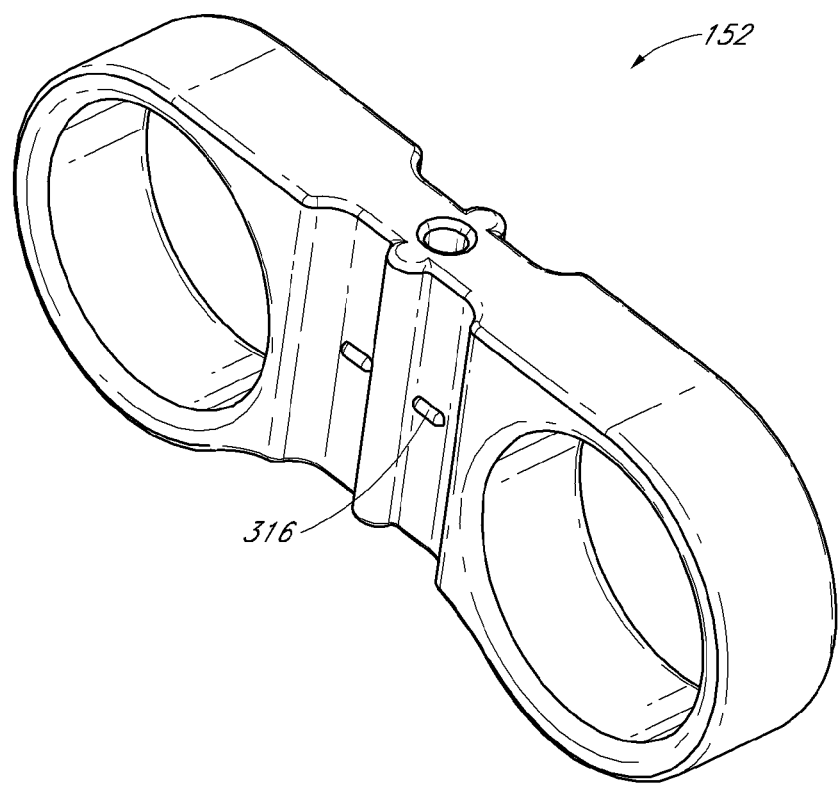

FIG. 21D illustrates one embodiment of a trigger 152 for an actuation assembly. As shown, the trigger 152 can include one or more bumps, ridges, projections 316 and/or the like. In some embodiments, the bump 316 is sized, shaped, or otherwise adapted to engage with, or be at least partially received by, the detents 315 of the handle 150. In some embodiments, the trigger 152 includes multiple bumps 316 or similar features. The trigger 152 can be captured by the assembly of the handle halves 312, 314. Further, the handle halves 312, 314 can be coupled to each other or otherwise assembled using adhesives, crush ribs, snap fit connections, other mechanical fasteners, ultrasonic welding, and/or any other suitable attachment method or device.

The detents 315 can serve to provide a hard stop and gauge for the size of the endotracheal tube being to be cleaned. Accordingly, a single cleaning device can be used to clean endotracheal tubes having any of a range of inner diameters. For example, and not by way of limitation, the detents 315 can allow for cleaning of endotracheal tubes having an inner diameter between about 5 mm and about 10 mm. In other embodiments, the detents 315 can permit for cleaning of endotracheal tubes (or any other medical or non-medical tube) with inner diameter below 5 mm or above 10 mm, as desired or required. The detents 315 can be spaced to provide for incremental expansion in 0.5 mm or 1 mm increments. However, any other incremental expansion may be used. Engaging the appropriate detent for each endotracheal tube size can advantageously allow for the appropriate amount of scaffold deployment based on the inner diameter of the endotracheal tube.

The detent and bump profiles can be modified for smooth operation and reentry. For example, the edges and tips of the detents 315 can be radiused such that the bumps 316 do not hang up or otherwise serve as an obstruction. In some embodiments, the edges and tips of the detents 315 are generally smooth in order to reduce friction. In some embodiments, the handle 150 can include visible indicia on the outside surface to indicate the correspondence between the detents 315 and the inner diameter dimensions. Accordingly, a clinician can make sure that the cleaning member 126 is appropriately expanded for the particular endotracheal tube being cleaned. In some embodiments, the radiusing of the detent tips and slight play in the trigger 152 allows for "fine tuning" of the expansion during removal of the endotracheal tube cleaning device 120.

In other embodiments, the actuation assembly 124 can be configured to provide for continuous expansion of the cleaning member 126, such as a rotatable thumbwheel assembly.

Under some circumstances, the failure to contact the biofilm or inside wall of the endotracheal tube with the appropriate pressure can potentially result in invagination or cavitation. Accordingly, in some embodiments, the endotracheal tube cleaning device 120 is configured to allow for manual fine tuning or adjustment of the expansion of the cleaning member 126. In some embodiments, the clinician can adjust the expansion of the cleaning member 126 based upon an actual or estimated biofilm thickness (e.g., maximum biofilm thickness, average biofilm thickness, etc.) within the endotracheal tube 100 and the known inner diameter of the endotracheal tube 100. For example, the estimated maximum biofilm thickness can be determined based on the endotracheal tube length, the inner diameter of the endotracheal tube, the reason for ventilation, one or more patient risk factors, the amount of biofilm removed at particular time intervals (e.g., 3, 8, 12, 24 hours, other time intervals, etc.).

In other embodiments, the clinician can adjust the expansion of the cleaning member based on, at least in part, a pressure sensor of the endotracheal tube cleaning device 120, tactile feedback, visualization of the biofilm using a visualization scope and/or one or more other factors or indicators.

In embodiments wherein a pressure sensor is used, the pressure sensor can be an electrical or nanotechnology sensor configured to sense the optimal pressure against the wall of the endotracheal tube 100. Thus, the clinician can selectively adjust the expansion of the cleaning member 126 based upon the measured pressure and/or one or more other inputs. In other embodiments, the pressure sensor can be connected to a feedback mechanism to provide for automatic adjustment (e.g., expansion or contraction) of the cleaning member.

In some embodiments that incorporate visualization, expansion of the cleaning member can be manually or automatically set or adjusted based on an analysis of the diameter of the endotracheal tube 100, the amount of biofilm 116 present in the endotracheal tube 100 and/or one or more other factors or considerations.

In some embodiments, the removal member 132 comprises one or more materials that automatically expand to independently apply pressure to the wall of the endotracheal tube, thereby providing automatic "fine-tuning" of the extent of expansion after a "rough" mechanical expansion of the actuation assembly 124 and the collection member 134.

VI. Depth Control

The endotracheal tube cleaning device 120 can include features configured to control the depth of insertion of the endotracheal tube cleaning device 120 within the endotracheal tube 100. In some embodiments, the endotracheal tube cleaning device 120 includes visible indicia along the length of the outer shaft 129 to indicate the depth of the endotracheal tube cleaning device 120 in the endotracheal tube 120. In some embodiments, a lockable, movable stop is coupled to the outer shaft 129 to prevent against over-insertion of the endotracheal tube cleaning device 120 beyond the distal tip 108 of the endotracheal tube 100. In other embodiments, the endotracheal tube cleaning device 120 includes a visualization channel or lumen in which a visualization scope can be inserted to determine the exact positioning of the endotracheal tube cleaning device 120 within the endotracheal tube 100. In still other embodiments, radiopaque markers can be used in combination with imaging modalities to determine the depth of insertion.

A. Mechanical Control

Figure 22:
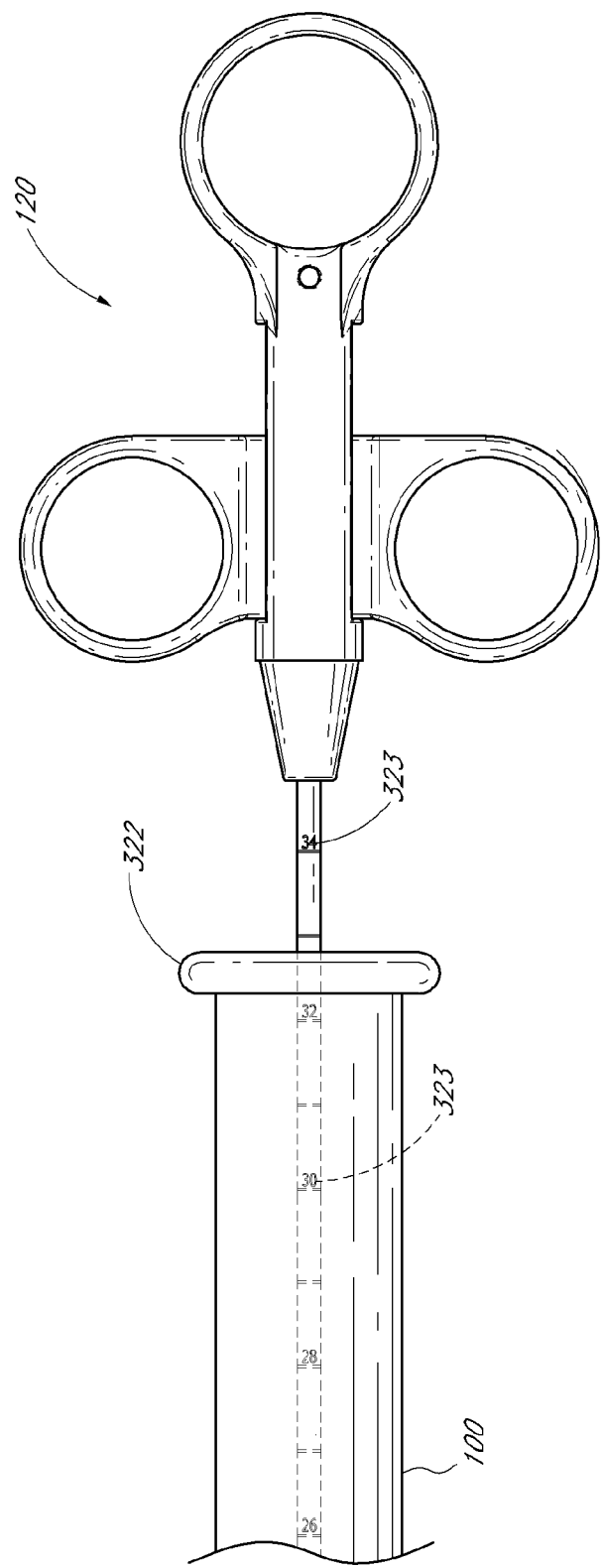
FIG. 22 illustrates an embodiment of an endotracheal tube cleaning device having a movable stop and visible depth markings.

FIG. 22 illustrates an embodiment of the endotracheal tube cleaning device 120 having a movable stop 322 and visible depth markings 323. In some embodiments, the visible depth markings 323 can be configured to align with corresponding depth measurements on the outside of the endotracheal tube 100. For example, if the endotracheal tube cleaning device 120 is being inserted into an endotracheal tube having a length of 26 cm, the endotracheal tube cleaning device 120 can be inserted until the 26 cm mark on the endotracheal tube cleaning device 120 is aligned with the 26 cm mark on the endotracheal tube. The visible depth markings 323 can be calculated such that when the corresponding depth marks are aligned, the distal tip of the endotracheal tube cleaning device 120 is at the desired depth within the endotracheal tube 100 (e.g., 1.5 cm proximal of the distal tip 108). Once the visible depth markings 323 are aligned with the corresponding markings on the endotracheal tube, the movable stop 322 can be locked in place at the proximal end 102 of the endotracheal tube 104, thereby providing a positive check on the insertion of the endotracheal tube cleaning device 120 within the endotracheal tube 100 and advantageously preventing against or reducing the likelihood of inadvertent over-insertion.

Figure 23A:
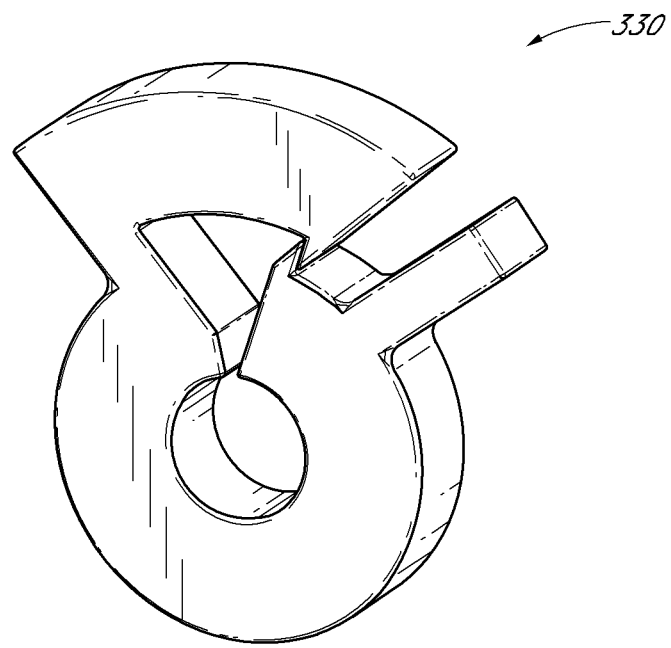
FIGS. 23A-23E illustrate various embodiments of a movable stop.

FIGS. 23A-23E illustrate various alternative embodiments of a movable stop 322 configured for use with an endotracheal tube cleaning device. FIG. 23A illustrates a locking clip design 330. In the unlocked configuration (shown in FIG. 23A), the locking clip can slide freely along the length of the outer shaft 129. When the locking clip is moved to the correct position, as determined by the visible depth markings 323, the locking clip can be squeezed or otherwise manipulated to actuate the living hinge feature and engage the locking feature. Accordingly, the locking clip can be maintained in a fixed position. The locking clip design 330 advantageously provides one-handed operation, a one-piece design, and a secure fastening feature. The materials for the locking clip design can comprise materials capable of providing "living hinge" capability, such as, for example, nylon, polypropylene, polycarbonate, and/or the like. In some embodiments the materials for the locking clip design 330 can comprise flexible materials, such as, for example, urethane, silicone, and/or the like.

Figure 23B:
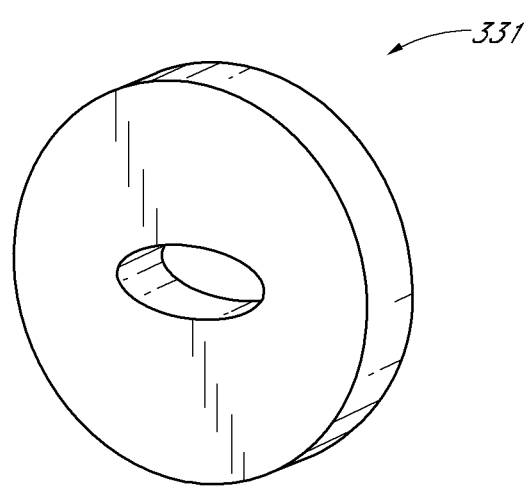

FIG. 23B illustrates an internal oval design 331. The internal oval design 331 provides a constant "lock" due to the interference of the internal oval opening with the radius of the outer shaft 129. In some embodiments, in order to temporarily "unlock" the movable stop and move the internal oval stop, manual force is used to overcome the friction fit connection of the internal oval design 331. The internal oval of the internal oval design 331 can become substantially circular as it is moved along the outer shaft 129. Once in position, the internal oval can return to a substantially oval shape. In some embodiments, the internal oval design 331 advantageously provides one-handed operation, a one-piece design, and a secure fastening feature. The materials for the internal oval design 331 can comprise materials having desired or required physical and other properties, such as, for example, toughness, flexibility, short term creep resistance, and/or the like. Such materials can include, for example, urethane, polyisoprene, TPE, other polymeric or elastomeric materials and/or the like.

Figure 23D:
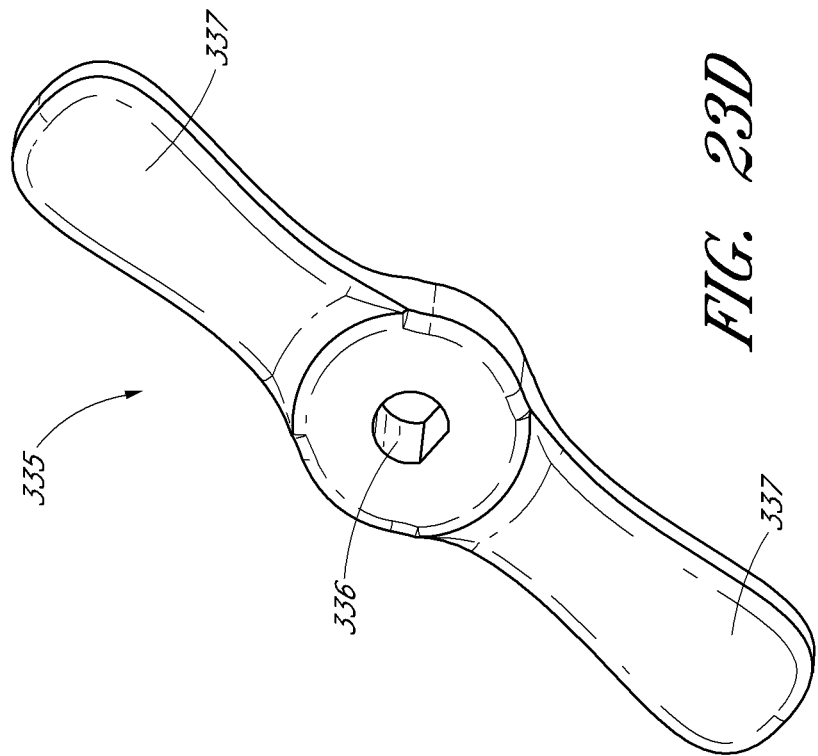
Figure 23C:
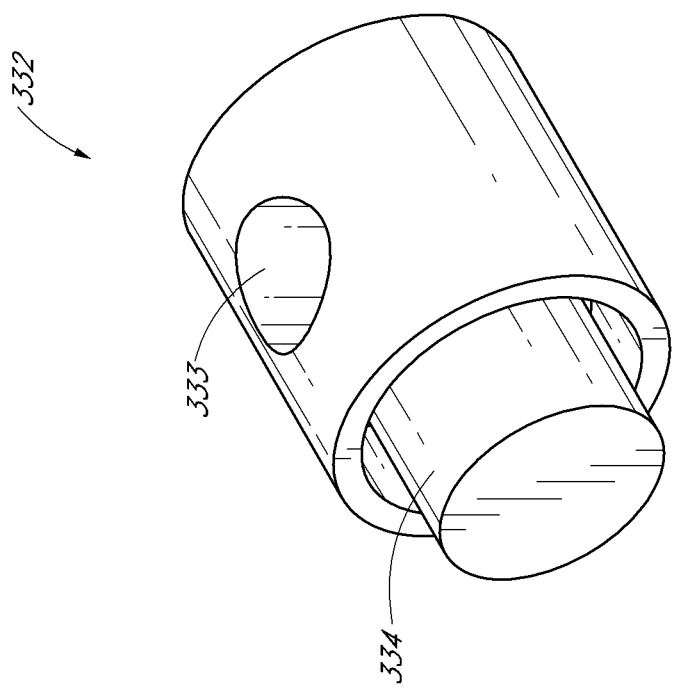

FIG. 23C illustrates one embodiment of a spring lock design 332 that is similar to the locking clips used on sweatshirt strings or drawstring bags. The bore or aperture 333 of the illustrated spring lock can have a diameter slightly larger than the diameter of the outer shaft 129. The spring lock is maintained in a locking position by a spring-loaded feature. According to some embodiments, in order to unlock the device to move to a new position, the spring-loaded feature is compressed by pressing on the compression element 334. When the spring lock is positioned in the desired position, the compression element 334 can be released, thereby releasing the spring-loaded feature to re-lock the spring lock. In other embodiments, the cylindrical features of the spring lock design 332 can be substituted with flat, rectangular features. In some embodiments, the spring lock design 332 advantageously provides one-handed operation. The spring lock design 332 can comprise one or more materials including, but not limited to, ABS, polypropylene, nylon, filled polypropylene, polycarbonate, polyethylene, other suitable injection-moldable grade resins, other polymeric or elastomeric materials, and/or the like.

FIG. 23D illustrates one embodiment of a double wing design 335. The double wing design 335 includes a D-shaped opening 336 and two symmetrical wings 337. In some embodiments, the flat-section of the D-shaped opening 336 is configured to match a corresponding flat section of the cross-section of the outer shaft 129. When the corresponding flat sections are aligned, the double wing stop can move freely along the outer shaft 129. In one embodiment, in order to set the maximum depth, the double wing stop is turned either clockwise or counterclockwise using the wings 337 so that the flat section of the D-shaped opening 336 interferes with the radius of the outer shaft 129. The double wing design 335 can advantageously provide one-handed operation and a one-piece design. The double wing design 332 can comprise one or more materials such as, for example, ABS, polypropylene, nylon, filled polypropylene, polycarbonate, polyethylene, other suitable injection-moldable grade resins, other polymeric or elastomeric materials, and/or the like.

Figure 23E:
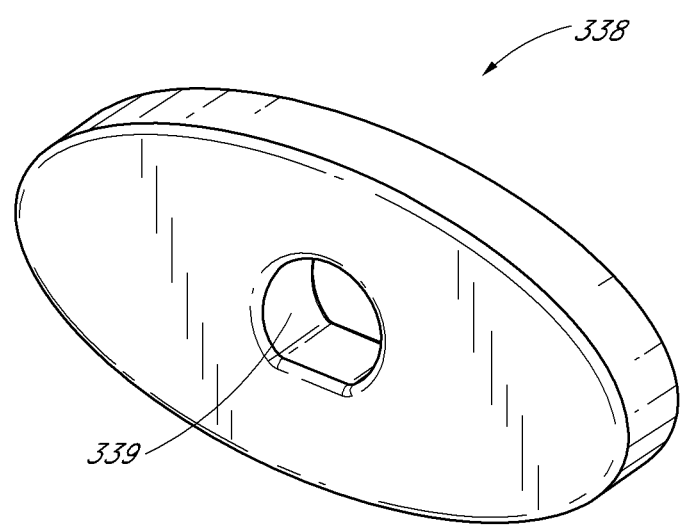

FIG. 23E illustrates one embodiment of an oval design 338. According to some embodiments, the oval design 338 includes a D-shaped opening 339 and operates in a similar manner to the double wing design 335. The oval design 338 can advantageously provide one-handed operation and a one-piece design. The oval design 338 can comprise one or more materials such as, for example, ABS, polypropylene, nylon, filled polypropylene, polycarbonate, polyethylene, other suitable injection-moldable grade resins, other polymeric or elastomeric materials, and/or the like.

In some embodiments, an elastomeric bag can be attached to the movable stop 322 for containment of the collected biofilm after removal from the endotracheal tube 100. The elastomeric bag can be attached in a furled or rolled-up configuration. The movable stop 322 with the attached elastomeric sheath can be moved along the outer shaft 129 in proximity to the biofilm that has been collected on the cleaning member 126. The elastomeric sheath can then be rolled out, or unfurled, over the cleaning member 126, thereby containing the collected biofilm until it has been safely deposited into a biohazardous container. The elastomeric bag can comprise one or more materials, such as silicone, latex, other elastomeric or polymeric materials, and/or the like.

B. Visualization

According to some embodiments, mechanical depth control can be enhanced, supplemented, or replaced with the help of one or more visualization features. As described above, an endotracheal tube cleaning device 120 can include a visualization channel or lumen configured to receive a visualization element (e.g., visualization scope 142). The visualization element can utilize ultrasound, infrared, CCD, fiberoptic and/ or any other type of imaging technology. For example, the visualization scope can comprise a fiber optic camera on the end of an endoscope. As discussed herein, the distal tip 130 of the endotracheal tube cleaning device 120 can include a transparent viewing "window" and/or other viewing area or region. The transparent viewing window or area of the visualization channel can advantageously enable a clinician to position the distal tip 130 of the endotracheal tube cleaning device at a selected location with respect to the endotracheal tube 100.

In some embodiments, the proximal end of the visualization channel is constructed with a introducer sheath area suitable for preventing or reducing the likelihood of contamination of the visualization element, thereby enabling reuse of the visualization element from one patient to another without concern for cross-contamination.

In some embodiments, the visualization element can facilitate, optimize, and/or document the endotracheal tube cleaning procedures. In some embodiments, the images received from the visualization element scope can be transferred to remote locations over a network, as described above, to permit remote observation. In some embodiments, an endotracheal tube cleaning system comprises a visualization scope (e.g., endoscope with a fiber optic camera), an external camera for viewing the nurse and the patient from a control room outside the ICU environment. The images from the visualization scope and external camera can be transmitted, along with clinical test and/or patient data, such as oxygen saturation, heart rate, respiration rate, and/or the like, to facilitate the remote treatment of the ICU patient.

VII. Supplementary and Preventative Modalities/Capabilities

In some embodiments, the endotracheal tube cleaning device 120 can have one or more channels or lumens for visualization, aspiration or suction, ventilation, irrigation/infusion, light delivery, and/or the like. In some embodiments, the endotracheal tube cleaning device 120 can have a single channel (e.g., a central lumen) for insertion of multiple catheters, probes, scopes, and/or other instruments. In other embodiments, the endotracheal tube cleaning device 120 includes two or more channels. For instance, an endotracheal tube cleaning device 120 can comprise a visualization channel, a suction channel, and an irrigation/infusion channel.

In arrangements including a side port 140, one or more channels or lumens of the endotracheal tube cleaning device 120 can be in communication with such a side port 140. In some embodiments, the channels or lumens of the cleaning device can be sheathed to prevent contamination of the catheters, probes, scopes, and/or other instruments inserted therein.

The additional catheters, probes, scopes, and/or instruments providing additional features to supplement and/or facilitate the cleaning of the endotracheal tube can be configured for single-handed operation. The single-handed operation can be facilitated with the use of fibers, cables, conduits, and/or lines of sufficient length such that the bulky components of the additional diagnostic, visualization, and/or therapeutic instruments or systems are positioned remote from the patient. In some embodiment, user controls for the additional instruments or systems are located adjacent to the patient or adjacent to the actuation assembly 124 of the endotracheal tube cleaning device 120 to enable the single-handed operation by the user. The various mechanisms can be controlled by pressing one or more user input controls with a single finger. In some embodiments, a different finger can be used for each respective action (e.g., one finger for aspiration and another finger on the same hand for irrigation or drug delivery). In other embodiments, the additional instruments and/or capabilities can be controlled by multiple hands and/or multiple persons.

In some embodiments, the additional instruments and capabilities can be controlled by the clinician concurrently with cleaning of the endotracheal tube with the endotracheal tube cleaning device 120. In other embodiments, the additional instruments and capabilities can be activated before, concurrently with, and/or after the cleaning with the endotracheal tube cleaning device 120. In some embodiments, two or more instruments can be activated simultaneously (for example, for broncho-alveolar lavage).

A. Suction/Aspiration

In some embodiments, a suction or aspiration catheter, conduit, or line can be inserted into a channel of the endotracheal tube cleaning device 120. The suction catheter can be used to perform an initial pre-cleaning suctioning of the tracheobronchial tree, the endotracheal tube 100 and/or any other item or region of the anatomy. The suction catheter can also be used to aspirate biofilm removed by the cleaning member 126 of the endotracheal tube cleaning device 120. The aspiration catheter can be used for sampling and analysis of the biofilm within the endotracheal tube of a patient to determine the bacterial content or nature of the biofilm. The clinician can then implement more effective treatment, antibiotics and safeguards against cross-contamination based at least in part on the determination of the bacterial content, thereby advantageously reducing infections, conditions, and/or other ailments, including but not limited to VAP, and reducing the length of stay of the ICU patient. In some embodiments, the endotracheal tube cleaning device 120 has a proximal seal at the entry of the tube for generally sealing the region during the application of suction, thereby helping to enhance the removal of material.

In some embodiments, the removal member 132 (e.g., O-ring) can include one or more openings or ports spaced continuously or intermittently around its circumference or other outer region to facilitate in the aspiration of biofilm and/or other materials. The suction catheter, conduit, or line can provide suction to the removal member 132 to facilitate removal of small amounts of biofilm that are not completely removed (e.g., wiped) from the inside surface of the endotracheal tube 100.

B. Irrigation/Fluid Delivery

In some embodiments, a delivery catheter can be inserted into a channel of the endotracheal tube cleaning device 120. Accordingly, the delivery catheter can be used to selectively deliver one or more fluids and/or other materials to a target region. In some embodiments, such fluids and/or other materials are adapted to disinfect, decontaminate, or sterilize the endotracheal tube. In some embodiments, such fluids and/or other materials are configured to loosen, break up, penetrate, degrade, disperse, dissolve and/or otherwise undermine or affect the biofilm 116 deposited on the inside surface of the endotracheal tube 100. In some embodiments, such fluids and/or other materials can aid in removal of the biofilm 116 and/or aid in the prevention of the future accumulation of biofilm. The delivery catheter can be configured and positioned to deliver one or more fluids and/or other materials to the inside wall of the endotracheal tube 100, tracheobronchial tree and/or any other region within a person's anatomy.

In some embodiments, fluids and/or other materials that are selectively delivered through a channel or lumen of the cleaning device include, without limitation: antibacterial agents, bactericides, antiviral agents, mucolytic agents, saline solution, sterilant, enzymatic cleaner, germicide, antimicrobial fluid, detergent, combinations of the same, and/or the like. In some embodiments, the antiviral agents can be configured to prevent or treat ventilator assisted pneumonia or other maladies or conditions.

In some embodiments, an irrigation channel or lumen can deliver drugs, fluids and/or other materials via the removal member 132 (e.g., O-ring), the collection member 134 (e.g., mesh scaffold), a deployment member (e.g., struts) and/or any other component or portion of the cleaning device. In some embodiments, the irrigation channel or lumen includes multiple outlets that are in communication with the outside of the endotracheal tube cleaning device 120 along the length of the channel. Accordingly, such embodiments can be used to selectively deliver fluids and/or other materials (e.g., antibiotics, antiviral substances, other pharmaceuticals, antiseptics, therapeutic agents, and/or the like) to the biofilm 116. In other embodiments, the irrigation channel or lumen includes a single outlet, either at the distal end of the endotracheal tube cleaning device 120 (e.g., in the distal tip 130) or at any other location along the length of the device, in order to selectively deliver the desired fluids, agents, and/or other materials to the biofilm 116. The one or more outlets can comprise a one-way valve, slit, and/or diaphragm to substantially seal the outlet, thereby preventing or reducing the likelihood of contamination due to an influx of bacteria or materials from inside the patient.

In some embodiments, an irrigation channel or lumen can be used to deliver drugs in a spray pattern that will deliver the drugs in an acceptable amount or rate to the wall of the endotracheal tube 100. In some embodiments, a drug delivery catheter can deliver a "mist" of a prescribed amount of a therapeutic agent, other pharmaceutical or drug and/or other substance to at least partially coat the inside wall of the endotracheal tube 100 and/or the biofilm attached thereto. In some embodiments, a drug delivery catheter can include a diffusing tip to enhance the spray of drugs to the wall of the endotracheal tube 100. For example, such tips or nozzles can help to more evenly diffuse the materials along a target region of the endotracheal tube or biofilm layer.

In other embodiments, an irrigation channel has a distal outlet directed at the "window," or distal tip, of the visualization channel to help clear debris and other materials away from the viewing window. Accordingly, the visualization features described herein can be improved.

C. Ventilation

In some embodiments, the endotracheal tube cleaning device 120 has an internal lumen that facilitates or enables the continued delivery of air, pure oxygen and/or other gases to the patient while the endotracheal tube cleaning device 120 is in place. This can help ensure that the patient's blood oxygen level is maintained above a threshold level during a particular procedure. However, in other embodiments, the cleaning device does not require supplemental oxygen or other gases to be delivered to a patient during a procedure. In some embodiments, the delivered gas or gases can be heated to a temperature of between about 120 degrees to about 180 degrees Fahrenheit.

D. Other Therapeutic Modalities

In some embodiments, one or more channels of the endotracheal tube cleaning device 120 can be used to deliver therapeutic modalities, such as sonication, vibration, radiation, photodynamic therapy, light, electrical stimulation and/or the like.

For example, photodynamic therapy can be used to treat specific bacteria identified as being present within the endotracheal tube 100 or within the tracheobronchial tree. In some embodiments, one or more drugs can be delivered through a channel (e.g., a drug delivery or infusion channel) of the endotracheal tube cleaning device 120 or by a separate drug delivery catheter to the inner wall of the endotracheal tube. Then, one or more light delivery elements (e.g., LEDs, lasers) can be inserted within the same channel or a different channel to deliver light at an appropriate wavelength (e.g., visible, infrared, UV wavelengths) to activate the one or more drugs delivered to the inner surface of the endotracheal tube. For example, UV-C light can reduce surface bacteria count within a matter of seconds. In certain embodiments, the drugs and light can be delivered concurrently. In embodiments where the light is delivered through the distal tip 130, the distal tip can be configured to disperse and/or diffuse the light (e.g., using a diffuser, a deflector, and/or the tissue optics properties of the tip itself) such that the appropriate wavelength, intensity, and/or quantity of light can be delivered to activate a specific drug. A control unit can be programmed and/or controlled to vary the wavelength, intensity, pulse width and duty cycle (if pulsed light is used), exposure time, and/or the like of the light.

As another example, sound waves can be delivered through using a sonication device. Such sound waves can advantageously have an inhibiting effect on the sustainability and/or growth of biofilm. Vibrations produced by the sonication device can loosen the tenacious or more adherent biofilm. In some embodiments, one or more sensors or electrodes can be introduced on a probe or catheter to detect one or more physiological conditions or parameters of the patient.

VIII. Introduction Connector

In some embodiments, an endotracheal tube cleaning system includes an adapter or introduction connector that advantageously enables the patient to remain connected to a mechanical ventilator, thereby maintaining ventilator airflow, during cleaning of the endotracheal tube.

Figure 24A:
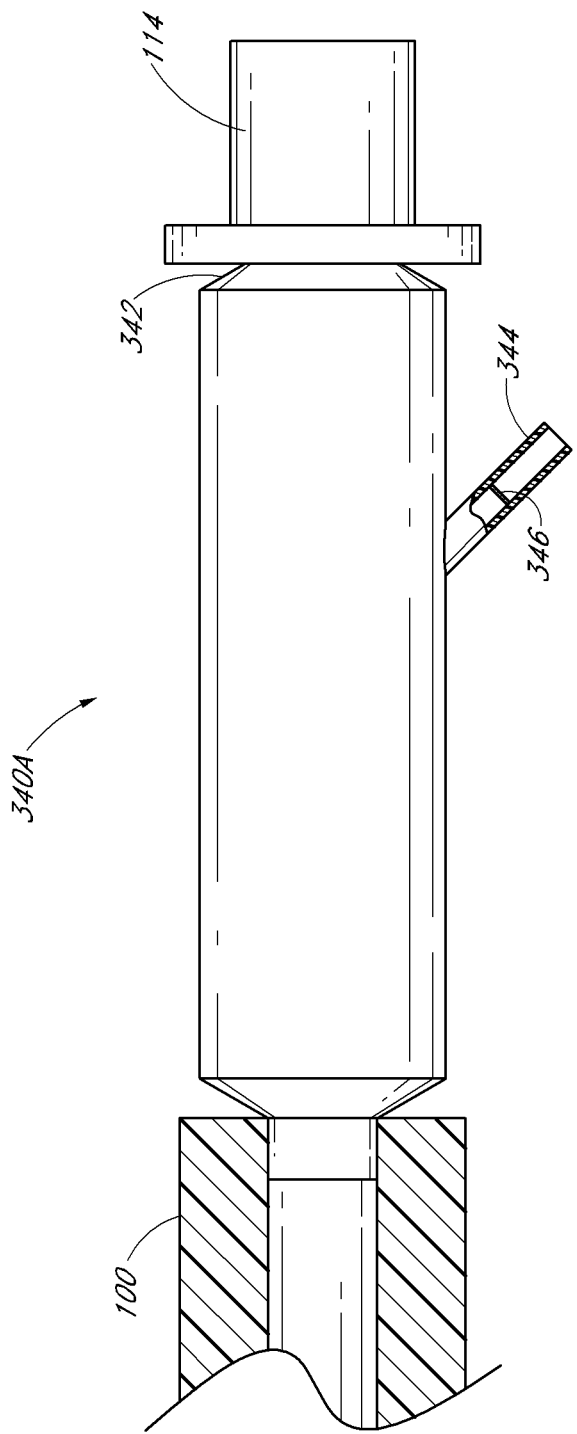
FIGS. 24A and 24B illustrate two embodiments of an introduction adapter.
Figure 24B:
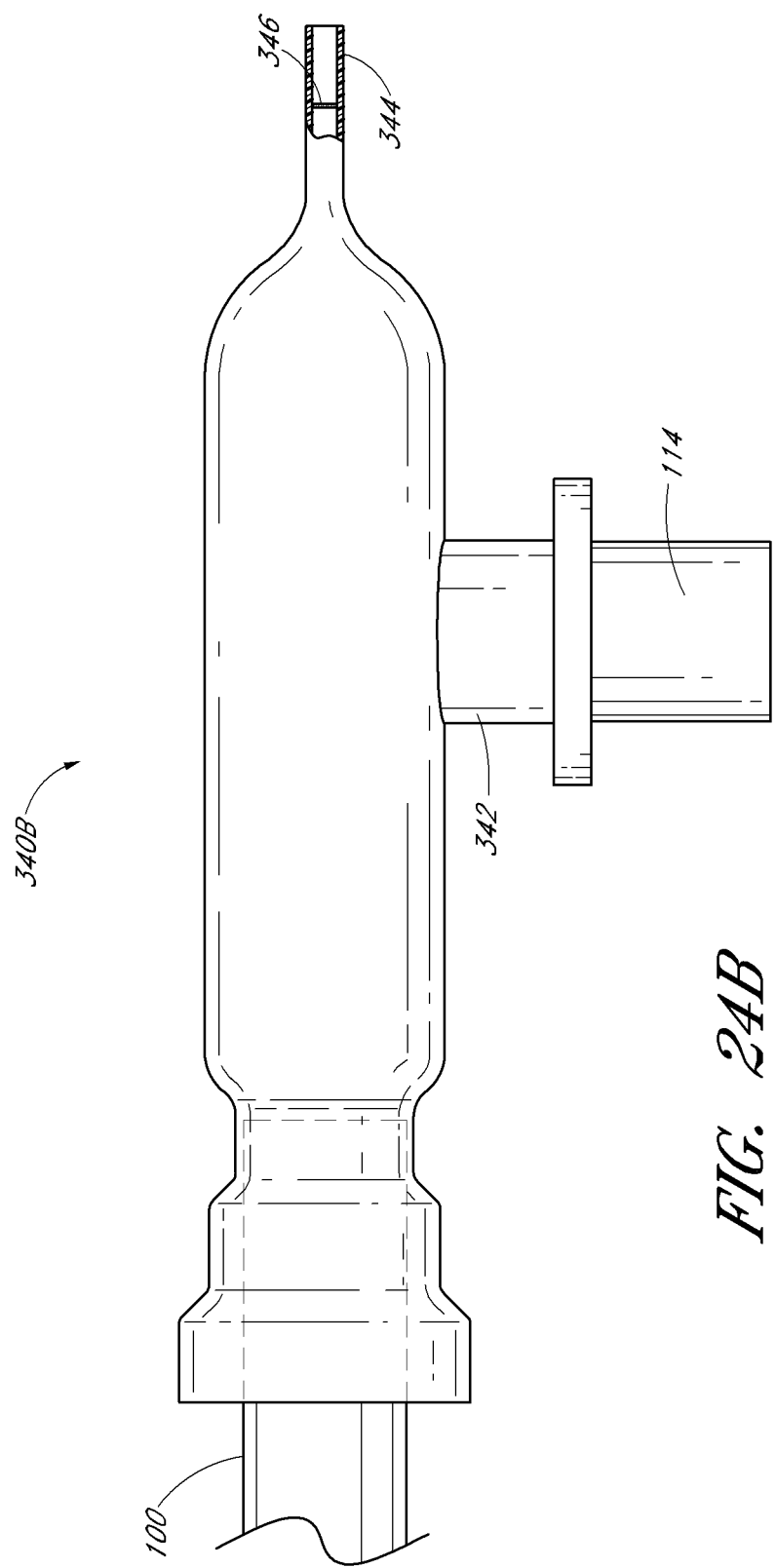

FIGS. 24A and 24B illustrate two embodiments of adapter configurations to facilitate introduction of a tube cleaning device 120 in an endotracheal tube during a procedure. In some embodiments, the distal end of the adapter 340 is configured to removably couple (e.g., directly or indirectly) to the proximal end 102 of the endotracheal tube 100 after removal of the ventilator coupling element 114. In some embodiments, the distal end of the adapter 340 is sized and configured to be inserted within the lumen 106 of the endotracheal tube 100 (as shown in FIG. 24A). In other embodiments, the distal end of the adapter 340 is sized and configured to fit around the outside surface of the endotracheal tube 100 (as shown in FIG. 24B), thereby reducing the likelihood of the cleaning member of the endotracheal tube cleaning device 120 being snagged on a ridge introduced by the thickness of the inserted adapter 340 during removal from the endotracheal tube 100.

In some embodiments, the adapter 340 includes a ventilation port 342 and a device insertion port 344. The ventilator coupling element 114 can be coupled to the ventilation port 342 for connection to the ventilator. The device insertion port 344 can be used to insert the endotracheal tube cleaning device 120 and/or other devices (e.g., catheters, probes, scopes). In one embodiment, the device insertion port 344 includes an elastomeric diaphragm 346 to help prevent loss of ventilator tidal volume. The elastomeric diaphragm 346 can comprise a slit, a one-way valve and/or any other device or feature to substantially seal around the inserted device. This can advantageously help prevent the escape of ventilator tidal volume. The elastomeric diaphragm 346 can comprise one or more elastomeric materials, such as, for example, urethane, latex, silicone, other polymeric or elastomeric materials, and/or the like. The thickness of the diaphragm 346 can range from about 0.002 inches to about 0.030 inches. In some embodiments, the thickness of the diaphragm 346 is about 0.005 inches to about 0.20 inches. However, in other embodiments, the diaphragm thickness is greater than 0.030 inches or smaller than 0.002 inches, as desired or required.

The device insertion port 344 can be sufficiently long such that the entire distal end of the endotracheal tube cleaning device 120 is located proximal to the distal end of the adapter 340 when the adapter 340 is removed. For example, the length of the device insertion port 344 can range from about 30 cm to about 60 cm. The diameter of the device insertion port 344 can range from about 4 mm to about 7 mm. The inner diameter of the ventilation port can be sized to be slightly larger than the outer diameter of the ventilator coupling element 114. The length of the adapter 340 can range from about 4 cm to about 10 cm. Other dimensions for the adapter 340 can be used as desired and/or required.

As shown in FIG. 24A, the adapter 340A can be Y-shaped, with the ventilation port 342 located at the proximal end of the adapter and the device insertion port 344 extending from the side of the adapter at an acute angle. The embodiment of the adapter 340B illustrated in FIG. 24B is generally T-shaped, with the device insertion port 344 located at the proximal end of the adapter 340B and the ventilation port 342 extending from the side of the adapter 340B at a right angle. In other embodiments, the adapter 340B can be Y-shaped, with the ventilation port 342 extending from the side of the adapter 340B at an acute angle. The adapter 340B of FIG. 24B advantageously provides a straight insertion path for the endotracheal tube cleaning device 120 or other devices. In other embodiments, the adapters 340 can have a different shape or configuration than discussed and illustrated herein.

The adapters 240 can include distance markings from the connection to the proximal end of the endotracheal tube to the opening of the device insertion port 344 to aid in positioning the endotracheal tube cleaning device 120 and the locking of the movable stop 322. In some embodiments, the distance from the endotracheal tube connection to the opening of the device insertion port can range from about 4 cm to about 8 cm; however, other lengths can be used as desired and/or required.

According to some embodiments, kits of adapters 340 can be provided to accommodate endotracheal tubes having various diameters. The adapters 340 can include markings indicating the tube diameter(s) for which they can be used. In other embodiments, the adapters 340 comprise one-size-fits-all (or one-size-fits-most) adapters that can be used to fit endotracheal tubes of various diameters. For example, the adapter 340B of FIG. 24B has three varying cross-sectional diameters so as to enable the adapter 340B to fit endotracheal tubes of three different outer diameters (e.g., 7 mm, 8 mm, or 9 mm).

In some embodiments, adapters 340 can also be used to at least partially contain biofilm that has been removed by the cleaning member 126. For example, when an adapter 340 is disconnected from the endotracheal tube 100 and ventilator, the distal end of the adapter can be slid over the cleaning member 126, thereby providing a protective covering over the removed biofilm to prevent contamination.

IX. Use

A. General Use

As generally described herein, the endotracheal tube cleaning devices and systems described herein can be used to clean endotracheal tubes while a patient is being supported by a ventilator connected to the endotracheal tube. This cleaning is useful for increasing the available space for airflow in the endotracheal tube and for reducing or preventing the build up of materials that would otherwise constrict airflow through the endotracheal tube and potentially be a nidus for infection.

Figure 25:
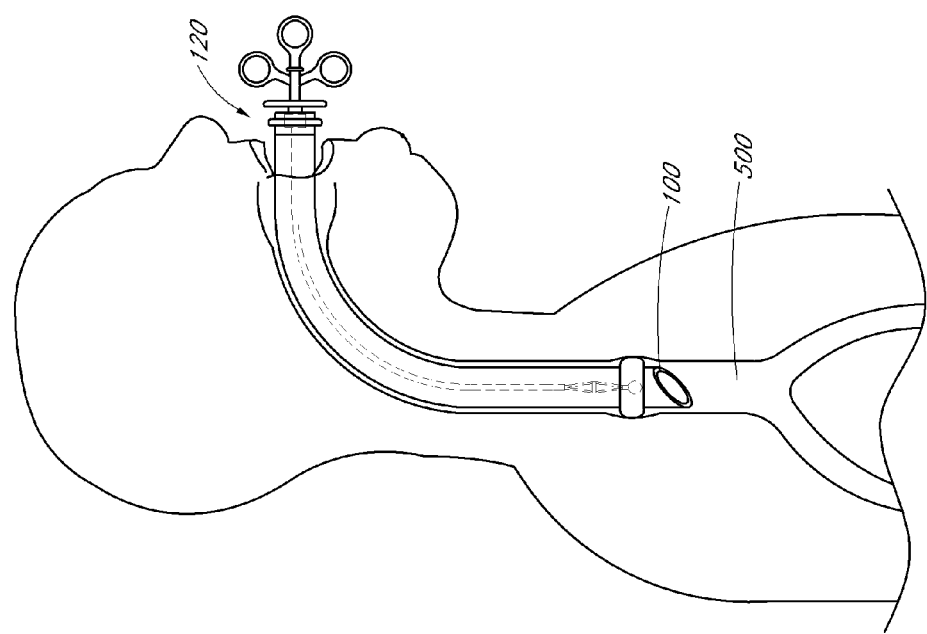
FIG. 25 illustrates an endotracheal tube cleaning device inserted within an endotracheal tube positioned within a native airway of a human patient.

FIG. 25 illustrates an embodiment of the endotracheal tube cleaning device 120 inserted within an endotracheal tube 100 within a native airway 500 of a patient. The endotracheal tube cleaning device 120 can advantageously be used to clean the endotracheal tube 100 while the endotracheal tube 100 remains inside the patient.

B. Indications

According to some embodiments, an endotracheal tube cleaning device 120 can be used for a variety of indications. For example, the endotracheal tube cleaning device 120 can be used for preventative indications, for daily use indications, and/or for near total occlusion indications. In some embodiments, the endotracheal tube cleaning device 120 can be used at least once a day to prevent any extensive buildup of biofilm, as biofilm has been shown to start building up as early as within 24 hours of intubation. Daily utilization can coincide with ICU protocols for daily extubation attempts for all patients. In other embodiments, the frequency of endotracheal tube cleaning can vary, depending on patient, the patient's health and other conditions, a desired cleaning protocol and/or the like.

For example, in some embodiments, the endotracheal tube cleaning device 120 can be used multiple times a day for high risk patients. High risk patients can include older patients, smokers, patients with chronic obstructive pulmonary disease (COPD), patients intubated as part of their treatment for respiratory insufficiency related to pneumonia, patients with an indwelling endotracheal tube for longer than 24 to 48 hours and/or others. The frequency of use can be determined by clinical evaluation and observation of the degree of secretions being produced by an individual patient. However, the frequency of cleaning can depend on one or more other features, as desired or required.

The endotracheal tube cleaning device 120 can advantageously be used on intubated patients with ongoing bloody secretions or frank hemoptysis in order to prevent clots from obstructing the endotracheal tube lumen. The endotracheal tube cleaning device 120 can also be used on patients who fail weaning and extubation trials before tracheostomy is performed. The endotracheal tube cleaning device 120 can advantageously be used on intubated patients who experience an acute unexplained change in their respiratory or ventilatory status in order to rule out mucous plugging or clotting within the endotracheal tube as a cause of the sudden deterioration.

The amount of biofilm to be removed in the various indications can vary greatly. By way of example, for a prevention indication, the endotracheal tube cleaning device 120 can collect about 1 cc to about 5 ccs of biofilm. By contrast, in daily use indications, the endotracheal tube cleaning device can collect about 5 ccs to about 15 ccs of biofilm. Further, for near total occlusion indications, the endotracheal tube cleaning device can collect more than about 15 ccs of biofilm.

In one embodiment, the cleaning member can be radially expanded or otherwise radially deployed in a manner that sufficient contacting force is maintained between a contact surface of the cleaning member and the internal wall of the endotracheal tube and/or the biofilm accumulated thereon. This can advantageously permit the cleaning member to shear, wipe, or otherwise remove the biofilm, while preventing or reducing the risk of hydroplaning, cavitation, and/or invagination.

In several embodiments, the pull-out force used to withdraw the endotracheal tube cleaning devices can be provided by a clinician using a single hand without significant strain. In one embodiment, the cleaning device comprises a mesh scaffold coupled to a silicone O-ring having a softness of 40 Shore A durometer with a pull-out force that is comparable to the mesh scaffold alone. In one embodiment, the removal members do not appreciably increase the pull-out force used to withdraw the endotracheal tube cleaning devices when such devices are being used to remove biofilm deposited on the internal wall of an endotracheal tube in a single pass.

C. Cleaning Processes

Figure 26:
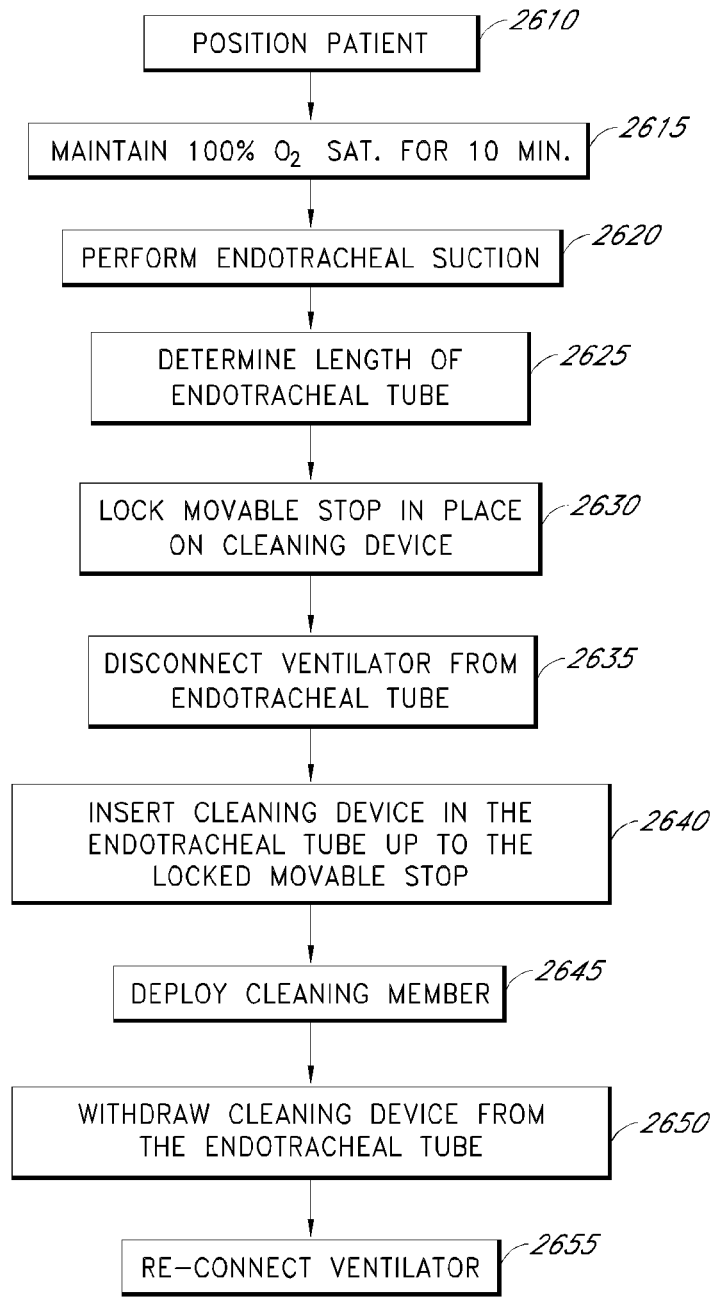
FIG. 26 is a flow chart illustrating an embodiment of a process for cleaning an inside surface of an endotracheal tube while a patient is supported by function of the endotracheal tube.

FIG. 26 is a flow chart illustrating an embodiment of a process 2600 for cleaning an inside surface of an endotracheal tube (e.g., endotracheal tube 100) while such an endotracheal tube 100 is inserted within a patient. The cleaning process 2600 starts at block 2610, where the head of the bed is positioned at approximately 30° relative to horizontal. In other embodiments, the head of the bed can be positioned at angles larger or smaller than 30° relative to horizontal as desired and/or required. According to some embodiments, information related to the patient's heart rate, heart rhythm, blood pressure, $O_2$ saturation, other vital signs and/or other desired data can be detected and advantageously displayed to the clinician performing the cleaning procedure. In some embodiments, oxygen at 100% $FiO_2$ or nearly 100% $FiO_2$ is delivered to the patient for ten minutes or another desired time period via a ventilator attached to the patient's endotracheal tube 100, as illustrated at block 2615. A disposable chux, pad and/or support member can be placed under the endotracheal tube 100 and ventilation connection, and may be spread out over the patient's chest.

Next, in some embodiments, routine endotracheal suction is performed, and the endotracheal tube 100 is checked to confirm that it is properly secured to the patient's face and/or mouth, as illustrated at block 2620. The exact length from the visible proximal end of the endotracheal tube 100 to its tip within the patient can then be determined from visible markings on the endotracheal tube 100, as illustrated at block 2625. According to some embodiments, the endotracheal tube cleaning device 120 is visualized and the movable locking stop 322 that prohibits over-insertion of the endotracheal tube cleaning device 120 is locked to an axial position that deploys the cleaning member 126 no closer than 1.5 cm from the distal tip of the endotracheal tube 100, as illustrated at block 2630. In other embodiments, the movable stop on the endotracheal tube cleaning device 120 is set to the position corresponding to the length of the endotracheal tube.

In some embodiments, the ventilator is temporarily disconnected from the endotracheal tube 100 at block 2635 and the endotracheal tube cleaning device 120 is inserted into the endotracheal tube up to the locking stop 322 at block 2640. In some embodiments, disconnecting the ventilator at block 2635 includes loosening the ventilator coupling element 114 for one hand removal and then removing the ventilator coupling element with one hand while standing at the patient's side at chest level after the ventilator is disconnected. The endotracheal tube cleaning device 120 can be inserted at block 2640 in a single-hand operation using the other hand (the hand not used to remove the ventilator coupling element 114).

The cleaning member 126 can then be deployed at block 2645 (e.g., with a one-hand activation of the actuation assembly 124) and the endotracheal tube cleaning device 120 can then be withdrawn from the endotracheal tube 100 while applying counter-traction to the endotracheal tube 100 itself at block 2650. The endotracheal tube cleaning device 120 can be withdrawn over a one to three second time period. In other embodiments, withdrawal of the cleaning device can be faster than one second or longer than three second, as desired, required or permitted for a particular application or use. The removed endotracheal tube cleaning device 120 can be placed on a chux and wrapped up for biohazard disposal or reinserted into the original peel pouch and placed in a biohazard collection unit. In one embodiment, the patient is then reconnected to the ventilator at block 2655 after reconnecting the ventilator coupling element 114

The steps of the endotracheal tube cleaning process 2600 described above can be repeated multiple times as necessary at a single treatment with the endotracheal tube cleaning device 120, so long as the patient's heart rate, heart rhythm, blood pressure, and $O_2$ saturation remain stable. The endotracheal tube cleaning process 2600 can be performed by a single person or by multiple persons. For example, a first person (e.g., nurse or respiratory therapist) can perform the cleaning with the endotracheal tube cleaning device and a second person (e.g., an ICU technician) can disconnect and reconnect the ventilator, remove the endotracheal tube cleaning device from its packaging, and dispose of the used endotracheal tube cleaning device.

Figure 27:
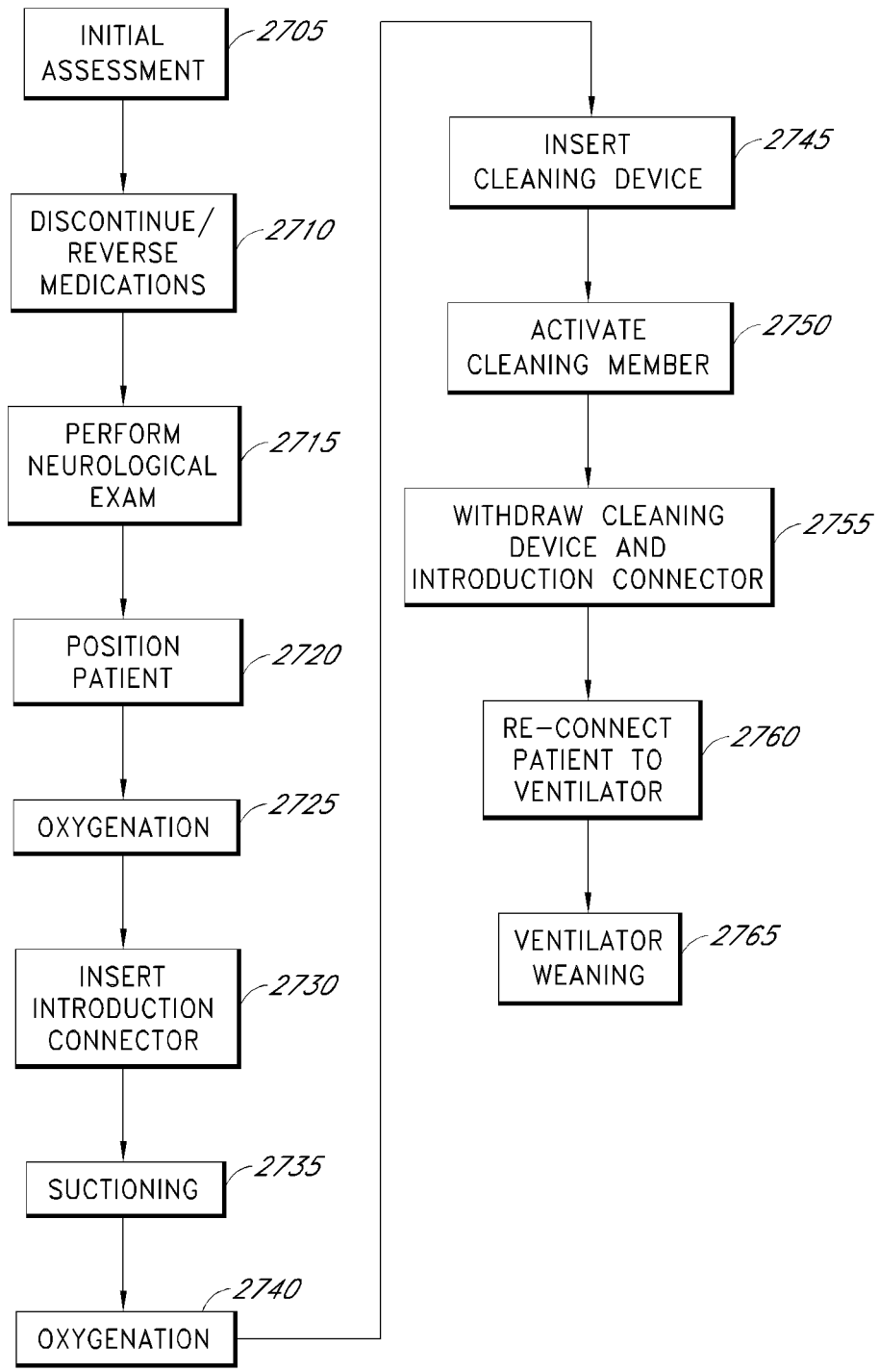
FIG. 27 illustrates an embodiment of a daily extubation process in which an endotracheal tube cleaning device can be utilized.

In some embodiments, endotracheal tube cleaning methods can be performed during a daily extubation attempt. FIG. 27 illustrates one embodiment of a daily extubation process 2700 in which the endotracheal tube cleaning device 120 can be utilized.

With reference to the embodiment of a daily extubation process 2700 illustrated by the flowchart in FIG. 27, the clinician performs an initial assessment 2705 to ensure that the patient is in a stable condition. The clinician can ensure that no hemodynamic or respiration system acute clinical changes exist that would make that system a priority. Next, the clinician discontinues or reverses sedating medications 2710 that may interfere with spontaneous ventilation and/or medications that may produce a paralytic effect.

With continued reference to the procedure illustrated in FIG. 27, at block 2715, the clinician performs a neurological examination to be sure that the patient is alert and able to follow commands. As indicated at block 2720, the patient can be positioned semi-upright (e.g., the head of the bed is elevated to at least approximately 30 degrees relative to horizontal). In some embodiments, the patient is then oxygenated at 100% $FiO_2$ or nearly 100% $FiO_2$ for approximately ten minutes at block 2725 (pre-cleaning ventilation). In other embodiments, the patient is oxygenated for more or less than ten minutes as desired and/or required.

In some embodiments, as illustrated at block 2730, the ventilator coupling element 114 is removed and an introduction connector (e.g., adapter 340) is placed between the endotracheal tube 100 and the ventilator. At block 2735, endotracheal suctioning can be performed to aspirate pooled secretions from the major segments of the tracheobronchial tree. According to some embodiments, the patient is then oxygenated again at 100% $FiO_2$ or nearly 100% $FiO_2$ for ten minutes, as illustrated at block 2740. In other embodiments, the patient is oxygenated for more or less than ten minutes as desired and/or required.

According to some embodiments, as illustrated at block 2745, the clinician can insert the endotracheal tube cleaning device 120 through the introduction connector after setting a maximum insertion depth with the movable stop 322 based on the length of the endotracheal tube to be cleaned. With reference to block 2750 of the flowchart of FIG. 27, the cleaning member 127 can be expanded by activating the actuation assembly 124 to the appropriate setting corresponding to the predetermined inner diameter of the endotracheal tube.

At block 2755 of FIG. 27, the endotracheal tube cleaning device 120, including the introduction connector which may be used to contain the biofilm, can be withdrawn from the endotracheal tube. Then, the patient can be reconnected to the ventilator at block 2760 after reconnecting the ventilator coupling element 114. At block 2765, ventilator weaning can be performed for approximately ten minutes. In some embodiments, the ventilator weaning period advantageously allows time for improved ventilation/perfusion match to occur following removal of the endotracheal tube cleaning device 120.

In some embodiments, any or all of the steps in the daily extubation process 2700 can be repeated. In other embodiments, one or more steps can be removed, modified, or altered without departing from the spirit and/or scope of the disclosure. The daily extubation process 2700 can be performed by a single person and/or multiple persons.

Figure 28:
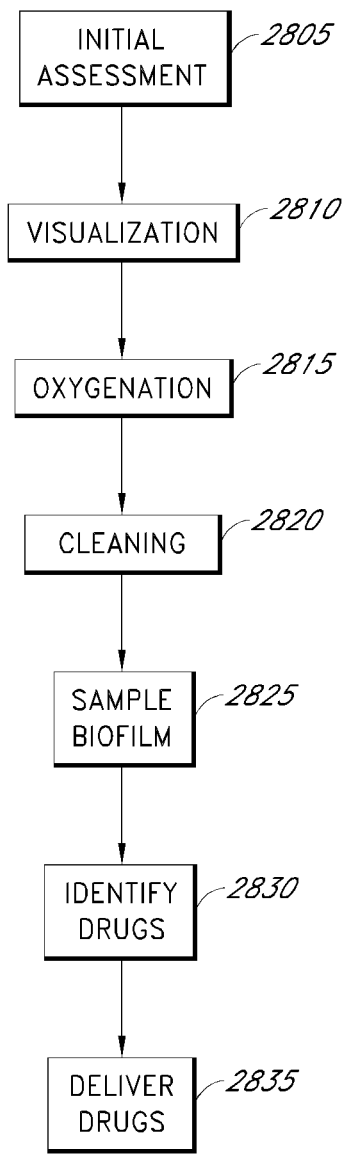
FIG. 28 illustrates an embodiment of a process for preventing buildup of biofilm within an endotracheal tube.

FIG. 28 illustrates an embodiment of a process 2800 for preventing the buildup of biofilm inside an endotracheal tube. The process 2800 begins at block 2805, where an initial assessment of a patient's risk factors for biofilm buildup and VAP is performed. Also at block 2805, an intervention plan can be created based at least in part on clinical parameters, such as oxygen saturation levels. At block 2810, the patient's airway and/or endotracheal tube is viewed using a visualization or imaging element.

In some embodiments, the patient is then prepared for endotracheal tube cleaning by oxygenating the patient at block 2815. For example, the patient can be oxygenated for approximately ten minutes or other desired time period at a 100% or nearly 100% oxygen saturation level. At block 2820, an endotracheal tube cleaning can be performed by inserting an endotracheal tube cleaning device (e.g., endotracheal tube cleaning device 120) into the endotracheal tube and then removing it. At block 2825, biofilm removed by the endotracheal tube cleaning device can be optionally sampled. With reference to block 2830 of the flowchart of FIG. 28, the clinician identifies the drugs that are most appropriate for preventing biofilm buildup and/or treating the bacteria present in the biofilm sample.

According to some embodiments, at block 2835, the identified drugs are delivered to the endotracheal tube and/or to the native airway of the patient. In some embodiments, the drugs are delivered through an internal lumen of the endotracheal tube cleaning device 120. In other embodiments, the drugs are delivered using a drug delivery catheter without the use of the endotracheal tube cleaning device 120. The delivery of the identified drugs can be repeated according to a predetermined delivery schedule as desired and/or required.

D. Artificial Biofilm for Training

In some embodiments, an artificial biofilm can be constructed to simulate the build up and distribution of biofilm for the purposes of training ICU personnel "best practices" for identifying, removing, sampling, culturing, suctioning or lavaging of actual biofilm. The artificial biofilm can comprise one or more of the following: slime, gelatin, glycerin, petroleum, egg whites, hair spray or hair gel, and like materials, and combinations thereof. In one embodiment, the artificial biofilm comprises a gelatinous material with a texture and density that mimics natural mucous. The artificial biofilm can be inserted into a standard endotracheal tube positioned within a model of a human airway. The artificial biofilm can be inserted using a syringe and catheter, for example.

In some embodiments, the artificial biofilm can be inserted so as to simulate typical patient conditions after prolonged ventilation (e.g., greater than 24 hours). For example, little to no artificial biofilm can be inserted in the first 2.5 cm from the distal tip of the endotracheal tube, a 0.1 mm thick layer of artificial biofilm can be inserted along the inner surface of the main collection region of the endotracheal tube, and a 0.5 mm thick layer of artificial biofilm can be inserted along the inner surface of the endotracheal tube from the main collection region to the proximal end of the endotracheal tube.

The training of the ICU personnel using the artificial biofilm can be performed with or without a visualization element. If the training is performed without the visualization element, the endotracheal tube cleaning device can be inserted, deployed, and removed as described above. If the training is performed with the visualization element, the images provided by the visualization element can be displayed for viewing by multiple ICU personnel and/or can be recorded for subsequent training.

The use of the artificial biofilm can aid in demonstrating the effect of an occluded endotracheal tube on oxygen saturation levels. The artificial biofilm can also be used to train ICU personnel on the visualization, sampling, suction, and/or cleaning features of the endotracheal tube cleaning devices, systems and methods described herein. The use of the artificial biofilm to train ICU personnel advantageously allows for simulated role play without compromising patient safety.

X. Other Uses

Although the endotracheal tube cleaning devices, methods, and systems described herein have been described in connection with the cleaning of endotracheal tubes or other body-inserted tubes, the embodiments and features described herein can be used for other medical applications, such as, for example, the cleaning of catheters, probes, body lumens, vasculature (e.g., arteries and veins), urinary tracts, grafts (e.g., hemodialysis grafts, vascular grafts), aspiration conduits, ventilation tubes, and the like. Non-medical applications of the devices, methods, and systems described herein include, but are not limited to, the cleaning of pipes, hoses, guns, ventilation ducts and any other hollow or substantially hollow structure and/or the like.

XI. Functionality

In one embodiment, the endotracheal tube cleaning device 120 is a fully disposable, single-use device. In other embodiments, one or more components or portions of the endotracheal tube cleaning device 120 are selectively detachable and configured for reuse. For example, the elongate body 122 and the actuation member 124 can be reusable, while the cleaning member 126 can be detachable and disposable. In some embodiments, the spent endotracheal tube cleaning device 120 is deposited in a biohazardous container after removal. In some embodiments, the endotracheal tube cleaning device 120 can perform multiple cleaning passes for a single patient before being disposed.

According to some embodiments, the endotracheal tube cleaning device 120 is configured for single-handed operation by a single practitioner. In alternative embodiments, the endotracheal tube cleaning device 120 can be operated using two hands or by multiple practitioners.

In some embodiments, the endotracheal tube cleaning device 120 is configured to be single-pass device that clears or removes up to 90% of more of the biofilm. In other embodiments, a single pass device can be designed and otherwise configured to remove more or less than 90% of biofilm, as desired and/or required.

In other embodiments, such as when the endotracheal tube has been in the patient for multiple days without being cleaned and/or more than about 15 ccs of biofilm has accumulated within the endotracheal tube, multiple passes may be performed to remove the biofilm. The determination as to whether to perform additional cleaning passes can be made using visualization devices inserted within the endotracheal tube, as described herein, or by visual inspection of the cleaning member 126 upon removal of the endotracheal tube cleaning device 120. For example, if the capacity of the collection mechanism of the endotracheal tube cleaning device 120 visually appears to have been reached and/or exceeded, another pass may be desirable.

According to some embodiments, the endotracheal tube cleaning device 120 is provided in a pouch or tray and is sterile ready to use. In other embodiments, the endotracheal tube cleaning device 120 can be provided sterilized or clean ready to use. In one embodiment, the endotracheal tube cleaning device 120 is provided in a disposable peel-pack or pouch. At least one sleeve of the peel-pack can be used for disposal of the spent endotracheal tube cleaning device 120 and the removed biofilm.

In some embodiments, the insertion and removal of the endotracheal tube cleaning device 120 can be completed in less than about ten seconds, with 90% of the biofilm being removed. However, as discussed herein, the time period for completing a procedure and/or the exact amount of biofilm removed from a cleaning procedure can vary, as desired or required. For example, in one embodiment, the insertion of the endotracheal tube cleaning device 120 can be performed in less than two seconds and the removal of the endotracheal tube cleaning device 120 can be performed in one to three seconds.

In some embodiments, the endotracheal tube cleaning device 120 can be twisted or rotated manually by a clinician to enhance the wiping action of the removal member 132 (e.g., O-ring). In other embodiments, the removal member 132 (e.g., O-ring) and/or the collection member 134 (e.g., mesh scaffold) have one or more driving mechanisms to effectuate a tangential wiping motion in addition to the pulling wiping motion of the cleaning member 126. Still other embodiments include a screw mechanism so that the cleaning member 126 twists as the endotracheal tube cleaning device 120 is withdrawn.

Conditional language, for example, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Although certain embodiments and examples have been described herein, it will be understood by those skilled in the art that many aspects of the methods and devices shown and described in the present disclosure may be differently combined and/or modified to form still further embodiments. Additionally, it will be recognized that the methods described herein may be practiced using any device suitable for performing the recited steps. Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Additionally, the skilled artisan will recognize that any of the above-described methods can be carried out using any appropriate apparatus. Further, the disclosure herein of any particular feature, aspect, method, property, characteristic, quality, attribute, element, or the like in connection with various embodiments can be used in all other embodiments set forth herein. Additionally, process steps may be added, removed, or reordered. A wide variety of designs and approaches are possible.

For purposes of this disclosure, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

What is claimed is:

1. A mechanically-actuated cleaning device for removing biofilm or debris from a body-inserted medical tube, comprising:
    an elongate body comprising a distal end, a proximal end and an inner lumen extending from the proximal end to the distal end,
    a cleaning member positioned at or near the distal end of the elongate body, wherein the cleaning member is mechanically actuated,
    wherein the cleaning member is selectively movable between a radially-collapsed configuration and a radially-expanded configuration,
    wherein at least a portion of the cleaning member is configured to circumferentially contact an interior surface of a medical tube when in the radially-expanded configuration,
    wherein the cleaning member, when in the radially-expanded configuration, is configured to remove biofilm or debris from the medical tube as the elongate body is withdrawn from the medical tube,
    wherein the cleaning member, when in the radially-expanded configuration, comprises a rounded profile,
    wherein the portion of the cleaning member that is configured to circumferentially contact the interior surface of the medical tube comprises a generally smooth contact surface; and
    a mechanically-actuated control assembly coupled to the proximal end of the elongate body,
    wherein the cleaning member is selectively movable between the radially-collapsed configuration and the radially-expanded configuration by mechanical manipulation of the control assembly.

2. The cleaning device of claim 1, wherein the cleaning member comprises a mesh expandable member.

3. The cleaning device of claim 1, wherein the cleaning member comprises struts configured to selectively move the cleaning member between the radially-collapsed configuration and the radially-expanded configuration.

4. The cleaning device of claim 1, wherein the elongate body comprises an inner shaft and an outer shaft coupled to the control assembly, wherein a distal end of the inner shaft is coupled to a distal end of the cleaning member and a distal end of the outer shaft is coupled to a proximal end of the cleaning member, and wherein movement of the inner shaft relative to the outer shaft moves the cleaning member between the radially-collapsed configuration and the radially-expanded configuration.

5. The cleaning device of claim 4, wherein the control assembly comprises a handle and a trigger, wherein the trigger is coupled to the inner shaft and wherein the handle is coupled to the outer shaft.

6. The cleaning device of claim 1, wherein the cleaning member comprises one or more wiper members.

7. The cleaning device of claim 1, wherein the elongate member comprises a distal tip, and wherein the distal tip comprises a viewing window.

8. The cleaning device of claim 7, wherein the inner lumen is configured to receive a visualization scope to provide visualization through the viewing window.

9. A mechanically-actuated cleaning device for removing biofilm or debris from a body-inserted medical tube, comprising:
- an elongate body comprising a distal end and a proximal end,
- a cleaning member positioned at or near the distal end of the elongate body,
- wherein the cleaning member is selectively movable between a collapsed configuration and an expanded configuration,
- wherein at least a portion of the cleaning member is configured to contact an interior surface of a medical tube when the cleaning member is in the expanded configuration,
- wherein the cleaning member, when in the expanded configuration, is configured to remove biofilm or debris from the interior surface of the medical tube as the elongate body is withdrawn from the medical tube,
- wherein the cleaning member, when in the expanded configuration, comprises a rounded profile,
- wherein the portion of the cleaning member that is configured to contact the interior surface of the medical tube is non-porous; and
- a mechanically-actuated actuation assembly coupled to the proximal end of the elongate body, wherein the actuation assembly is configured to selectively move the cleaning member between the collapsed configuration and the expanded configuration by mechanical manipulation of the actuation assembly.

10. The cleaning device of claim 9, wherein the cleaning member comprises a covered scaffold.

11. The cleaning device of claim 10, wherein the covered scaffold comprises at least one of a membrane and film.

12. The cleaning device of claim 9, wherein the elongate body comprises an inner shaft and an outer shaft coupled to the control assembly, wherein a distal end of the inner shaft is coupled to a distal end of the cleaning member and a distal end of the outer shaft is coupled to a proximal end of the cleaning member, and wherein movement of the inner shaft relative to the outer shaft moves the cleaning member between the collapsed configuration and the expanded configuration.

13. The cleaning device of claim 12, wherein the actuation assembly comprises a handle and a trigger, wherein the trigger is coupled to the inner shaft and wherein the handle is coupled to the outer shaft.

14. The cleaning device of claim 13, wherein a proximal end of the handle comprises a grip configured to receive a thumb of an operator.

15. The cleaning device of claim 9, wherein the cleaning member comprises at least one wiper member.

16. The cleaning device of claim 9, wherein the cleaning member is coated.

17. The cleaning device of claim 9, wherein the elongate body comprises an inner lumen extending from the proximal end to the distal end, wherein the inner lumen is configured to receive a visualization scope to provide visualization through a viewing window located along a distal tip of the elongate member.

* * * * *